(12) United States Patent
Gross

(10) Patent No.: US 7,429,358 B1
(45) Date of Patent: Sep. 30, 2008

(54) METHOD AND APPARATUS FOR MEASURING GAS SORPTION AND DESORPTION PROPERTIES OF MATERIALS

(75) Inventor: Karl J. Gross, Fremont, CA (US)

(73) Assignee: Hy-Energy, LLC, Newark, CA (US)

( * ) Notice: Subject to any disclaimer, the term of this patent is extended or adjusted under 35 U.S.C. 154(b) by 823 days.

(21) Appl. No.: 10/440,069

(22) Filed: May 17, 2003

Related U.S. Application Data

(60) Provisional application No. 60/381,945, filed on May 20, 2002.

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. .................... 422/83; 422/50; 422/68.1; 422/69; 73/1.01; 73/1.02; 73/19.01; 73/23.2; 436/43; 436/144; 436/127; 436/181

(58) Field of Classification Search ............ 422/50, 422/68.1, 69, 83; 73/1.01, 1.02, 19.01, 23.2; 436/43, 127, 144, 181
See application file for complete search history.

(56) References Cited

U.S. PATENT DOCUMENTS

| | | | |
|---|---|---|---|
| 3,059,478 A | 10/1962 | Coggeshall et al. | |
| 3,732,736 A | 1/1973 | Glaude et al. | |
| 3,850,040 A | 11/1974 | Orr, Jr. et al. | |
| 4,661,415 A | 4/1987 | Ebato et al. | |
| 4,711,765 A * | 12/1987 | Cates et al. ............ | 422/89 |
| 4,762,010 A | 8/1988 | Borghard et al. | |
| 4,865,996 A * | 9/1989 | Castleman et al. ........ | 436/161 |
| 4,972,730 A | 11/1990 | Camp et al. | |

(Continued)

FOREIGN PATENT DOCUMENTS

EP 0538622 2/1994

(Continued)

OTHER PUBLICATIONS

Miyamoto M. et al., "Reaction Kinetics of LaNi$_5$", Journal of the Less Common-Metals, vol. 89, 1983, pp. 111-116.

(Continued)

*Primary Examiner*—Brian Sines
(74) *Attorney, Agent, or Firm*—Duane Morris LLP

(57) ABSTRACT

The invention relates to a method and an apparatus (herein referred to as a "gas sorption/desorption analyzer") for measuring the gas sorption properties of substances (for example hydrogen sorption by metal alloys). Measurements include: Pressure Composition Temperature isotherm (PCT), Kinetic, Cycle-life, and density. Measurements are made by sorption of aliquots of gas to or from a sample of the substance. The amount of gas in each aliquot is determined from the gas pressure and temperature in calibrated reservoir volumes. The apparatus comprises components rated for operation up to 200 atm, a plurality of sensors covering a broad pressure range, and minimized volumes to enable accurate measurements of small samples. Aliquot pressures are controlled using a feed-back controlled pressure regulator that can also be used for constant pressure sorption measurements. The gas temperature is regulated using a temperature controlled enclosure. The apparatus also comprises a plurality of safety and failsafe mechanisms.

48 Claims, 27 Drawing Sheets a) Step 1 b) Step 2

U.S. PATENT DOCUMENTS

| | | | |
|---|---|---|---|
| 5,058,442 | A | 10/1991 | Yamanaka et al. |
| 5,133,219 | A | 7/1992 | Camp |
| 5,239,482 | A | 8/1993 | Ajot et al. |
| 5,342,580 | A | 8/1994 | Brenner |
| 5,360,743 | A | 11/1994 | Lowell |
| 5,591,897 | A | 1/1997 | Nakamura et al. |
| 5,895,841 | A | 4/1999 | Lowell |
| 6,257,835 | B1 * | 7/2001 | Kaehler ............ 417/205 |

OTHER PUBLICATIONS

Hwang, C. et al., "Diffusion of Hydrogen in Amorphous $Cu_{45}Ti_{55}$ Ribbon", Journal of the Less-Common Metals, vol. 89, 1983, pp. 215-222.

Karl Joseph Gross, Intermetallic Materials for Hydrogen Storage, Institut de Physique Universite de Fribourg, Suise, Theses No. 1217, 1998 Fribourg.

K.J. Gross, A. Züttel, L. Schlapbach, On the possibility of metal hydride formation, Part I: The Synthesis of $Mg_2Ni_5B_4$ by Mechanical Milling and Sintering, Journal of Alloys and Compounds 274 (1998) p. 234.

K.J. Gross, a. Züttel, L. Schlapbach, On the possiblity of metal hydride formation, Part II: Geometric considerations, Journal of Alloys and Compounds 274 (1998) 239.

K.J. Gross, P. Spatz, A. Züttel, L. Schlapbach, Mechanically milled Mg composites for hydrogen storage, The Tarnsition to a steady composition, Journal of Alloys and Compounds 240 (1996) 206.

K.J. Gross, P. Spatz, A. Züttel, L. Schlapbach, Mg composites for hydrogen storage, The dependence of hydriding properties on composition, Journal of Alloys and Compounds 261 (1997) 276.

K.J. Gross, D. Chartouni, E. Leroy, A. Züttel, L. Schlapbach, Mechanically milled Mg composites for hydrogen storage, The relationship between Morphology and kinetics, Journal of Alloys and Compounds 269 (1998) 259.

K.J. Gross, P. Spatz, A. Züttel, L. Schlapbach, The Hydriding Characteristics of CeMnAl and Related Alloys, Hydrogen Energy Progress XI, Proceedings of the 11th World Hydrogen Energy Conference, Stuttgart Germany (1996) 1281.

K.J. Gross, A. Züttel, L. Schlapback, In Situ Neutron Diffraction Study of the New Hydride $CeMn_{1.5}Al_{0.5}DX$ (0 <x<4), Journal of Alloys and Compounds, to be submitted.

* cited by examiner a) Step 1 b) Step 2 a) Step 1 b) Step 2

METHOD AND APPARATUS FOR MEASURING GAS SORPTION AND DESORPTION PROPERTIES OF MATERIALS

CROSS-REFERENCE TO RELATED APPLICATIONS

This application claims the benefit of U.S. Provisional Application No. 60/381,945, filed May 20, 2002 GROSS, "METHOD AND APPARATUS FOR MEASURING GAS SORPTION AND DESORPTION PROPERTIES OF MATERIALS"

BACKGROUND

1. Field of the Invention

The present invention relates to an apparatus (herein referred to as a "gas sorption/desorption analyzer") adapted to measure the adsorption and absorption (collectively referred to as "sorption") and desorption properties of a materials capable of gas sorption, and more particularly to an apparatus for measuring the hydrogen adsorbing, absorbing or desorbing properties of hydrogen absorbing alloys, hydrogen adsorbing carbons, and oxygen absorbing substances. The apparatus is unique in the following respects: 1) it can perform these measurement in a precise manner at high gas pressures (0 to 200 atm), 2) it performs these measurement by applying precise aliquots of gas at specific pressures using an automated pressure regulator, 3) it incorporates many unique features which enhance the precision, utility, and safety of the measurement. These features are described below in the summary of the invention.

Note: all pressures in atm are absolute pressures (atma). PID means Proportional Integral Differential.

2. Description of Prior Art

In recent years, much attention has been directed to hydrogen absorbing alloys for the negative electrodes of alkali batteries and for gaseous hydrogen storage. More recently, there has been an increased interest in complex hydrides and carbon materials for gaseous hydrogen storage. Typical examples of hydrogen absorbing alloys are $LaNi_5$, $MmNi_2Co_3$ (wherein Mm is a misch metal). In the case of $LaNi_5$, when hydrogen is absorbed it can form a solid solution alloy $LaNi_5H_x$, as well as a metal-hydride $LaNi_5H_6$, at near ambient temperatures and pressures. An example of a complex hydride that may be used for gaseous hydrogen storage is $NaAlH_4$ doped with titanium by reaction with $TiCl_3$. This material can release and re-absorb more than 3 weight percent hydrogen through solid-state processes of decomposing and reforming $NaAlH_4$. Hydrogen gas can also be absorbed onto and desorbed from graphite and other carbon materials low temperatures (less than $-100.\text{degree. C.}$). Potential applications for these materials are rechargeable alkali batteries, hydrogen storage for use with fuel cells, gas chromatographs, etc. Many of the hydrogen sorption/desorption properties of these materials can be modified and, ultimately, tailored to suit the desired application. For example, the pressure and temperature at which hydrogen sorption and desorption takes place in many hydrogen absorbing alloys can be changed by through minor changes in the alloy composition. Therefore, it is very important to measure the hydrogen absorption/desorption properties of all of these types of materials.

One aspect of the hydrogen sorption (or desorption) properties of a material is the thermodynamics of hydride formation (or decomposition). This is determined by measuring a pressure-composition isotherm (PCT) diagram. FIG. 1A shows an idealized version of such a PCT measurements. This diagram represents the relationship between the pressure (ordinate) and the amount of hydrogen absorption (abscissa) at three different sample temperatures. By performing such measurements at several different temperatures the enthalpy of hydride formation can be determined. This is done by plotting the natural logarithm of the plateau pressure (flat portion of the PCT diagram) versus inverse temperature resulting in a van't Hoff diagram. The enthalpy of hydride formation is taken from the slope of this plot. FIG. 1B shows an idealized version of such a van't Hoff diagram.

Another aspect of the hydrogen sorption (or desorption) properties of a material is the kinetics of hydride formation (or decomposition). This is simply the rate of hydrogen sorption or desorption from the material. This is generally determined by measuring the change in hydrogen pressure versus time in a fixed volume containing the sample. If the volume of the vessel and the volume and mass sample are known the amount of hydrogen sorption or desorption by the sample can be quantified. FIG. 2 shows an example of such a kinetics measurement for $La_2Mg_{17}$. By performing such measurements at several different temperatures the activation energy of hydride formation can be determined. This is done by plotting the natural logarithm of the rate (usually the initial linear portion of the kinetics measurement) versus inverse temperature resulting in an Arrhenius diagram. The activation energy of hydride formation is taken from the slope of this plot. FIG. 3 shows an example of such a van't Hoff diagram for $La_2Mg_{17}$.

A third and very important aspect of the hydrogen sorption (or desorption) properties of a material is the cycle life. That is, how the hydrogen capacity and kinetics hold up with repetitive hydrogen sorption and desorption cycles. In practice, this consist of making a series of kinetics measurements and quantifying the changes in capacity and kinetics as a function of the number of cycles.

The most common way to measure these hydrogen sorption properties of a material is to measure the drop in pressure in a calibrated volume as hydrogen is adsorbed or absorbed by a test sample of the material. Likewise, desorption properties are determined by measuring the increase in pressure in a calibrated volume as hydrogen is desorbed from the test sample into the volume. The quantity of hydrogen absorbed (adsorbed) or desorbed in each measurement is found from the equation of state of gaseous hydrogen. The equation of state is well approximated by the ideal gas law at pressures below about 10 atm. Above this pressure, non-ideal gas laws or tables of experimentally determined values may be used. In any case, it is necessary to know three parameters to determine the quantity of hydrogen absorbed (adsorbed) or desorbed. These are, the pressure, temperature and volume of the gas. By holding the volume and temperature constant, the quantity of hydrogen is determined simply by measuring the pressure. Knowing the mass of the sample it is then possible to determine the mass concentration of hydrogen that has been absorbed (adsorbed) or desorbed by the sample. If the composition of the sample is well known, then the stoichiometry of hydrogen in the sample may also be determined from the measured concentration.

In a PCT measurement, the sample is dosed with small "aliquots" of hydrogen from a small volume or desorbed into a small volume such that only a small fraction of hydrogen is absorbed (adsorbed) or desorbed at one time. A sorption PCT diagram is measured by increasing the pressure in each aliquot of hydrogen applied to the sample in a step-wise fashion. Similarly, a desorption PCT diagram is measured by decreasing the pressure in a step-wise fashion, in the small volume into which the sample is desorbed. The conventional apparatus for performing such measurements is referred to as a Sieverts' device. Such a device is shown in the schematic illustration of FIG. 4.

While this simple device has been used extensively over the years to make hydrogen sorption and desorption measurements, there are a number of technical issues which plague the accuracy and ease with which these measurements can be made. The following is a list and description of the most important problems effecting the prior art. The present invention overcomes each of these problems through the use of unique, effective, and simple, hardware or software solutions.

Problem 1: Automation. Most measurements require data collection over long periods of time and may involve large numbers of repetitive operations (such as delivering aliquots in a PCT measurement, or switching between sorption and desorption in cycle-life measurements). This stresses the importance of using automation in such measurements. The present invention comprises an automated gas sorption/desorption analyzer that employs computer controlled operations and data collection.

Problem 2: Uniform PCT Gas Aliquots. Providing an evenly spaced distribution of sorption/desorption measurement points along PCT curve is of critical importance because without a detailed and even distribution of measurements the low pressure region of the PCT plot will not be well resolved. The result is that the solid solution portion of the hydrogen behavior may not be observed at all. In the worst case, which has been known to occur, changes in the equilibrium plateau pressure identified with hydride phase transitions could be missed entirely.

The classic Sieverts apparatus uses a fixed applied pressure equal to the highest pressure of the measurement for sorption and usually vacuum for desorption. This creates the undesirable situation of requiring very large aliquots of gas for the initial portion of sorption measurements and the reverse for desorption. The best approach to resolve this problem is to be able to vary the applied pressure at will. One method which addresses this problem is described in U.S. Pat. No. 5,591,897. In that method three automated valves work in conjunction to step the applied pressure up or down to the desired aliquot pressure. The method consists of alternately filling (or emptying) a first volume with hydrogen by opening a primary valve, closing the primary valve and then opening a secondary valve to the reservoir volume. In this manner the pressure is stepped up or down to the desired pressure prior to application of the aliquot to the sample. The disadvantage of this method is that every point measured on a PCT curve requires a tedious process of multiple valve operations in order to reach the desired pressure. This process takes time, increases the noise level of the measured response produced by such devices, and greatly increases wear on the automated valves. In addition, during the time that it takes for this process to be completed hydrogen interaction with the material of interest may continue to proceed within the sample volume. This will contributes to a certain amount of error in the measurements of hydrogen capacity.

Another method uses a needle valve to increase or decrease the supply pressure. The problem with this method is that the supply pressure increases or decreases without feed-back control. Because of this, the supply pressure will not be adjusted with respect to changing conditions during gas sorption or desorption to or from the sample. For example, during a hydrogen absorption PCT measurement of a metal hydride the equilibrium pressure will rise until the plateau pressure is reached. The supply pressure, on the other hand, will continue to rise. The increasing difference between the equilibrium pressure and the supply pressure will cause the data points to spread out as the measurement continues. Important phase change information towards the end of the plateau may be missed. The increasing applied pressure differential may also lead to non-equilibrium conditions as the measurement progresses. In addition, needle valves demonstrate non-linear behavior such that the supply pressure will increase (or decrease) more slowly as the pressure differential across the needle valve decreases. This non-linearity often causes sorption PCT measurements to slow down at high pressures to the point where the measured change in ad/absorbed gas is less than the systematic error. For desorption PCT's with plateau pressures near or below one atmosphere the pressure differential across the needle valve is reduced to the point that there is very little flow and the measurement essentially stalls when the plateau is reached.

These problems are easily overcome in the present invention by using an automated pressure regulator to supply the working gas either at a predetermined pressure or at a specified pressure difference above or below the measured equilibrium pressure. In an alternative embodiment the working gas can be supplied (or removed) at a controlled flow rate using a gas flow controller.

Problem 3: Constant Gas Temperature. Variations in the air temperature in the room in which a volumetric instrument such as that shown in FIG. 4 can produce significant errors in calculating the quantities of hydrogen sorption or desorption from a material. Even if the surrounding air temperature is measured and introduced into the equation of state, the lag time between changes in the temperature of the surrounding air and the temperature of the hydrogen gas in the Sieverts apparatus can be significant enough that the data can not be sufficiently corrected. The problem of variations in the temperature of hydrogen gas in a Sieverts' apparatus can be resolved in two ways. The first is to position a temperature measuring device such as a thermocouple inside of the gas reservoir volume to get an accurate measurement of the gas temperature. This value can then be used in the equation of state to compensate for temporal changes in the temperature of the gas. The problem with this method is that if the apparatus employs several separated volumes and interconnecting tubing the gas temperature in the system may not be equilibrated to the temperature measured in one part of the apparatus. The second solution is to maintain the main body of the apparatus at a fixed temperature. This can be accomplished by submerging the main body of the apparatus in a controlled temperature bath (usually using a water bath). The inherent difficulty with this is that there are commonly many electrical devices such as pressure transducers that are connected to the apparatus which are not compatible with water. Another approach is to have the main body of the apparatus in thermal contact with a temperature controlled thermal ballast. This is typically a large metal plate which is heated and maintained at a fixed temperature slightly above room temperature by an electrical heater and a feedback control system. The difficulty with this concept is to obtain good enough heat transfer throughout the apparatus that the gas temperature is truly constant through out the system.

The best approach and one aspect of the present invention is to regulate the gas temperature by placing the main gas handling portion of the apparatus (gas sorption/desorption analyzer) in an enclosure and regulating the air temperature within the enclosure to a fixed value slightly above room temperature Problem 4: Gas Temperature When Sample is Heated. To calculate the quantity of gas adsorbed, absorbed (hereafter "ad/absorbed"), or desorbed in a volumetric measurement, it is also necessary to know the temperature of the gas. This is not a problem if the gas temperature is uniform throughout the gas handling system, as provided in the present invention by using a controlled temperature enclosure. However, if the sample is heated, or the temperature is different for the gas handling portion of the apparatus outside of the enclosure, then the exact temperature of the gas is not known. This may cause significant errors in quantifying gas sorption.

The present invention overcomes this problem through two methods. The first is to measure the temperature of the gas within the enclosed part of the gas handling system as well as the temperature of the gas in the sample container. The operator is then given the option to use a weighted average of the gas temperature in calculating the quantity of gas (weighted by relative volume of gas at each temperature). A second, and even more effective manner, to overcome this problem is to reduce the volume of the heated gas to a minimum. This is accomplished in the present invention by using small diameter external gas lines and spacers in the sample container to reduce the volume of gas that at a different temperature than the main body of gas in the enclosed and temperature regulated gas handling system.

Problem 5: Non-ideal Gas Behavior at Elevated Pressures. At pressures above about 20 atm molecular interactions in gases begin to have an effect on the relationship between pressure, temperature, volume of a given quantity of gas. These effects cause a deviation from the "ideal gas" behavior. The properties of the gas are no longer adequately described by the linear Ideal Gas Law. This deviation can cause errors in using pressure measurements of a volumetric device to determining the amount of gas that is ad/absorbed or desorbed by a sample. At pressures above 100 atm, this error may be significant (on the order of 5% or more).

These errors can be successfully overcome by utilizing one of the several non-ideal equations of state developed for gases at high pressure. The present invention includes data analysis software employing automatically calculation of non-ideal gas behavior to correctly determine the hydrogen capacity from changes in pressure.

Problem 6: Small sample quantities. Small samples (<1 gram) and/or samples that ad/absorb only small quantities of gas (50 milliliters) are difficult to investigate using typical volumetric devices that often have calibrated volumes and piping with volumes on the order of 50 milliliters or more. For example, a 0.5 gram sample of a $LaNi_5$.-type alloy subjected to a 2 atm aliquot of hydrogen gas from a 50 milliliter calibrated reservoir volume will be completely hydrided in one step. Under such conditions it would not be possible to measure an equilibrium PCT plateau curve.

The present invention utilizes small gas vessels, spacers, and small internal diameter gas lines (c.a. 1 mm diameter) to reduce the minimum working volumes to about 15 milliliters. This enables the measurement of gas sorption properties of small (<1 gram) samples and samples with limited gas sorption. For larger samples and for desorption, the present invention includes additional calibrated volumes to increase the working volume of the gas sorption/desorption analyzer. These volumes may be accessed by opening valves connecting them to the gas handling system.

Problem 7: Flexibility in Measuring Different Sample Types and Sizes. The calibrated reservoir volume may be too large or too small for the aliquot that is desired. The most obvious example is that a very small volume (15-50 milliliters) is needed for making absorption kinetics measurements using high pressures (100 atm) and a large volume is needed for a desorption kinetics measurement (1 liter at <2 atm). In addition, different types of measurements (PCT, kinetics, and cycle-life) as well as, different types or quantities of samples (1 gram vs. 100 grams) may all have different requirements for the quantity of gas to be supplied or desorbed in an aliquot. Simple Sievert's devices often provide only one or two different calibrated volumes, or required the volumes to be changed manually. The problem with a manual change is that air will be introduced into the system, requiring an additional out-gassing. Also, such hardware changes significantly increase the possibility of system leaks, lost hardware, and possible mistakes or changes in the calibration of the actual volumes being used. There is a great advantage to being able to change to a reservoir of a different volume, even during a measurement.

As mentioned above, the present invention includes at least 3 additional calibrated volumes permanently attached to the gas handling system that are accessed when needed by opening automated valves that connect these volumes to the gas handling system.

Problem 8: Gas Sorption and Desorption Properties May Vary Over a Broad Time Range. It is common that gas sorption or desorption rates will vary by over 2 orders of magnitude during a single measurement. For example, a hydride may absorb hydrogen at 10 wt. %/minute in the first few minutes of a kinetics measurement and continue to absorb hydrogen but at a much lower rate of 0.1 wt. %/minute after several hours. Ideally, one would like to record such data frequently during the rapid part of the measurement and less frequently when changes are occurring slowly. The problem with current data-collection schemes is that data is taken at a fixed time interval. To be able to collect all the pertinent information data must be collected at the shortest required time interval (e.g. 2 seconds). Unfortunately, doing this for a measurement that often lasts hours or days creates enormous data files. And a large portion of the data collected after the most active part of the measurement will be of little value since dozens or hundreds of data point could be equally as well represented by a single data point. Sometimes it is possible to change this interval during a measurement, but this requires operator to be input new values and therefore, they must schedule their time accordingly.

The present invention overcomes this problem by taking advantage of the fact that for typical experiments, gas sorption and desorption rates decrease as a function of time. The present invention includes different algorithms to decrease the frequency with which data is recorded as a function of time. These algorithms are described in a later section.

Problem 9: Constant Pressure Measurements. It is often very useful to be able to make gas sorption or desorption measurement while maintaining a constant active gas pressure over the sample. This is important for kinetic comparison or mechanism studies because kinetics are often strongly influenced by changes in the applied pressure. This is also important in simulating real conditions encountered in applications, such as filling up a hydride bed under a constant hydrogen pressure. Currently, volumetric systems measure gas sorption (of desorption) properties of materials by measuring the pressure drop (or rise) in a calibrated volume which contains the sample material. The need to measure a moderate change in pressure to obtain accurate data means that the sample is subjected to a non-constant pressure during the measurement which may have a significant effect on the results.

The present invention overcomes this problem by employing a computer controlled pressure regulator for gas sorption and a computer controlled back-pressure regulator for desorption measurements. These devices are used to maintain a constant gas pressure over the sample during measurements.

The quantity of gas ad/absorbed in a sorption measurement is determined by measuring the drop in pressure in a small (100 milliliter) calibrated volume which supplies the gas to the sample through the pressure regulator. In desorption measurements, the quantity of gas desorbed is determined by measuring the pressure increase in a large (1 liter) calibrated volume to which the gas flows from the sample through the back-pressure regulator.

Problem 10: Changes in Sample Density. Hydrides undergo lattice expansion during hydrogen absorption and lattice contraction during desorption causing minor changes in the calibrated system volumes. These changes are typically not accounted for in the prior art. In addition, it is of interest to be able to measure these expansions and contractions.

The present invention overcomes this problem by performing semi-automatic measurements of the volume (and therefore packing density) of the sample using an inert gas such as He to measure the empty volume of the sample container with and without the sample present. Changes in the sample volume may be made during sorption or desorption experiments by performing a volume measurement with the inert gas at selected intervals during the experiment.

Problem 11: Large Dynamic Pressure Range. The measured pressure often extends over a larger dynamic range than most pressure transducers can measure with good accuracy. In typical devices of the prior art, only one pressure transducer is employed, limiting the range over which experimental measurements can be performed.

The present invention overcomes this problem by utilizing at least two pressure transducers, one covering a low pressure range (e.g. 0-20 atm) and another for higher pressures (e.g. 20-200 atm). Computer controlled automation (PCT, kinetics and cycle-life) is used to determine at any point in an experiment whether the pressure is in the range that should be measured using either a low range transducer or a high range transducer. In the case of the present preferred embodiment of the invention two transducers are used. The pressure is first measured with the high-range transducer. If the high-range transducer indicates a low enough value (below a selected set point), an automated valve is opened to allow the pressure to be measured with the low-range transducer. The automated valve is used to protect the low-range pressure sensor from damage by over-pressurization. In this case the change in the calibration volume is adjusted to account for the additional volume of the low-range transducer, valve and connections.

Problem 12: Elevated Pressure and Temperature Operation. Many materials require temperatures and pressures substantially above ambient conditions (ca. 400.degree. C. and 200 atm.) The prior art has focused on measurements of hydrogen absorption in classic interstitial metal hydrides for hydrogen gas storage and battery applications. In most cases, these materials have equilibrium hydride formation plateaus that are measured either near ambient conditions or at elevated temperatures (e.g. $MgH_2$ at 300.degree. C.) and pressures of 30 atm or less. It is desirable (particularly in light of new reversible hydride development e.g. Ti doped $NaAlH_4$) to be able to make measurements at higher pressures and temperatures. The currently available systems either do not go to pressures above about 30 atm, are not accurate at temperatures above 300.degree. C., or are not automated.

The present invention overcomes this problem by using high-pressure components, lines, fittings, and a sample container which are rated for hydrogen service up to 200 atm. The present invention also includes a sample container which is rated for service at up to 400.degree. C. at 200 atm of hydrogen. Errors caused by variations in the gas temperature when operating at this high sample temperature are minimized by reducing the empty volume of the external gas handling system and sample container, as well as offering the option to use a weighted average temperature for concentration calculations. The present invention also includes automated pneumatic valves, and the use of valves in series to minimize the leak rates across the valves when performing high-pressure measurements. Automated valves also have a great advantage with respect to durability and life-time of an apparatus. This is because they are operated in a repeatable and consistent manner which significantly reduces damage to the internal components. Manual valve are subjected to the inconsistent behavior of the operator. In particular, when used with high-pressure the experimenter has a tendency to over-tighten such valve, which will damage the valve seat and cause the valve to leak. Manual systems have been known to operate for only a few experiments before the valves leak to the point that the data is seriously compromised. Automated pneumatic-valves, on the other hand, can be set to operate over thousands of cycles using an air pressure that is appropriate and constant.

Problem 13: Air Exposure. Typical prior-art apparatus have been designed such that the sample cannot be place in the sample container or that the sample container cannot be connected to the apparatus without exposing the sample to air. This is a very big problem for samples that become inactive because of the formation of surface oxides or other coatings and is a serious problem for samples which are highly reactive with air such as Na—Al—H compounds.

The present invention overcomes this problem by using a sample container that is small enough to fit through an entry chamber of a glove box so that it can be loaded with samples in an inert atmosphere such as argon gas. In the present invention, the sample container is comprised of the body of the container with two open ends. This has two advantages, the first is that samples can be easily loaded and more importantly easily removed from the sample container. The other advantage is that different types of end-pieces can be attached to each end. In the preferred embodiment one end-piece has a valve between the body of the sample container and a connector for attaching the sample container to the external gas-handling system of the gas sorption/desorption analyzer. This allows the sample to be sealed under an inert atmosphere while the sample container is removed from the glove box attached to the gas sorption/desorption analyzer and all lines of the gas sorption/desorption analyzer are pumped free of air. In this manner the sample is loaded, transferred and ready for measurements without ever being exposed to air. In the preferred embodiment, the other end of the sample container is sealed with a fitting that contains a tube closed at one end and sealed to the fitting. This tube is known as a thermocouple "well". It runs up inside of the sample container to make precise measurements of the actual sample temperature. In an alternative embodiment, this end-piece could be replace with another valve and connector end-piece. This allows other devices to be attached in an air-less manner to the sample valve. Such devices could be a turbo-molecular pump, gas or liquid vessel containing a reactive or calibration gas or liquid, a residual gas analyzer, etc.

Problem 14: Safety. Measurements made using high-pressure hydrogen at high temperature and in many cases with highly reactive materials presents many safety issues and challenges that are not properly addressed in much of the prior art.

The present invention comprises several innovative hardware and control logic mechanisms to improve safety. Examples include failsafe mechanisms, such as a pop-top, which will minimize that would otherwise be caused by a build-up of hydrogen and ignition within the gas sorption/desorption analyzer enclosure. Other examples include logical mechanisms, such as temperature limits for the enclosure heating system and sample-container heater which are built into the control software. These mechanisms will be discussed in detail below.

SUMMARY OF THE INVENTION

The following is a summary of the novel aspects of the invention:

1. The use of gas handling components that function at high and low gas pressures (0 to 200 atm) to allow the measurement of gas sorption properties of materials over a broad range pressures and in particular at high pressures.
2. The use of two different pressure transducers to cover a broad range of pressures with increased accuracy. One transducer covers a low-pressure range with precision (e.g. 0 to 7 atm) and the other a high-pressure range with precision (e.g. 0 to 200 atm). An automated valve and control software protect the low-pressure transducer from the damaging effects of high pressure by first reading the high-pressure transducer and only then opening the valve to the low-pressure transducer if the pressure is below a safe limit (e.g. 7 atm).
3. The apparatus control and measurement software automatically compensates for the non-ideal behavior of gases at high pressures (>10 atm) to correctly determine the amount of gas sorbed or desorbed from a sample.
4. Gas is automatically applied to or removed from a sample in aliquots from one of several calibrated volumes. The amount of gas in the aliquot is precisely controlled by adjusting the pressure in the calibrated volume using an automated PID controlled pressure regulator. The automated pressure regulator is a unique addition to this type of apparatus and in particular the use of an automated regulator that functions at high pressures.
5. Precise low-pressure aliquots are obtained by accurately setting a high pressure in a small calibrated volume and then releasing this gas to a larger calibrated volume. The final low pressure is accurately obtained by setting the initial high-pressure to an exact predetermined value based on the ratio of the small and large volumes.
6. The automated pressure regulator combined with a calibrated volume on the inlet of the automated pressure regulator allows the unique possibility to make quantitative gas sorption measurements with the sample exposed to a constant pressure. A back-pressure regulator attached to the sample holder can provide the same possibility for desorption measurements.
7. In order to make precise volumetric measurements of gas sorption/desorption from a sample, it is necessary to know the pressure, volume and temperature of the working gas. The pressure is measured, the volume is fixed and likewise, in this apparatus the temperature of the gas is fixed. This is done by active heating of all (or nearly all) of the gas handling portions of the apparatus inside an insulated enclosure. The temperature is maintained at a constant value by using a PID feedback control of the electrical heating element and circulating air in the enclosure using an electric fan.
8. The use of fully automated valves (generally pneumatic valves) provides a powerful benefit of dramatically increasing the ease and productivity of measurements. For, example PCT, kinetics, and especially cycle-life measurements can be performed without the operator being present. One particularly unique automated process is to use the automated valves and calibrated volumes to calibrate the gas volume of sample holder with and without a sample in it. Ordinarily this is a very tedious manual process. The volume with the sample must be measured to perform precise gas sorption/desorption measurements. The difference between the volumes with and without the sample can be used to determine the density and packing-density of the material. In addition, this automated process can be used to measure density changes (volume expansion) of substances in situ, during the sorption or desorption processes.
9. The apparatus is novel in providing several different combinations of calibration volumes of different size (generally 3 to 1500 ccm). This allows small aliquots for PCT measurements and large aliquots for kinetics and cycle-life measurements. Thus a broad range of gas quantities can be measured. The very small volumes enable PCT measurements on small samples (<1 gram). In addition, using the large volumes which are also rated for high-pressure use, PCT measurements can be performed on very large samples (>10 kg).
10. The apparatus as described herein provides 16 novel safety features to enhance the safe operation of the invention when using high-pressure, flammable, reactive, or toxic gases.

The present invention relates to an apparatus (gas sorption/desorption analyzer) for measuring gas adsorption, absorption, and/or desorption properties of a sample or substance having a property to absorb a gas. The gas sorption/desorption analyzer comprises a sample container for containing the sample or substance, gas storage consisting of one or more calibrated volumes connected to the sample container, a gas supply source for supplying the gas to the gas storage, a vent line and a vacuum line to discharge gas from the gas storage, pressure transducers to measure the gas pressure over an extended range, an automated pressure regulator to charge or discharge the gas storage to a predetermined pressure, automated pressure regulators to maintain constant gas pressure over the sample during sorption or desorption, automated valves for controlling the flow of gas within the gas sorption/desorption analyzer, an air supply system to provide air to control the automated valves and pressure regulators, a calibration gas system to provide an inert gas for volume calibrations and density measurements, an automated sample container valve to automate experimental preparations, a heated enclosure to maintain a constant gas temperature in the gas storage, an automated heater for heating a sample in the sample container, an electrical data-acquisition and control system, a safety systems comprised of, a safety shield, a failsafe top panel, a sample heater open shield cut-off, a system of open panel power cut-offs, over-temperature cut-offs on the enclosure heater and sample heater, failsafe hydrogen leak mechanisms, gas-handling system and sample-container pressure relief mechanisms, and methods or means to compensate for non-ideal gas conditions, to correct or avoid errors due to variations in gas temperature, to small sample sizes, to low concentrations, to prevent sample air exposure, to measure changes in sample densities, to reduce the amount of data collected, and to provide uniform gas aliquots.

The primary object of the invention is to provide an automated means of measuring gas adsorption, absorption and desorption in materials. Other objects of the invention include the following:

1. to provide a method of controlling pressure during gas sorption or desorption measurements;

2. to provide a method of maintaining a constant gas pressure around a sample during gas sorption or desorption measurements;
3. to provide better apparatus for measuring gas sorption and desorption properties of materials by maintaining a constant gas temperature;
4. to provide a measuring apparatus that works with high-pressure gases and control software that corrects for the non-ideal behavior of gasses at high pressure;
5. to provide an apparatus for measuring gas sorption or desorption of materials that aids the operator by performing volume calibrations through a semi-automated process;
6. to provide an apparatus that performs sample density measurements in addition to gas sorption and desorption measurements;
7. to provide an apparatus that measures gas sorption and desorption over a wider dynamic range of pressures than those currently available;
8. to provide an apparatus that measures gas sorption and desorption properties of materials over a wider range of gas concentrations than can be done using existing technology;
9. to provide a sample container that provides better data, allows airless sample transfers and is easier to use;
10. to provide improved safety features in an apparatus that measures gas sorption and desorption properties of materials.

Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

Figure 1:
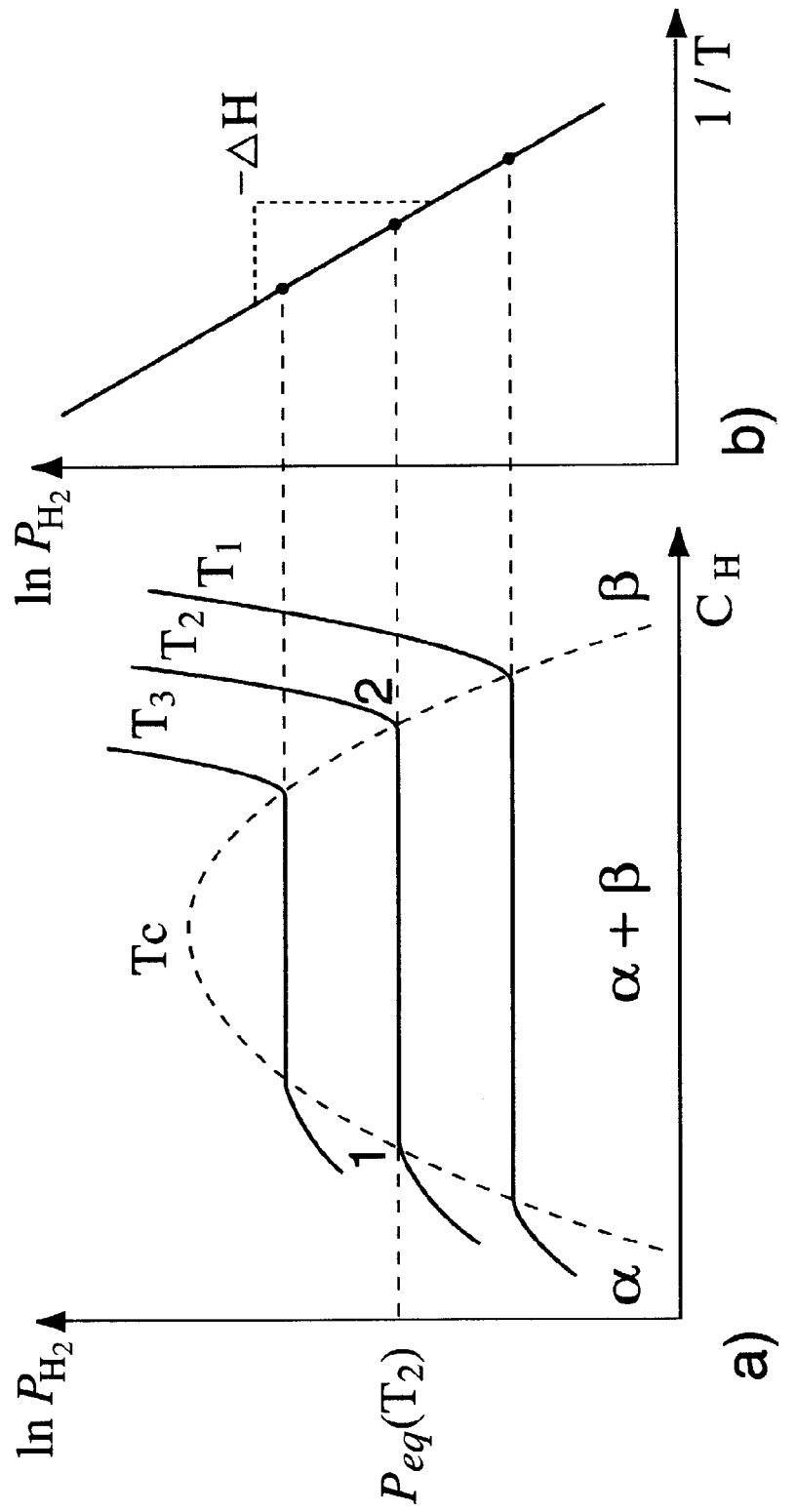
FIG. 1a) is an example of a typical PCT plot; and 1b) an example of a van't Hoff diagram.

| | |
|---|---|
| 501 | gas sorption/desorption analyzer |
| 502 | enclosure |
| 503 | panels |
| 504 | frame |
| 505 | feet |
| 506 | computer |
| 507 | communication link |
| 508 | main power switch |
| 509 a-f | temperature measurement inputs |
| 510 | sample heater power supply plug |
| 511 | vent for an electronics compartment |
| 512 | vent for a gas handling compartment |
| 601 | air connector |
| 602 | air supply line |
| 603 | air controller |
| 604 a-j | air control solenoids |
| 605 | variable air control line |
| 606 | gas pressure regulator |
| 607 | calibration gas connector |

-continued

| | |
|---|---|
| 608 | calibration gas supply line |
| 609 | calibration gas check valve |
| 610 | calibration gas line |
| 611 | calibration gas pressure relief valve |
| 612 a-j | automated valve |
| 613 | gas connector |
| 614 | gas supply line |
| 615 | gas supply line |
| 616 | gas vessel |
| 617 | supply gas input pressure transducer |
| 618 | gas supply line |
| 619 | supply gas output pressure transducer |
| 620 | gas line |
| 621 | discharge line |
| 622 | discharge pressure relief valve |
| 623 | vacuum line |
| 624 | vacuum connector |
| 625 | vent line |
| 626 | vent connector |
| 627 | gas line |
| 628 | gas line |
| 629 | gas vessel |
| 630 | gas line |
| 631 | gas vessel |
| 632 | gas line |
| 633 | high pressure transducer |
| 634 | gas line |
| 635 | gas connector |
| 636 | gas line |
| 637 | low pressure transducer |
| 638 | low pressure transducer failsafe pressure relief valve |
| 639 | enclosure heating element |
| 640 | enclosure air circulating fan |
| 701 | furnace |
| 702 | jack-stand |
| 703 | furnace power cord |
| 704 | furnace power plug |
| 705 | sample thermocouple |
| 706 | sample container thermocouple |
| 707 | furnace thermocouple |
| 720 | back-pressure regulator |
| 721 | back-pressure regulator input gas line |
| 722 | gas connector |
| 723 | back-pressure regulator output gas line |
| 724 | gas connector |
| 725 | back-pressure regulator input pressure transducer |
| 726 | back-pressure regulator output pressure transducer |
| 727 | pressure transducers power and signal wires |
| 728 | back-pressure regulator pneumatic PID controller |
| 729 | back-pressure regulator air line |
| 801 | sample container |
| 802 | valve top female nut |
| 803 | valve copper gasket |
| 804 | valve top gland |
| 805 | sample container valve |
| 806 | valve bottom gland |
| 807 | valve bottom female nut |
| 808 | sample container copper gasket |
| 809 | sample container top male nut |
| 810 | sample container top gland |
| 811 | sample container body piece |
| 812 | sample container conductive jacket |
| 813 | sample container spacer |
| 814 | sample |
| 815 | thermocouple well |
| 816 | sample container bottom gland |
| 817 | sample container bottom male nut |
| 818 | sample container bottom female nut |
| 819 | sample container bottom plug |
| 820 | sample thermocouple |
| 820 | sample thermocouple |
| 901 | external gas handling portion |
| 902 | external gas line |
| 903 | external female connector |
| 904 | external bulkhead connector |
| 905 | supporting arm |
| 906 | mounting bracket |
| 907 | angle bracket |
| 908 | extension bracket |

-continued

| | |
|---|---|
| 909 | connector bracket |
| 1001 | heating jacket |
| 1002 | heat resistant fabric |
| 1003 | insulation |
| 1004 | resistive heating element |
| 1005 | fastener |
| 1006 | power cord |
| 1007 | power plug |
| 1101 | electrical system |
| 1102 | Gas sorption/desorption analyzer power plug |
| 1103 | Enclosure power safety switch |
| 1104 | 110 V AC power in |
| 1105 | 110 V AC fuse |
| 1106 | 110 V AC power out |
| 1107 | 110 V AC to 24 V DC transformer |
| 1108 | 24 V DC power lines |
| 1109 | Sample heater control relay |
| 1110 | Data acquisition, control and safety system |
| 1111 | Communications control huh |
| 1112 | Analog input device |
| 1113 | Digital output device |
| 1114 | Pressure regulator analog output device |
| 1115 | Back-pressure regulator analog output device |
| 1116 | Enclosure heating element 110 V AC analog output device |
| 1117 | Thermocouple input device |
| 1118 | Enclosure heating element 110 V AC line |
| 1119 | Sample heater 110 V AC line |
| 1120 | Sample heater relay control line |
| 1121 | Sample heater safety shield switch |
| 1122 | Pressure transducer output lines |
| 1123 | Enclosure thermocouple |
| 1124 | air solenoids control lines |
| 1125 | Pneumatic valves air control lines |
| 1126 | Enclosure heater safety switch |
| 1127 | Power safety relay |
| 1201 | Sample container safety shield |
| 1202 | see-through safety shield |
| 1203 | Vent hole |
| 1204 | Safety shield hinge |
| 1205 | Safety shield latch hook |
| 1206 | Safety shield latch pin |
| 1207 | Safety shield handle |
| 1301 | Failsafe top panel |
| 1302 | gas handling compartment top panel |
| 1303 | top panel hinge |
| 1304 | top panel weak fastener |
| 1401 | Automated sample container valve system |
| 1402 | Automated sample container valve |
| 1403 | Valve top connector |
| 1404 | Valve bottom connector |
| 1405 | Automated sample container valve air connector |
| 1406 | Automated sample container valve air line |
| 1407 | Automated sample container valve connector |

DETAILED DESCRIPTION OF THE PREFERRED EMBODIMENTS

The present invention relates to an apparatus (gas sorption/desorption analyzer) for measuring gas sorption (herein understood to mean either adsorption or absorption) and/or desorption properties of a substance having a property to absorb a gas. In the preferred embodiment, the substance is any hydrogen absorbing material consisting of an element, compound, alloy or combination thereof. The working gas described herein is hydrogen, but it is to be understood that the invention is not limited to hydrogen alone. For example, in another embodiment the invention is useful for a substance which forms a nitride by absorbing nitrogen or an oxide by absorbing oxygen or adsorbs gases such as oxygen, carbon dioxide, hydrocarbons, etc. The apparatus can be used for any gas which reacts or is absorbed, adsorbed or desorbed by a sample or substance which may be either solid or liquid. In the following disclosure, the substance to be measured for gas sorption and/or desorption properties is referred to as the "sample" and the working gas (in this case hydrogen) is referred to as the "gas". Other gases employed in the process of making measurements, but not used as the working gas, are referred to as "air" and "calibration gas".

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

APPARATUS

Main Body of the Device

Figure 5A:
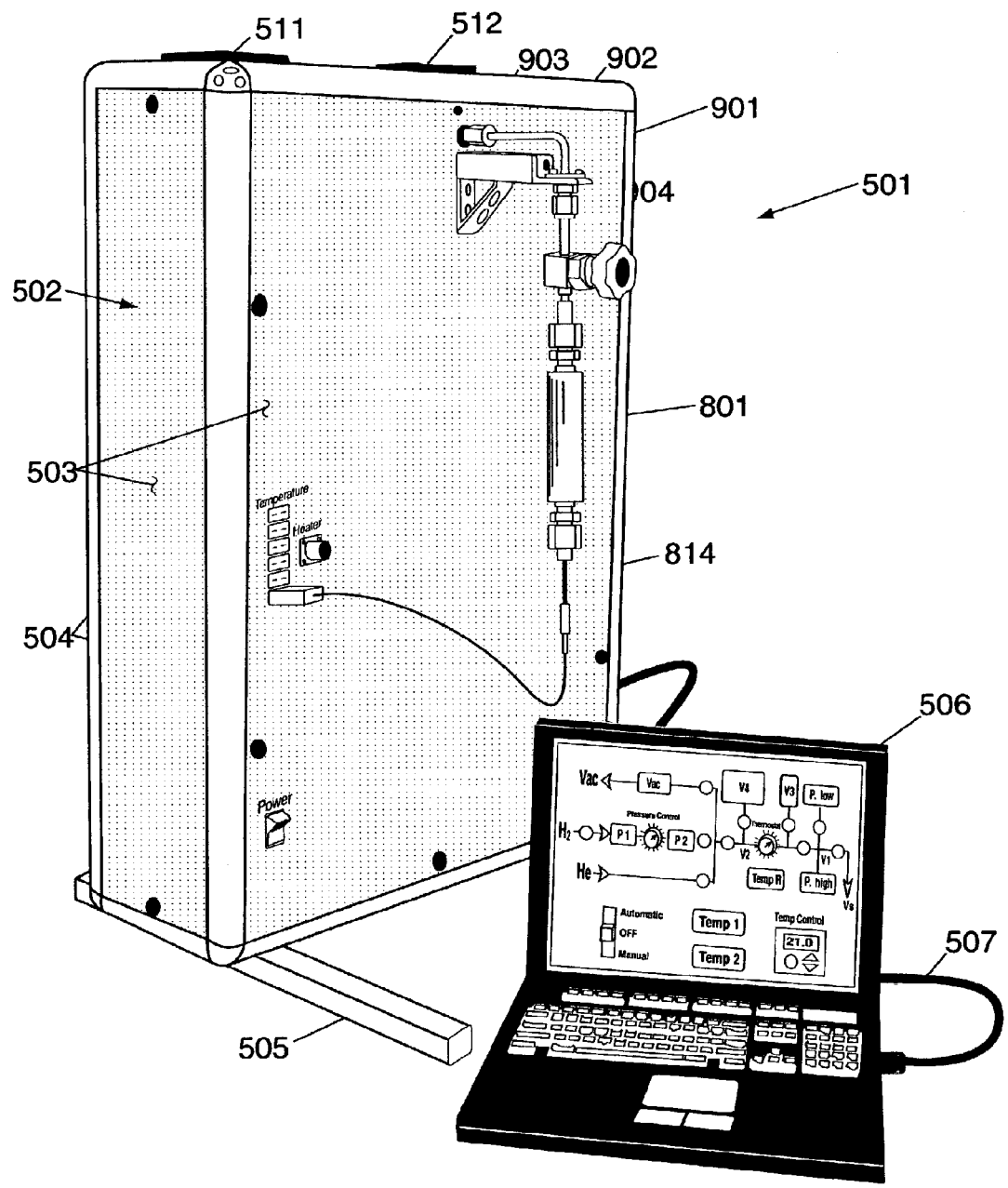
FIG. 5a-d) are illustration showing different embodiments of the invention.
Figure 5B:
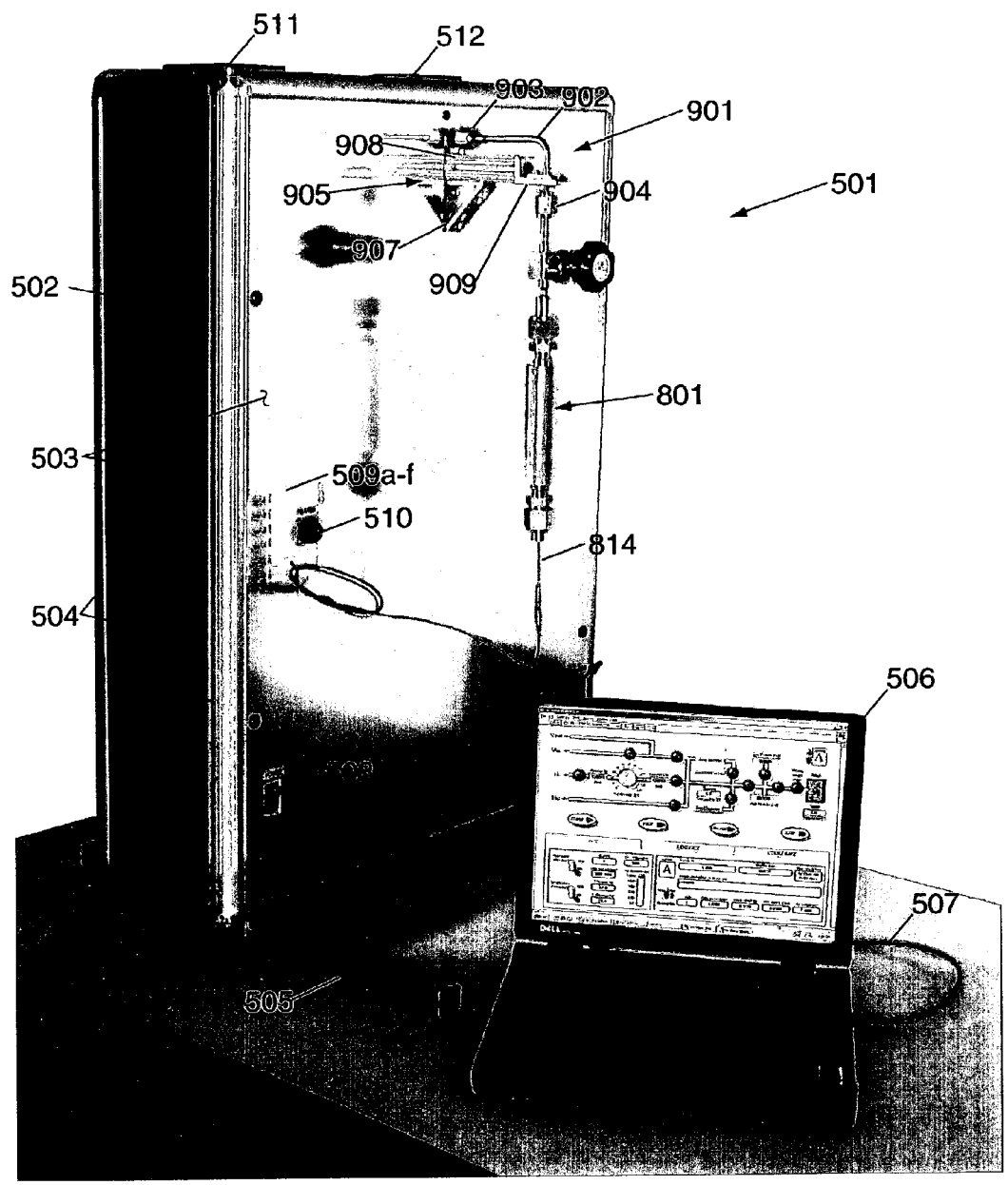
Figure 5C:
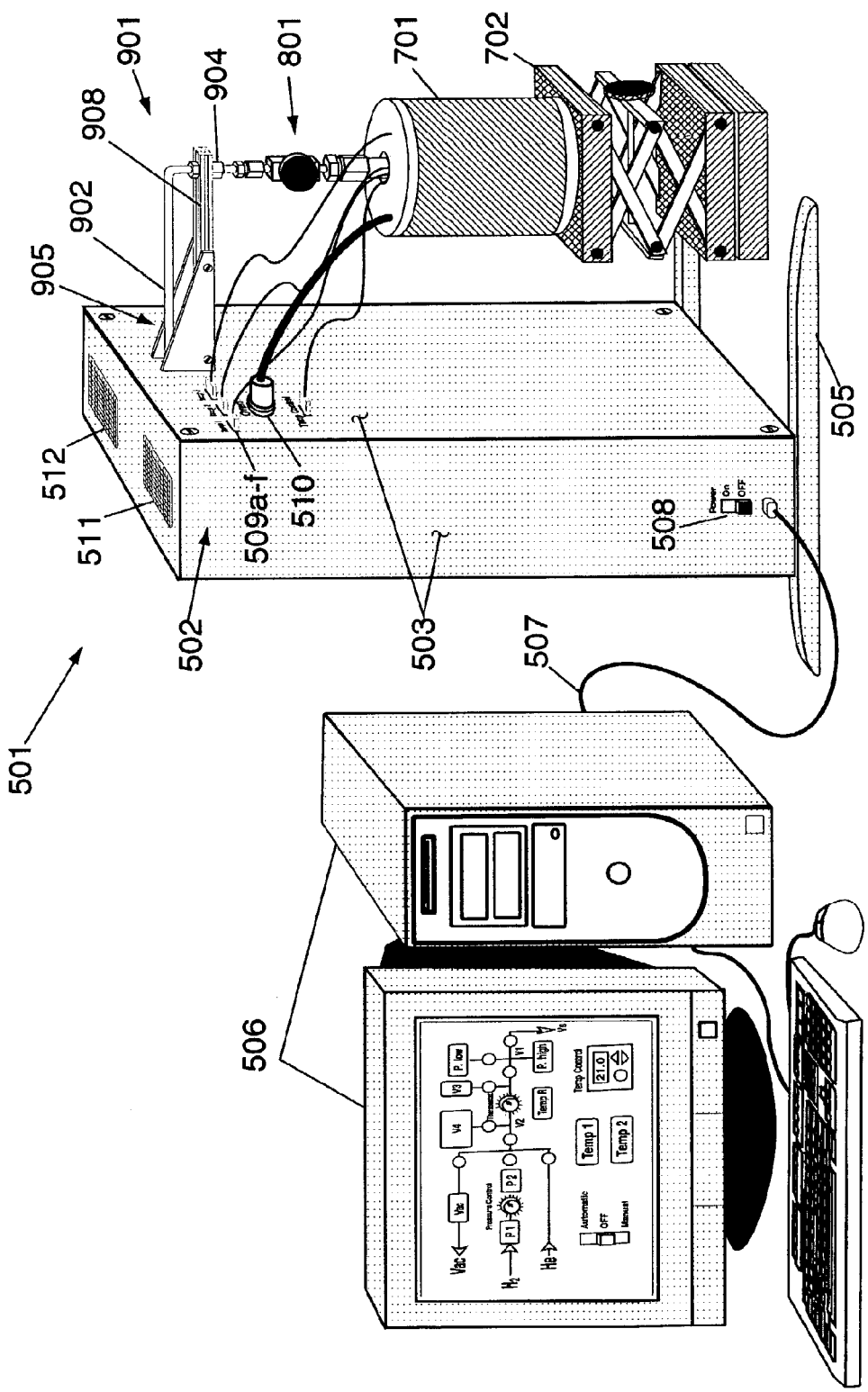
Figure 5D:
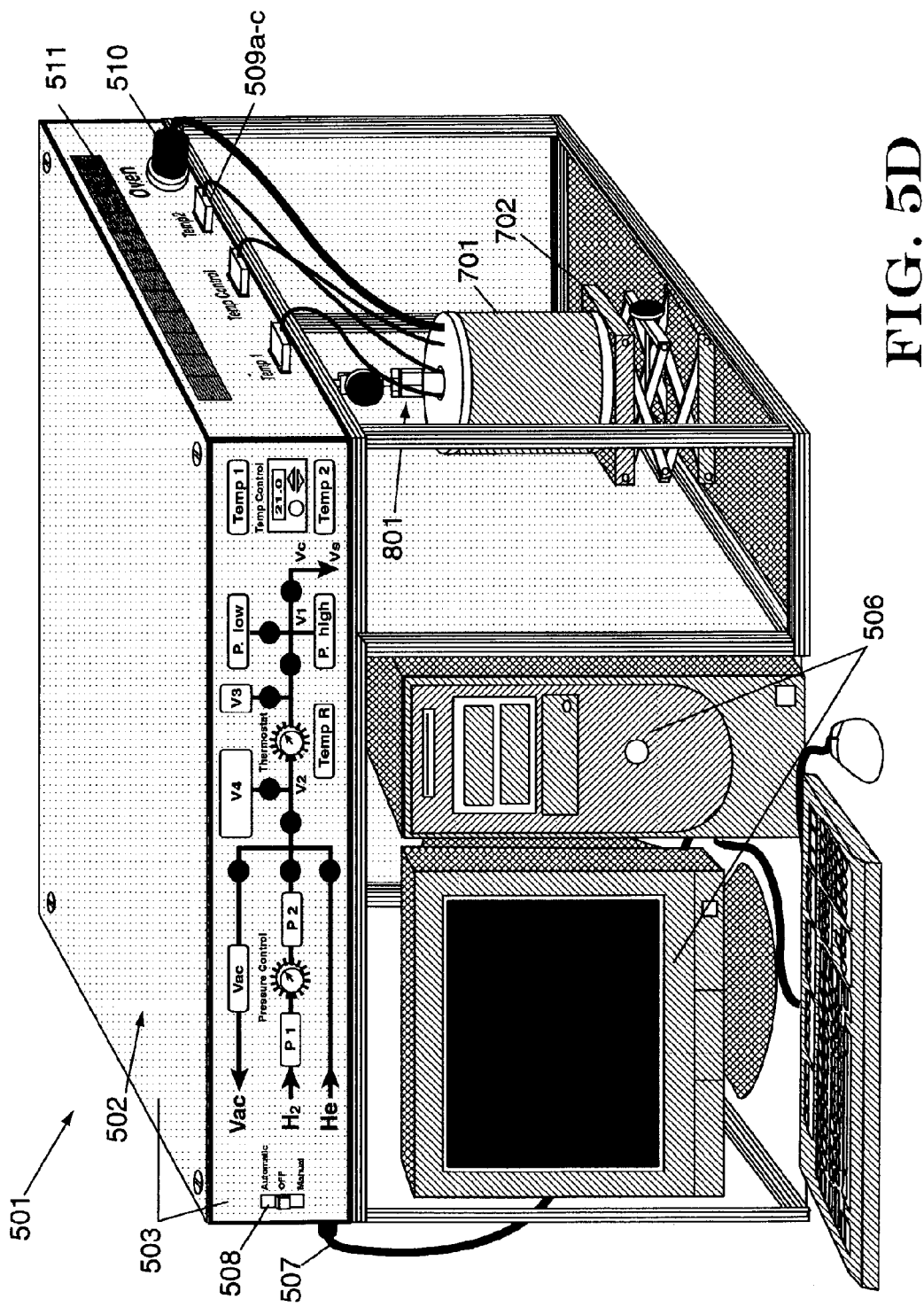

FIG. 5a is a perspective view of the exterior of a basic gas sorption/desorption analyzer embodying the present invention. FIG. 5b is a photograph of one embodiment of the invention. FIG. 5c and FIG. 5d are alternate embodiments of the same.

The gas sorption/desorption analyzer 501 is comprised of an enclosure, housing, body, box, or cabinet 502 that contains all of the internal gas handling lines, volumes, valves, sensors and control devices and an external gas handling portion 901 of the gas sorption/desorption analyzer 501. The internal parts are described below and shown in the schematic diagrams of FIGS. 6, 7 and 8. The gas sorption/desorption analyzer 501 has a set of feet or fixtures 505 used as a means to stand upright or may be fixed to a wall or frame. A computer or logical control device 506 controls the gas sorption/desorption analyzer 501. It is connected to the gas sorption/desorption analyzer 501 by a communication link 507 for example using an Ethernet line. A sample container, container, or vessel 801 is connected to the internal workings of the gas sorption/desorption analyzer 501 by the external gas handling portion 901. A sample container valve 805 isolates a sample 814 in the sample container 801 from the external gas handling portion 901. A thermocouple, thermistor or temperature measuring device 820 is inserted into a thermocouple well 815 that extends up through the center of the sample 814 that is inside of the sample container 801. A main power switch 508 is located on the exterior of the enclosure 502. Thermocouple or temperature measurement inputs 705, 706, 707 and sample heater (not shown) power supply plug or output 510 are located on the exterior of the enclosure 502. Vents or ventilation ports are located at the top of the enclosure 502. These include a vent for an electronics compartment 511 and a vent for a gas handling compartment 512.

Figure 6:
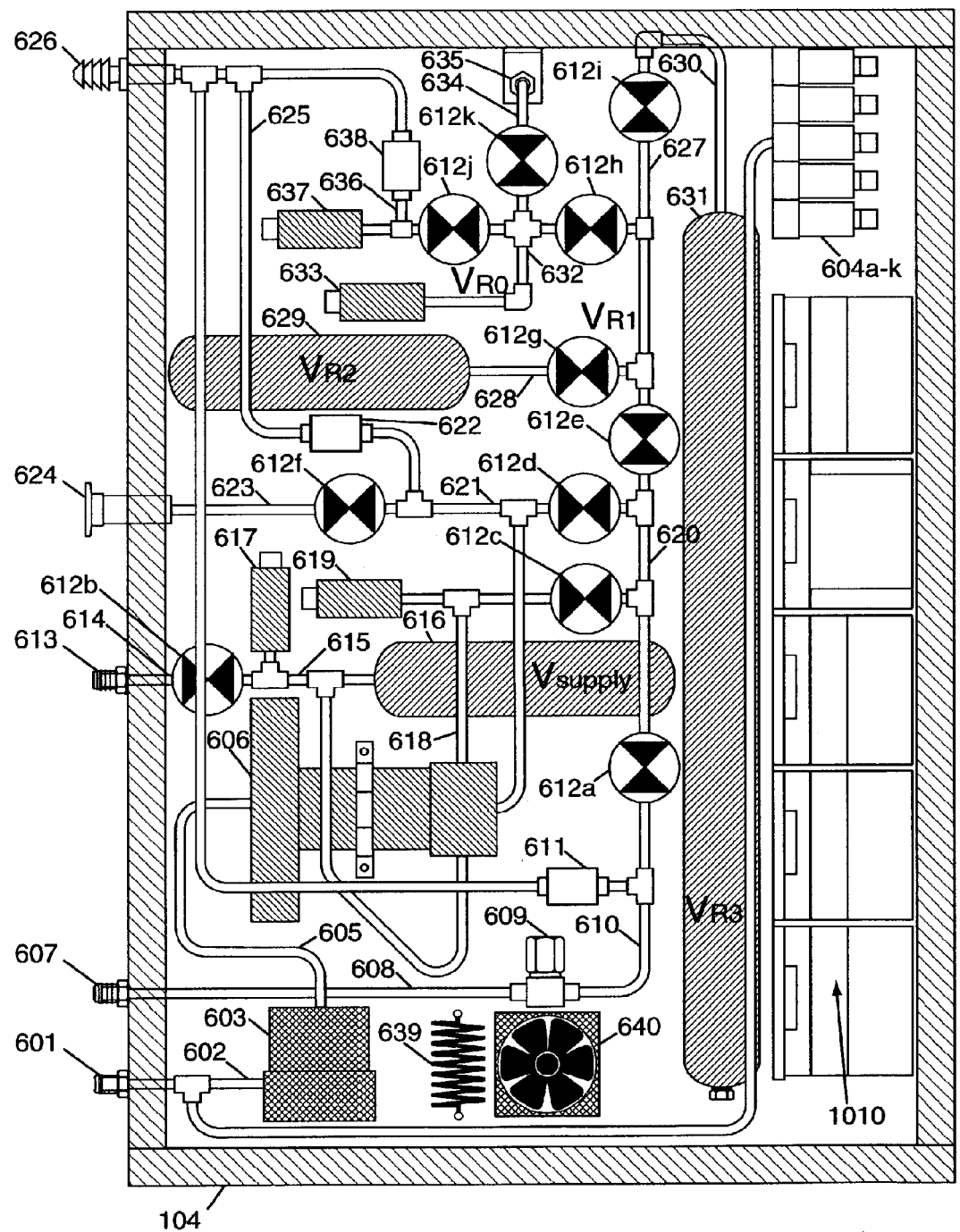
FIG. 6) is a schematic diagram showing an interior view of a portion of the apparatus (gas sorption/desorption analyzer) embodying the invention as viewed from the back-side.

FIG. 6 shows a schematic diagram of the interior parts and plumbing of the gas sorption/desorption analyzer 501 view from the back of the gas sorption/desorption analyzer.

Air Supply System

Indicated at 601 in FIG. 6 is a connector for attaching a source of pressurized air to the gas sorption/desorption analyzer 501. The air connector 601 is preferably a quick coupling but may be any connector rated for air service at least 20 atm. An air supply line 602 is connected from the air connector 601 to an air controller 603. According to the embodiment the air controller 603 is a PID (Proportional, Integral, and Derivative) electric-pneumatic controller. The air supply line 602 is also connected to a series of air controlled solenoids 604a-k. The output of the air controller 603 is connected via an variable air control line 605 to a gas pressure regulator 606. According to the embodiment the gas pressure regulator 606 is a pneumatically controlled pressure regulator capable of regulating hydrogen gas to a fixed pressure above 1 atm and below 200 atm.

Calibration Gas Supply System

Indicated at 607 in FIG. 6 is a connector for attaching a source of pressurized calibration gas to the gas sorption/desorption analyzer. The calibration gas connector 607 is preferably a metal gasket sealed coupling but may be any connector rated for gas service of at least 200 atm. In the preferred embodiment helium gas is used as the calibration gas, but the invention is not limited to this case. Other gases such as nitrogen or argon may also be used. A calibration gas supply line 608 is connected from the calibration gas connector 607 to a calibration gas check valve 609. The check valve 609 closes if the gas pressure on the outlet (right side) of the check valve is greater than the gas pressure on the inlet (left side) of the check valve. This helps to prevent gases other than the calibration gas from back-flowing to the source of the calibration gas. This is an important feature as it prevents contamination of the calibration gas with other gases.

A calibration gas line 610 is connected from the calibration gas check valve 609 to a calibration gas pressure relief valve 611. The calibration gas pressure relief valve 611 vents any gas that is in excess of the valve's set pressure which is usually 2 atm to 10 atm above the pressure of the supply pressure of the calibration gas. The calibration gas pressure relief valve 611 operates to prevent gases at higher pressures than the calibration gas from leaking through the calibration gas check valve 609 over time and causing damage to calibration gas lines, regulators or contamination of the calibration gas with other gases. The calibration gas line 610 is further connected from the calibration gas pressure relief valve 611 to an automated valve 612a. When the automated valve 612a is opened in response to an operating signal, the calibration gas is allowed to flow from the calibration gas source into the gas lines, vessels and components beyond 612a. The calibration gas is thus used to calibrate the volume of empty spaces in the gas lines, vessels, components and spaces surrounding the sample 814 to be measured.

Working Gas Supply System

In the preferred embodiment hydrogen gas is used as a working gas, but the invention is not limited to this case. Other working gases such as but not restricted to nitrogen, oxygen, ammonia, carbon dioxide, carbon monoxide, or hydrocarbons may also be used. Indicated at 613 in FIG. 6 is a connector for attaching an external source of the working gas to the gas sorption/desorption analyzer 501. The gas connector 613 is preferably a metal gasket sealed coupling but may be any connector rated for gas service of at least 200 atm. A gas line 614 is connected from the gas connector 613 to an automated valve 612b. A gas supply line 615 is connected from the automated valve 612b to a gas vessel or container 616. In the preferred embodiment, the gas vessel 616 comprises a 150 milliliter 316L stainless steel cylinder rated to operate at gas pressures of at least 200 atm. The gas supply line 615 is further connected to a supply gas pressure transducer 617 which is shown in FIG. 6 in a location on top of the gas vessel 616. In the preferred embodiment, the supply gas input pressure transducer 617 comprises strain-gauge or capacitance pressure measuring device with a range of 0 to 207 atm, but the invention is not limited to this type of pressure measuring device or this pressure range. The gas supply line 615 is further connected to an input on the gas pressure regulator 606. The inside region of the gas vessel 616, gas line 615, supply gas input pressure transducer 617, the automated valves 612b, and the gas pressure regulator 606, serves as a working gas storage, the volume of which is expressed by VS. The volume of VS is determined using common methods of volume calibration, for example by venting working gas at a known pressure from VS into an evacuated calibrated standard volume and measuring the resulting equilibrium pressure. When the automated valve 612b is opened in response to an operating signal, the working gas is allowed to flow from the external source of working gas into VS. Then the automated valve 612b is closed in response to an operating signal. The pressure of the working gas in VS is measured using pressure transducer 617. Thus VS is employed as a calibrated volume source of working gas that provides quantified allotments of working gas into the rest of the gas handling system. This restricted working gas supply volume serves several measuring and safety related purposes that are outlined in the process descriptions that follow.

A gas supply line 618 indicated in FIG. 6 is connected from an output on the gas pressure regulator 606 to a supply gas output pressure transducer 619. The supply gas output pressure transducer 619 measures the pressure of the working gas supplied to the rest of the gas handling system by the pressure regulator 606. In the preferred embodiment, the supply gas output pressure transducer 619 comprises strain-gauge or capacitance pressure measuring device with a range of 0 to 207 atm, but the invention is not limited to this type of pressure measuring device or this pressure range. The gas supply line 618 is further connected to an automated valve 612c. When the automated valve 612c is opened in response to an operating signal, the working gas is allowed to flow from the gas pressure regulator 606 into the rest of the gas handling system.

Working Gas, Calibration Gas, Residual Air Discharge System

A gas line 620 shown in FIG. 6 is connected from the automated valve 612c to the automated valve 612a. Together these two automated valves supply either working gas or calibration gas into the rest of the gas handling system. The gas line 620 is further connected to automated valves 612d and 612e. When the automated valve 612e is opened in response to an operating signal, working gas, calibration gas or residual air is allowed to flow to or from the rest of the gas handling system. When the automated valve 612d is opened in response to an operating signal, working gas, calibration gas or residual air is allowed to flow from the rest of the gas handling system to a discharge line 621. The discharge line 621 is connected from the automated valve 612d to a discharge pressure relief valve 622. The discharge pressure relief valve 622 is set to open and discharge working gas, calibration gas or residual air when the pressure in the discharge line 621 is greater than the pressure on the exhaust side of the discharge pressure relief valve 622 (usually 1 atm). The discharge line 621 is further connected to an automated valve 612f. When the automated valve 612f is opened in response to an operating signal, working gas, calibration gas or residual air is allowed to flow from the discharge line 621 to a vacuum line. The discharge line 621 is further connected to an exhaust port on the gas pressure regulator 606. The exhaust port on the gas pressure regulator 606 allows working gas to be discharge from the gas supply line 618 if the pressure in the gas supply line 618 is greater than the pressure setting of the gas pressure regulator 606. This allows the gas pressure regulator 606 to regulate the output pressure to a desired pressure regardless of whether the initial pressure in the gas supply line 618 is above or below the desired pressure. For example, if the desired pressure setting of the gas pressure regulator 606 is changed from 100 atm to 50 atm, the regulator adjusts the pressure in the gas supply line 618 from 100 atm to 50 atm by exhausting the excess working gas in the gas supply line 618 through the regulator exhaust port to the discharge line 621 and in this case out of the discharge pressure relief valve 622.

Vacuum System

A vacuum line 623 shown in FIG. 6 is connected from the automated valve 612f to a vacuum connector 624. In the preferred embodiment, the vacuum connector 624 is preferably a rubber gasket sealed vacuum coupling but may be any connector rated for vacuum service of at least 10 millitorr. An external vacuum line is connected from the vacuum connector 624 to an external vacuum pump (not shown). The discharge pressure relief valve 622 operates to prevent working gas, calibration gas or residual air at pressures greater than 1 atm from being discharged through the vacuum line 623, thereby avoiding needlessly overworking the external vacuum pump.

Vent System

A vent line 625 indicated in FIG. 6 is connects a vent connector 626 to the discharge pressure relief valve 622 and also to a calibration gas pressure relief valve 611. In the preferred embodiment the vent connector 626 is a hose-barb connector, but may be any connector rated for vacuum service or pressures of at least 2 atm. An external vent line is connected from the vent connector 626. The external vent line is generally connected to some kind of laboratory ventilation system. Such systems generally run just slightly sub-atmospheric.

Aliquot System

Indicated at 627 in FIG. 6 is a gas line connecting automated valves 612e, 612g, 612h and 612i. When the automated valve 612e is opened in response to an operating signal, gas, calibration gas or residual air is allowed to flow to or from the portion of gas handling system that provides a means to deliver aliquots of gas to or from the sample 814. The inside region of the gas line 627 and the automated valves 612e, 612g, 612h and 612i, serves as a gas storage, the volume of which is expressed by VR1.

A gas line 628 connects the automated valve 612g to a gas vessel 629. In the preferred embodiment, the gas vessel 629 comprises a 150 milliliter 316L stainless steel cylinder rated to operate at gas pressures of at least 200 atm. The inside region of the gas line 628, the gas vessel 629, and the automated valve 612g, serves as a gas storage, the volume of which is expressed by VR2.

A gas line 630 connects the automated valve 612i to gas vessels 631a and 631b. In FIG. 6 the gas vessel 631a is located on top of 631b. In the preferred embodiment, the gas vessels 631a and 631b are comprised of 500 milliliter 316 L stainless steel cylinders rated to operate at gas pressures of at least 200 atm. The inside region of the gas line 630, the gas vessels 631a and 631b, and the automated valve 612i, serves as a gas storage, the volume of which is expressed by VR3.

Indicated at 632 in FIG. 6 is a gas line connecting automated valves 612h, 612j, 612k and a high pressure transducer 633. The inside region of the gas line 632, the automated valves 612h, 612j, 612k, and the high pressure transducer 633, serves as a gas storage, the volume of which is expressed by VR0.

A gas line 634 connects the automated valve 612k to a gas connector 635. The gas connector 635, in turn connects the gas line 634 to the external gas handling portion 901 of FIG. 5, which in turn is connected to the sample container 801. The inside region of the automated valve 612k, the gas line 635, the gas connector 635, the external gas handling portion 901, and the sample container 801, serves as a gas volume surrounding the sample 814, the volume of which is expressed by VC.

The high pressure transducer 633 provides a means to measure the pressure of the gas in a given aliquot. When the automated valve 612k is open the high pressure transducer 633, also provides a means to measure the gas pressure surrounding the sample 814 either in equilibrium or during sorption or desorption. In the preferred embodiment, the high pressure transducer 633 comprises strain-gauge or capacitance pressure measuring device with a range of 0 to 207 atm, but the invention is not limited to this type of pressure measuring device or this pressure range.

Indicated at 636 in FIG. 6 is a gas line connecting the automated valve 612j to a low pressure transducer 637 and a low pressure transducer failsafe pressure relief valve 638. The low pressure transducer 637 provides a means to make more accurate measurements at pressures below 7 atm, than by using the high pressure transducer 633. The low pressure transducer 637 provides a means to measure the pressure of the gas in a given aliquot when the automated valve 612j is open. When the automated valve 612k is also open, the low pressure transducer 637, also provides a means to measure the gas pressure surrounding the sample 814 either in equilibrium or during sorption or desorption. In the preferred embodiment, the low pressure transducer 637 comprises strain-gauge or capacitance pressure measuring device with a range of 0 to 7 atm, but the invention is not limited to this type of pressure measuring device or this pressure range. The logical control system provides that the automated valve 612j can not open if the indicated pressure read on the high pressure transducer 633 is greater than 1 to 7 atm depending on the chosen setting. As a failsafe mechanism, should the gas line 636 be exposed to gas pressures greater than 7 atm the low pressure transducer failsafe pressure relief valve 638 will open and vent the gas to the vent line 625 to which it is connected. The transducer failsafe pressure relief valve 638 will close as soon as the gas pressure drops below 7 atm. This failsafe mechanism provides a means to protect the low pressure transducer 637 from pressures above 7 atm which might damage the transducer.

The volumes of gas storage volumes VC, VR0, VR1, VR2, and VR3 are determined using common methods of volume calibration, for example by venting gas at a known pressure from the gas storage volumes VC, VR0, VR1, VR2, or VR3 into an evacuated calibrated standard volume and then measuring the resulting equilibrium pressure using either the low-pressure transducer 637 or the high-pressure transducer 633. The gas storage volumes VR1, VR2, and VR3 can be employed separately or in different combinations together with the gas storage volume VR0 to provide quantified aliquots of gas to or from the sample 814.

The automated valves 612a-j are each two-position valves having an open position and a closed position. According to the preferred embodiment, the valves are pneumatic valves. When the pneumatic valve is opened in response to an operating signal, air flows there-into, holding the valve in the open position. The automated valves 612a-i are each normally closed valves and according to the preferred embodiment, the automated valve 612j is a normally open valve.

Piping constituting the lines and the vessels, etc. connected to the line are made preferably of stainless steel, and in particular 316l stainless steel for the prevention of corrosion or other degradation. The various gaskets, lines, fittings and valves provide a leak-free means to seal the gas portion inside of the gas sorption/desorption analyzer 501 from the exterior atmosphere.

Enclosure

The enclosure 502 provides a means of insulating the gas handling parts of the gas sorption/desorption analyzer 501 from changes in the ambient air temperature. The enclosure 502 is comprised of panels, a skin, or cover 503 and a frame, or support 504. The panels 503 are insulated by means of covering the interior surface with an insulating material such as spun glass or plastic foam. The enclosure 502 also protects the internal components from outside activities and acts as a safety barrier in the event of rupture of any of the internal components.

Enclosure Heater

The temperature of the enclosure 502 is maintained at a chosen level using an enclosure heating element 639 and an enclosure air re-circulating fan 640 as shown in FIG. 6. The enclosure air re-circulating fan 640 operates continuously, circulating air past the heating element 639, to maintain a constant temperature of and all of the components within the enclosure 502. The enclosure temperature is maintained at a constant level by adjusting power to the enclosure heating element 639 using PID control feed-back from a thermocouple located inside of the enclosure 502.

Figure 7:
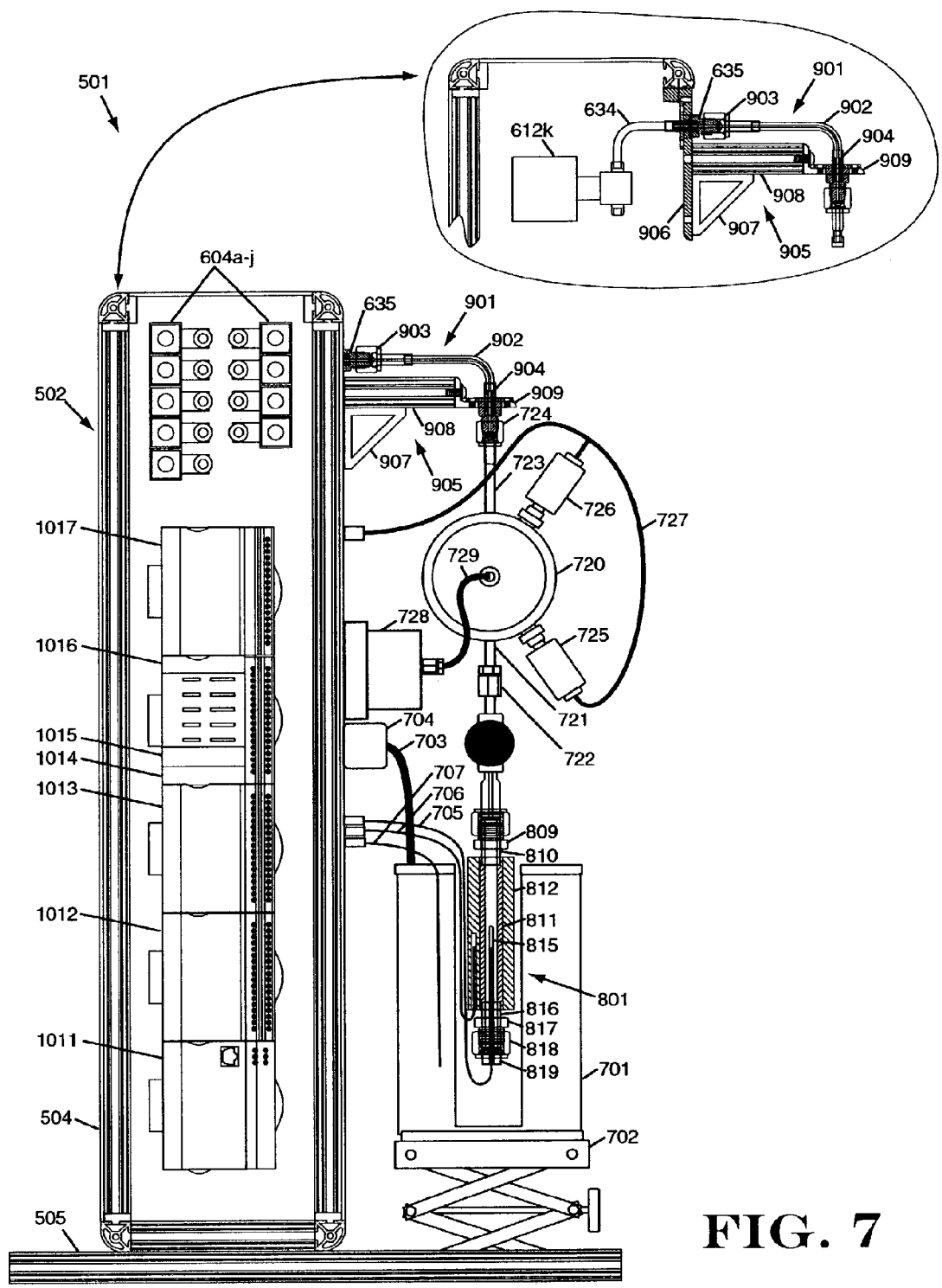
FIG. 7) is a schematic diagram showing an interior view and exterior cross-section of a portion of the apparatus (gas sorption/desorption analyzer) embodying the invention as viewed from the left-side.

FIG. 7 is a schematic diagram of the interior and part of the exterior of the gas sorption/desorption analyzer 501 view from the side of the gas sorption/desorption analyzer.

Sample Heater

Figure 10:
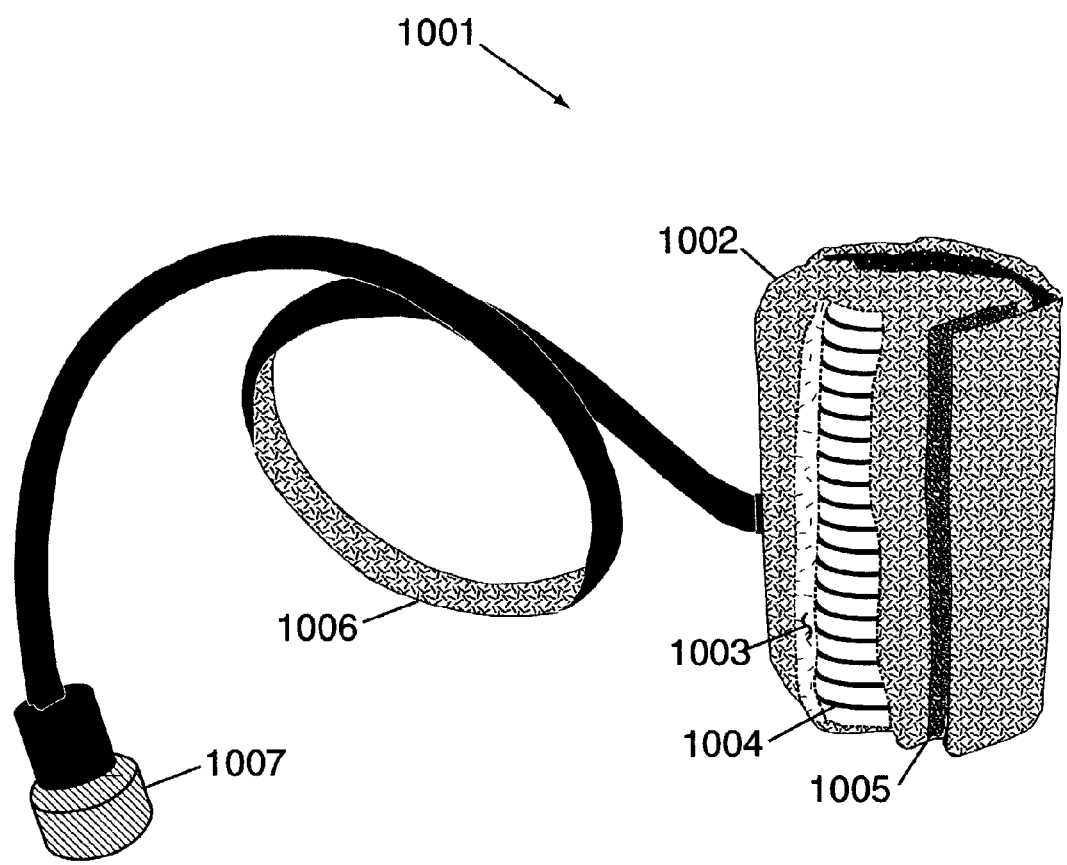
FIG. 10) is an illustration of a heating jacket embodying a portion of the invention for heating a sample in a sample container.

Indicated at 701 in FIG. 7 is a furnace used as a means of heating the sample container 801 and thus the sample 814. However, the means of heating the sample 814 is not limited to the types of heating described herein. In the preferred embodiment the furnace is replaced by a flexible heating jacket 1001 for heating the sample container for gas sorption and desorption of the sample 814 (shown in FIG. 8 and FIG. 10). The sample container 801 heating jacket 1001 shown in FIG. 10 comprises a resistive heating element 1004 that produces heat when passing a current. This is covered on the exterior by insulation 1003 to reduce heat loss and provide some protection for the operator from direct contact with the heating element 1004. The heating element 1004 and insulation 1003 are covered with a heat resistant fabric 1002. The heating jacket 1001 may be loosely fit around the sample container 801. The heating jacket 1001 is fixed in place by a fastener 1005 (generally of hook and loop type) that fixes one overlapping side of the jacket to the other side. Current to the heating element 1004 is supplied through a power cord 1006. At the end of the power cord 1006 is a power plug 1007. The power plug 1007 is preferably of a type that can not be plugged into a standard electrical wall socket to prevent accidental, uncontrolled heating of the heating jacket 1001.

Back-Pressure Regulator

A back-pressure regulator 720 shown in FIG. 7 is connected to the sample container 801 via a back-pressure regulator input gas line 721. The connection to the sample container 801 is made using a gas connector 722. The output on the back-pressure regulator 720 is connected to the external gas handling portion 901 via a back-pressure regulator output gas line 723 and a gas connector 724. The gas connectors 722 and 724 are preferably a metal gasket sealed couplings but may be any connector rated for gas service of at least 200 atm. The back-pressure regulator 720 serves to maintain a constant gas pressure in the sample container 801 during constant pressure desorption measurements. As gas is desorbed from the sample 814 it flows out of the sample container through the back-pressure regulator 720 and into the calibrated volumes of the gas sorption/desorption analyzer 501. The amount of gas desorbed can be determined by measuring the pressure increase in the chosen calibrated volume with either the high pressure transducer 633 (or the low pressure transducer 637 if the pressure is below 7 atm). PID control of the back-pressure regulator 720 is achieved using feed-back from a back-pressure regulator input pressure transducer 725 mounted on the sample container side of the back-pressure regulator 720. The back-pressure regulator input pressure transducer 725 sends an signal via pressure transducers power and signal wires 727 to a back-pressure regulator pneumatic PID controller 728. The back-pressure regulator pneumatic PID controller 728 adjusts the output air pressure that is sent via a back-pressure regulator air line 729 to the back-pressure regulator 720. In this manner the back-pressure regulator 720 adjusts the flow of gas out of the sample container 801 such that a constant pressure that is chosen is maintained in the sample container 801. A back-pressure regulator output pressure transducer 726 mounted on the output side of the back-pressure regulator 720 sends an signal via pressure transducers power and signal wires 727 to the computer 506 to record the output pressure.

For most other types of measurements the back-pressure regulator 720 is not needed. Therefore the back-pressure regulator 720 is removed and the sample container 801 is connected directly to the gas sorption/desorption analyzer 501 by connecting a valve top female nut 802 on the sample container 801 to an external bulkhead connector 904 on the external gas handling portion 901 of the gas sorption/desorption analyzer 501.

Sample Container

Figure 8:
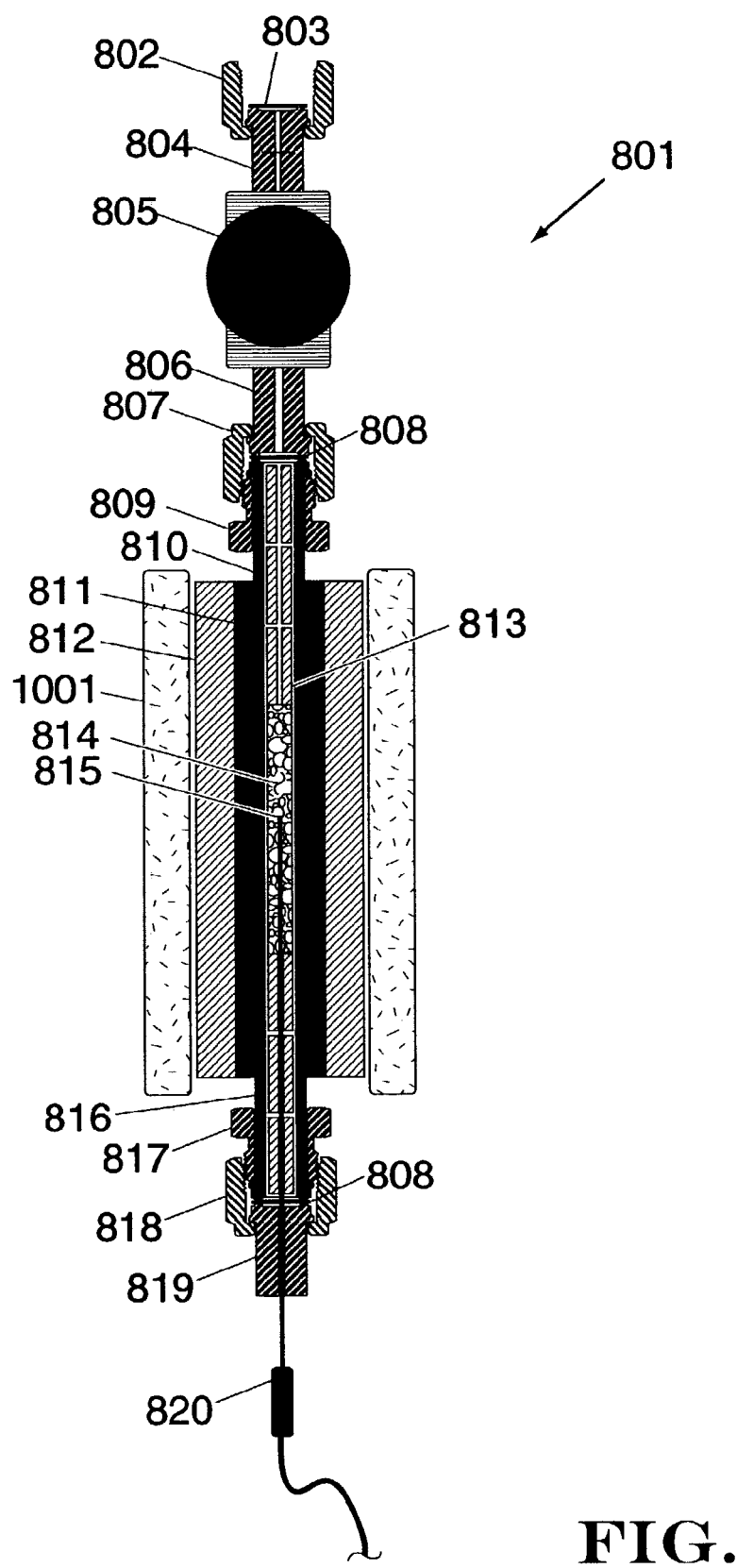
FIG. 8) is a cross-sectional diagram of a sample container embodying a portion of the invention.

The sample container 801 shown in FIG. 8 uses a valve top female nut 802, a valve copper gasket 803, and a valve top gland 804, to connect the sample container 801 to the gas sorption/desorption analyzer 501 at either the external bulkhead connector 904 or the back-pressure regulator connector 722 depending on whether a measurement requires the back-pressure regulator 720 or not. The sample container valve 805 to which the valve top gland 804 is connected, serves several purposes. First, it isolates the sample 814 from the external environment, most particularly air, if the sample 814 has been loaded into the sample container 801 in a special environment, for example in an argon glove box. Second, the sample container valve 805 isolates the sample 814 from the gas inside of the gas sorption/desorption analyzer 501 when the sample container 801 is connected to the gas sorption/desorption analyzer 501. This is necessary for purging the gas sorption/desorption analyzer 501 of residual air, or can be used if the sample 814 is under a gas pressure that will be released into the gas lines of the gas sorption/desorption analyzer 501. The sample container valve 805 is connected via a valve bottom gland 806, to a sample container top gland 810 using a valve bottom female nut 807, and sample container copper gasket 808 and a sample container top male nut 809. In the preferred embodiment, the gaskets 803 and 808 are comprised of copper, but may also be made of steel or other materials. The sample container top gland 810 is welded into a sample container body piece 811 comprised of steel. In the preferred embodiment, the sample container body piece 811 is comprised of but not limited to 316 L stainless steel with a wall thickness great enough to withstand hydrogen pressures of more than 200 atm when heated up to 400.degree. C. without sustaining significant material degradation. The sample container body piece 811, is encased by a sample container conductive jacket 812. In the preferred embodiment, sample container conductive jacket 812 is comprised of but not limited to aluminum or copper for good heat conduction. The sample container conductive jacket 812 is fit tightly to the sample container body piece 811 to provide a means of good thermal conductivity and equalize the temperature distribution within the sample container body piece 811. The empty space inside of the sample container body piece 811 that remains after the sample container 801 has been loaded with a sample 814, is taken up by sample container spacers 813. This reduces the empty volume of the sample container 801 which improves the accuracy of the measurements. A thermocouple well 815 runs up the center of the sample container body piece 811. A sample container bottom gland 816 is welded into the bottom portion of the sample container body piece 811. The bottom portion of the sample container body piece 811 is sealed with a sample container bottom plug 819 using a sample container bottom male nut 817, a sample container bottom female nut 818, and a sample container copper gasket 808. The thermocouple well 815 is welded into the sample container bottom plug 819 providing access into the center of the sample container body piece 811 while allowing the inside portion of the sample container 801 to be sealed from the exterior atmosphere. A sample thermocouple 820 is inserted into the thermocouple well 815 which runs up into and is partially surrounded by the sample 814. This enables more accurate measurements of the temperature of the sample 814 than using external thermocouples.

External Gas Handling Portion

Figure 9:
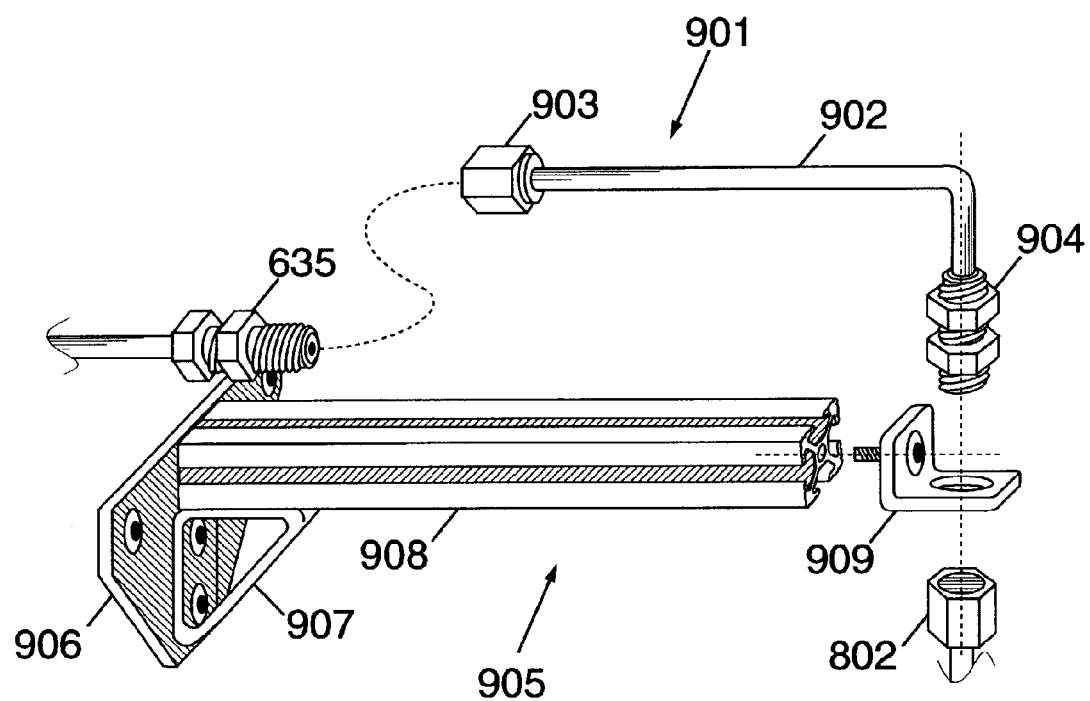
FIG. 9) is an illustration of an external gas handling portion of the invention.

The external gas handling portion 901 shown in FIG. 9 comprises an external gas line 902 that connects the gas connector 635 via an external female connector 903, to an external bulkhead connector 904 to which either the sample container 801 or back-pressure regulator 720 may be connected. The external gas handling portion 901 is supported by a supporting arm 905 that is comprised of a mounting bracket 906 to which is attached an angle bracket 907 and a extension bracket 908. The external bulkhead connector 904 is mounted to the supporting arm 905 using a connector bracket 909.

Alternative Sample Heater

With regard to FIG. 7 a means of heating the sample container 801 will be referred to as a furnace. The furnace 701 is sitting on a jack-stand 702. The jack-stand 702 provides a means to adjust the position of the furnace 701 with respect to the sample container 801 so as to optimize the heating of the sample 814. The furnace 701 is powered by a furnace power cord 703. At the end of the furnace power cord 703 there is a furnace power plug 704. The furnace power plug 704 is plugged into the sample heater power supply plug 510. The power to the furnace 701 is controlled by a furnace relay 1106 which opens and closes the electrical power circuit to the furnace 701. The furnace relay is controlled by the computer 506 via the data acquisition and control system 1101. The temperature of the sample 814 is measured using a thermocouple placed inside of the thermocouple well 810 which extends up into the sample 814. The thermocouple can be jacketed probe type 820 as shown in FIG. 5 and FIG. 8 or simply a bimetal wire type thermocouple 705 as shown in FIG. 7. PID control of the furnace 701 can be regulated using feed-back from the thermocouple 705 in the thermocouple well 810, or a thermocouple 706 attached to the sample container 801, or a thermocouple 707 located within the furnace 701.

Data Acquisition and Gas Sorption/Desorption Analyzer Control

Figure 11:
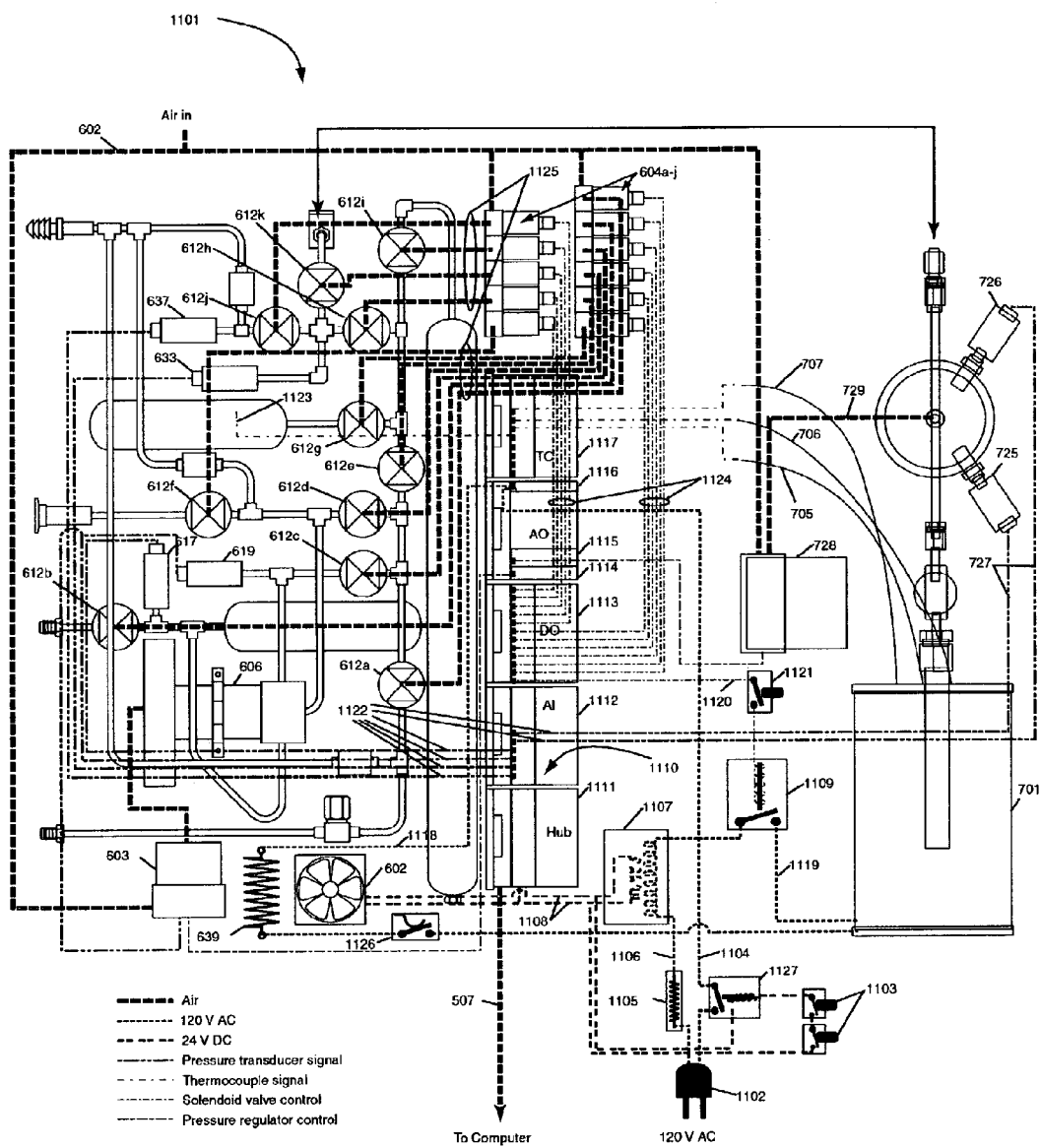
FIG. 11) is a schematic diagram of a data acquisition, control and safety system embodying a portion of the invention as viewed from the back-side.

The heart of the gas sorption/desorption analyzer 501 is a an electrical system 1101 shown in FIG. 11. The entire electrical system is powered at 110V AC from a standard wall outlet into which is plugged a gas sorption/desorption analyzer power plug 1102. While the preferred embodiment specifies 110 V AC 60 hertz operation other voltages and frequencies may also be used such as 220 V AC and 50 hertz. The gas sorption/desorption analyzer power plug 1102 is connected via an enclosure power safety switch 1103 to a 110 V AC power in 1104 line and via a 110 V AC fuse 1105 to a 110 V AC power out 1106 line. The enclosure power safety switches 1103 shut off power to the gas sorption/desorption analyzer 501 by opening the 24 V DC circuit of the power safety relay 1127 if any of the enclosure panels 503 are removed. The enclosure power safety switch 1103 may represent a multitude of enclosure power safety switches, each on a different panel 503. A 110 V AC to 24 V DC transformer 1107 converts the 110 V AC input voltage to 24 V DC to run the data acquisition and control system 1110 as well as the enclosure air circulating fan 640 via 24 V DC power lines 1108. The 110 V AC power in 1104 line also goes to a sample heater control relay 1109. The data acquisition and control system 1110 is comprised of a communications control hub 1111, a analog input device 1112, a digital output device 1113, a pressure regulator analog output device 1114, a back-pressure regulator analog output device 1115, an enclosure heating element 110 V AC analog output device 1116, and a thermocouple input device 1117. The communications control hub 1111 relays information to and from these devices to and from the computer 506 via the communication link 507. The enclosure heating element 639 receives power via an enclosure heating element 110 V AC line 1118 from the enclosure heating element 110 V AC analog output device 1116. The enclosure heater safety switch 641 shuts off power to the enclosure heating element 639 if the temperature in the enclosure 502 rises above a certain level. The sample heater control relay 1109 supplies power via a sample heater 110 V AC line 1119 to the sample heater 1001 or 701. The sample heater control relay 1109 is turned on or off via a sample heater relay control line 1120 by a signal from the computer 506 to the digital output device 1109. There is a sample heater safety shield switch 1121 on the sample heater relay control line 1120 to shut off power to the sample heater 1001 or 701 if a sample container safety shield 1201 has been opened. Pressure measurements from the pressure transducers 617, 619, 633, 637, 725, and 726 are transmitted via pressure transducer output lines 1122 to the analog input device 1112 and from there to the computer 506. Pressure measurements from the pressure transducers 619 is also transmitted directly to the air controller 603 to provide feed-back to the gas pressure regulator 606. An enclosure thermocouple 1123 is used to measure the temperature inside of the enclosure. This and measurements from the sample thermocouples 705 or 820, sample container thermocouple 706, and furnace thermocouple 707 are transmitted via the thermocouple input device 1117 to the computer 506. The air control solenoids 604a-j are opened or closed by electrical power supplied via air solenoids control lines 1124 from the digital output device 1113 on command from the computer 506. The automated valves 612a-j are like-wise controlled via pneumatic valves air control lines 1125 by air delivered from the air supply line 602 that passes through the air control solenoids 604a-j that have been opened.

Sample Container Safety Shield

Figure 12:
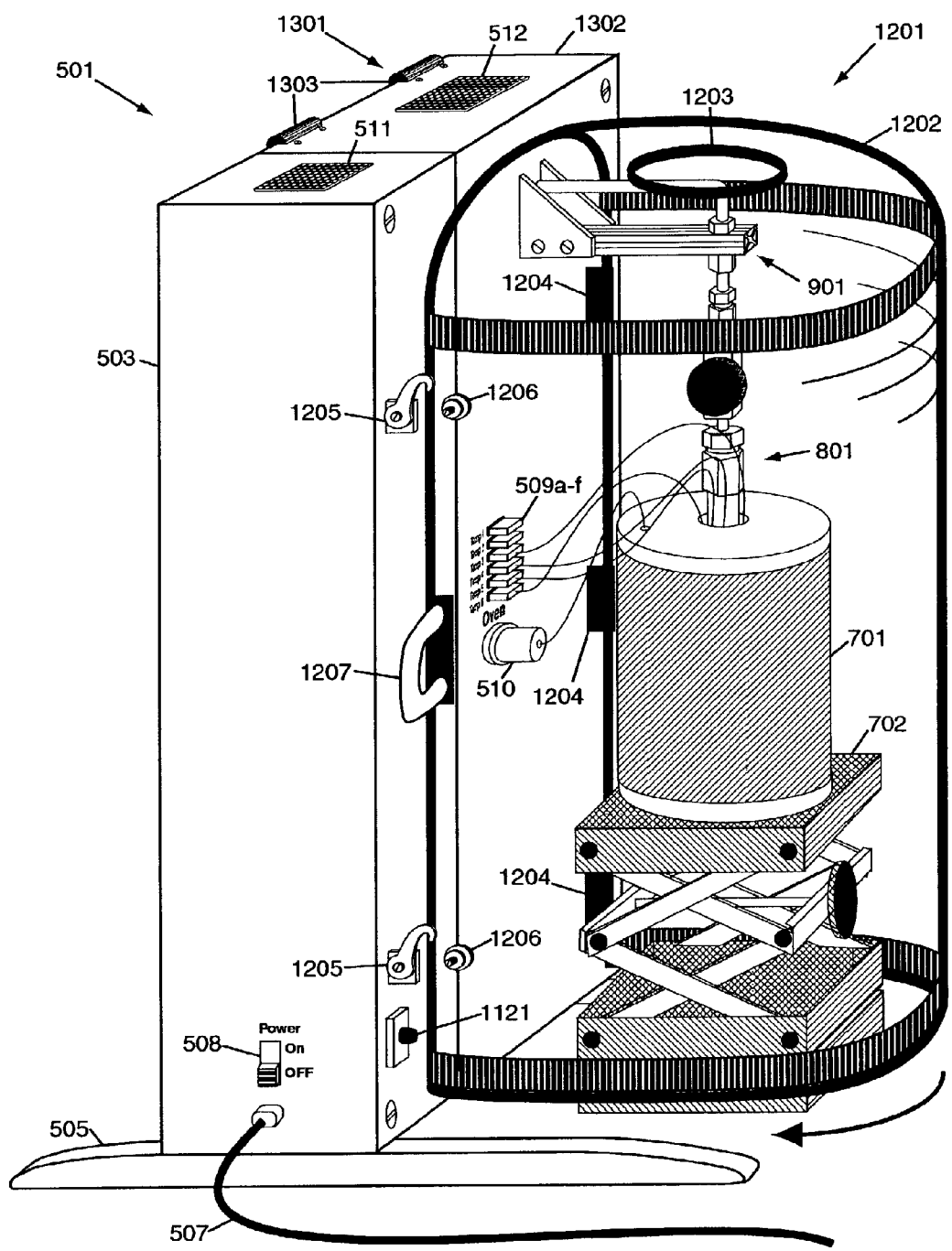
FIG. 12) is an illustration of a sample container safety shield attached to the apparatus (gas sorption/desorption analyzer) embodying a portion of the invention.

One safety aspect of the gas sorption/desorption analyzer 501 is the use of sample container safety shield 1201 shown in FIG. 12. The sample container safety shield 1201 is comprised of a see-through safety shield 1202 made of a see-through material such as plastic and a material able to substantially protect against flying objects in case of failure of the sample container 801, external gas handling portion 901, or components of or affixed to the back-pressure regulator 720. The see-through safety shield 1202 has a vent hole 1203 at the top to prevent the build-up of hydrogen gas and to allow heat from the furnace 701 to escape. The sample container safety shield 1201 is attached to the gas sorption/desorption analyzer 501 by means of a fastener such as a set of safety shield hinges 1204. These allow the sample container safety shield 1201 to be moved (swung) out of the way when setting the sample container 801, furnace 701, and jack-stand 702 up to make a measurement. During a measurement the sample container safety shield 1201 is held in a protective position (closed) by one or more latches. In the preferred embodiment, the latches are comprised of a set of safety shield latch hooks 1205 and safety shield latch pins 1206 which fasten the opening side of the sample container safety shield 1201 to the gas sorption/desorption analyzer 501. The sample container safety shield 1201 may be swung open and closed using a safety shield handle 1207 attached to the see-through safety shield 1202. The sample heater safety shield switch 1121 is attached to the front of the gas sorption/desorption analyzer 501 in such a way that it is in a closed circuit condition only when the sample container safety shield 1201 is latched shut. The sample heater safety shield switch 1121 is on the circuit which controls the furnace 701 (or heating jacket 1001). This safety feature prevents the furnace 701 (or heating jacket 1001) from operating if the sample container safety shield 1201 is not latched shut.

Failsafe Top Panel

Figure 13:
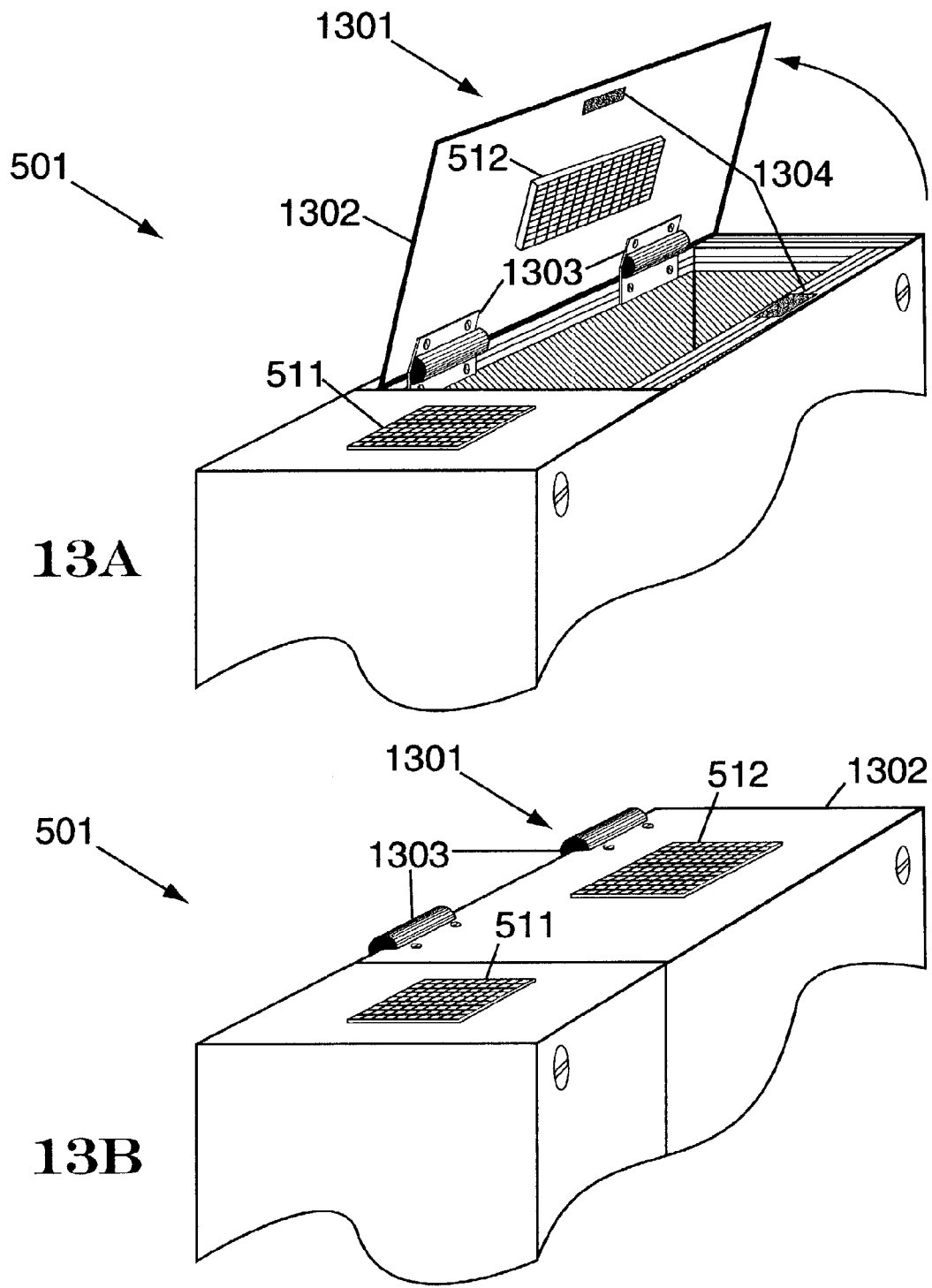
FIG. 13a) is an illustration of a failsafe top panel of the apparatus (gas sorption/desorption analyzer) embodying a portion of the invention, shown in the open position.
FIG. 13b) is an illustration of a failsafe top panel of the apparatus (gas sorption/desorption analyzer) embodying a portion of the invention, shown in the closed position.

Another safety aspect of the gas sorption/desorption analyzer 501 is a failsafe top panel 1301 shown in FIGS. 13A and 13B. The failsafe top panel 1301 is comprised of a gas handling compartment top panel 1302 that is attached to the gas sorption/desorption analyzer 501 by means of a fastener such as a set of safety shield hinges 1204. The other side of the gas handling compartment top panel 1302 is weakly attached to the gas sorption/desorption analyzer 501 by means of a top panel weak fastener 1304. In the preferred embodiment this fastener is comprised of two pieces of material one with hooks and the other with loops. These are attached to the gas handling compartment top panel 1302 and the frame 504 of the gas sorption/desorption analyzer 501. The vent for a gas handling compartment 512 is mounted into gas handling compartment top panel 1302. In the event that there is a rapid build up of pressure inside of the gas sorption/desorption analyzer 501, either by a release of pressurized gas or as a result of combustion, the gas handling compartment top panel 1302 will pop open and swing out of the way to release the pressure in a safe manner.

Automated Sample Container Valve System

Figure 14:
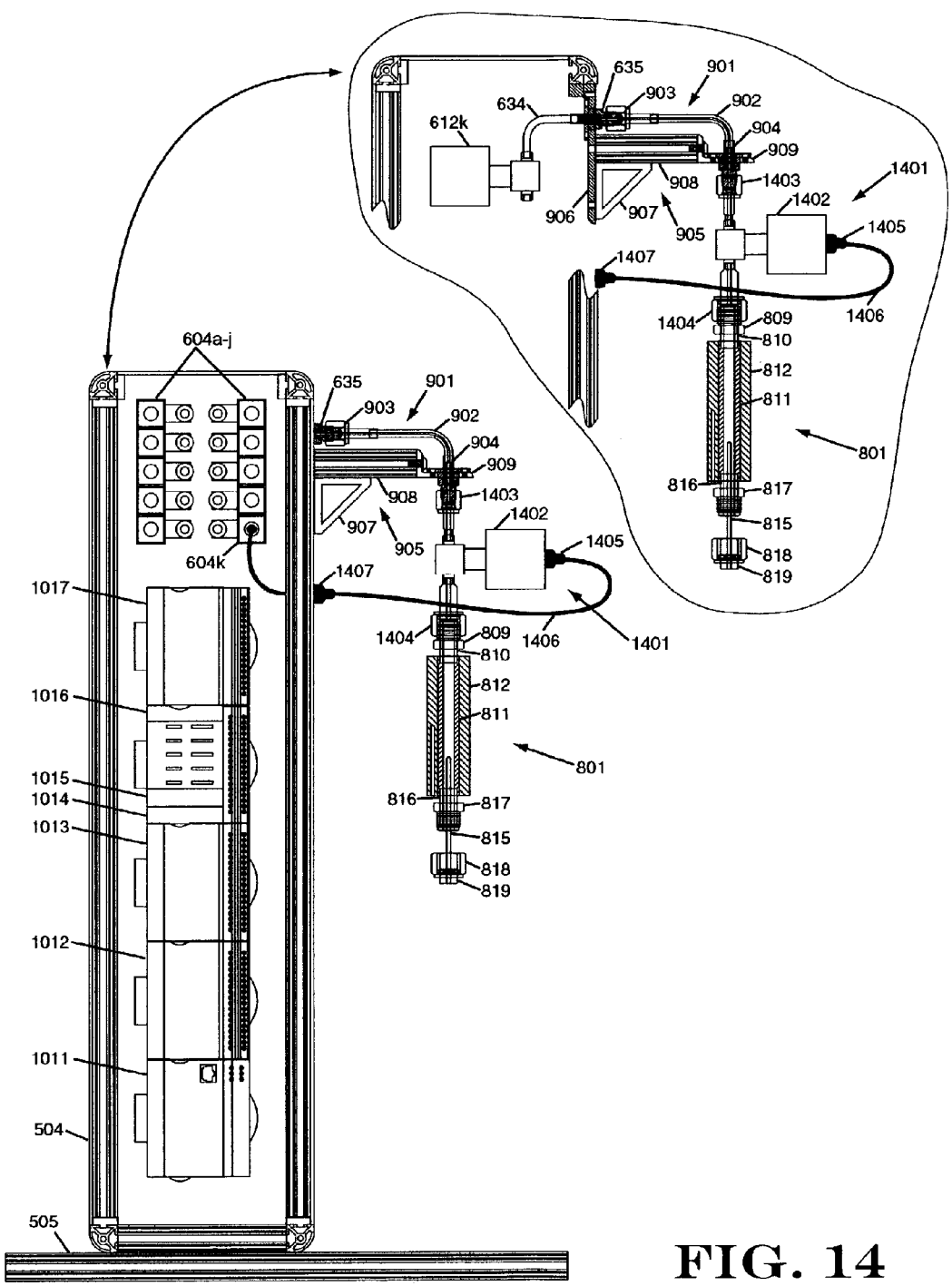
FIG. 14) is a schematic diagram of an alternative embodiment of the invention comprising the apparatus (gas sorption/desorption analyzer) of the invention and an automated sample container valve.

In an alternative embodiment shown in FIG. 14 the sample container valve 805 is replaced by an automated sample container valve system 1401. The automated sample container valve system 1401 is comprised of an automated sample container valve 1402 that is connected to the external gas handling portion 905 of the gas sorption/desorption analyzer 501 by a valve top connector 1403. The sample container valve 1402 is connected to the sample container 801 via a valve bottom connector 1404. The automated sample container valve system 1401 and sample container 801 may be removed as a unit to be loaded with a sample in an airless glove box and then re-connected to the external gas handling portion 905 of the gas sorption/desorption analyzer 501 to make a measurement. The automated sample container valve 1402 is a normally closed valve so that sample transfers can be performed without exposing the sample 814 to air. In the preferred version of this alternative embodiment, the automated sample container valve 1402 is a pneumatic valve. Supply air to control the valve comes from an additional air control solenoid 604k that is controlled via the data acquisition, control and safety system 1101 by the computer 506. Air to control the automated sample container valve 1402 passes from the additional air control solenoid 604k through an automated sample container valve connector 1407 on the outside of the gas sorption/desorption analyzer 501, through an automated sample container valve air line 1406 to an automated sample container valve air connector 1405 on the automated sample container valve 1402. The automated sample container valve air connector 1405 is disconnected when the automated sample container valve system 1401 and sample container 801 are removed for loading.

METHODS

The following is illustrative of the operation of the invention for measuring gas sorption properties of materials.

Figure 4:
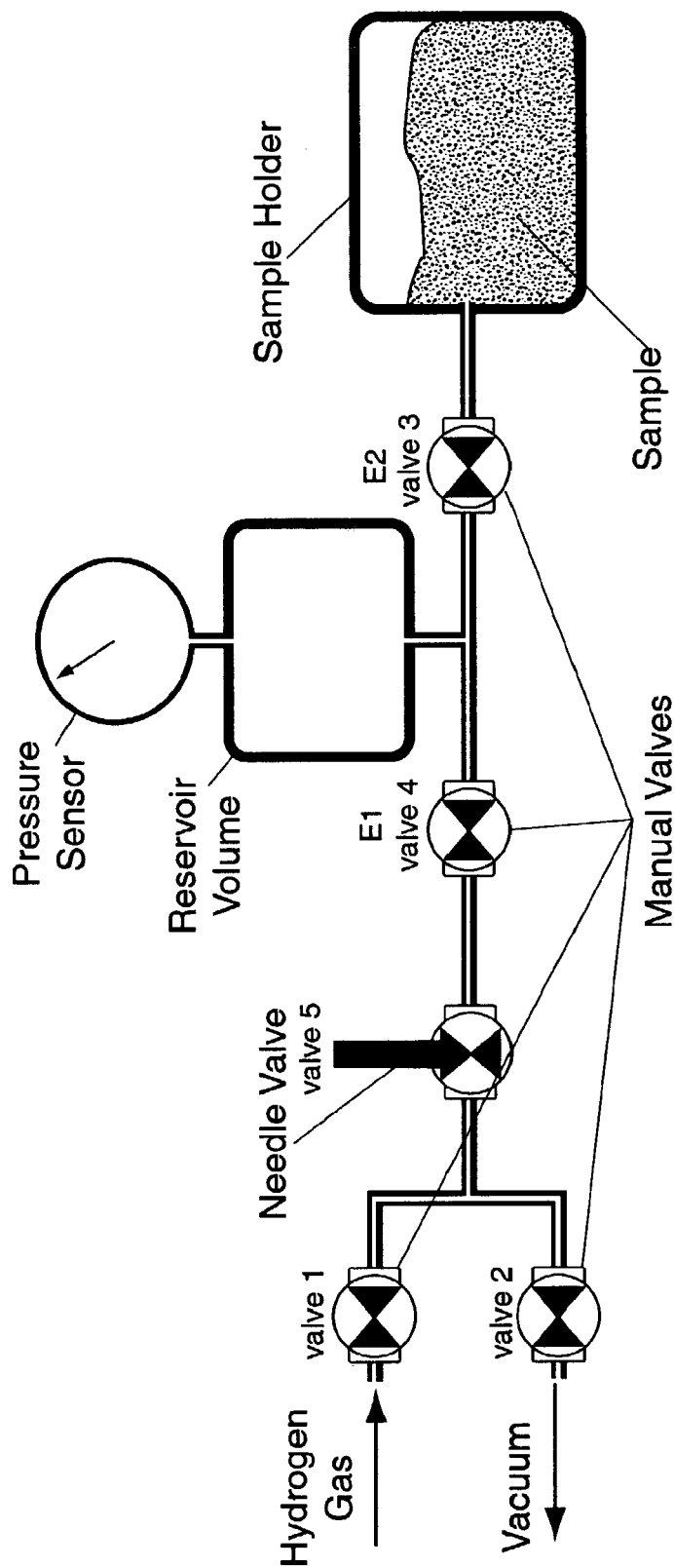
FIG. 4) is a schematic diagram of a conventional Sieverts type volumetric measuring device.
Figure 15:
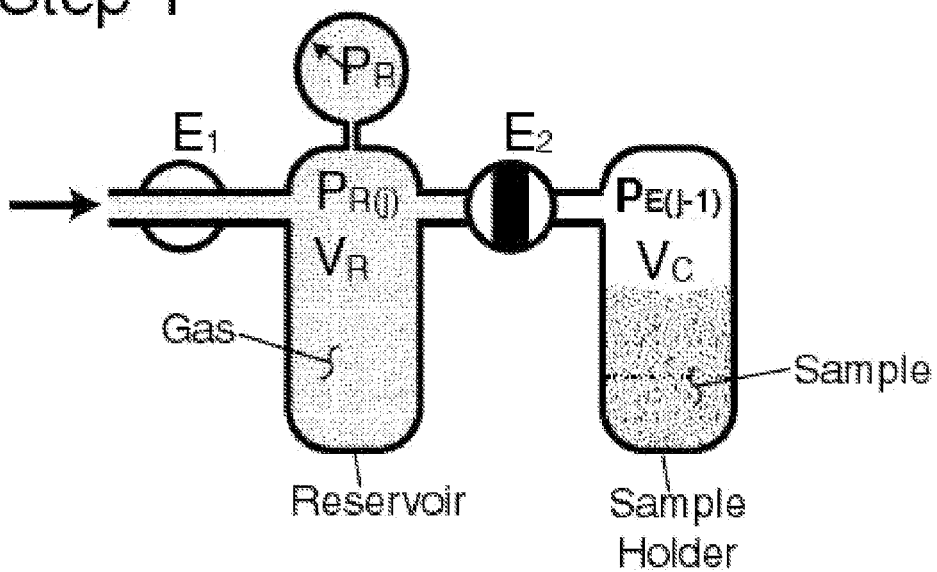
FIG. 15) is a diagram showing the open or closed states of valves involved in gas sorption measurements, a) Step 1 illustrates filling of a calibrated reservoir volume, b) Step 2 illustrates gas sorption to an equilibrium state.
Figure 15:
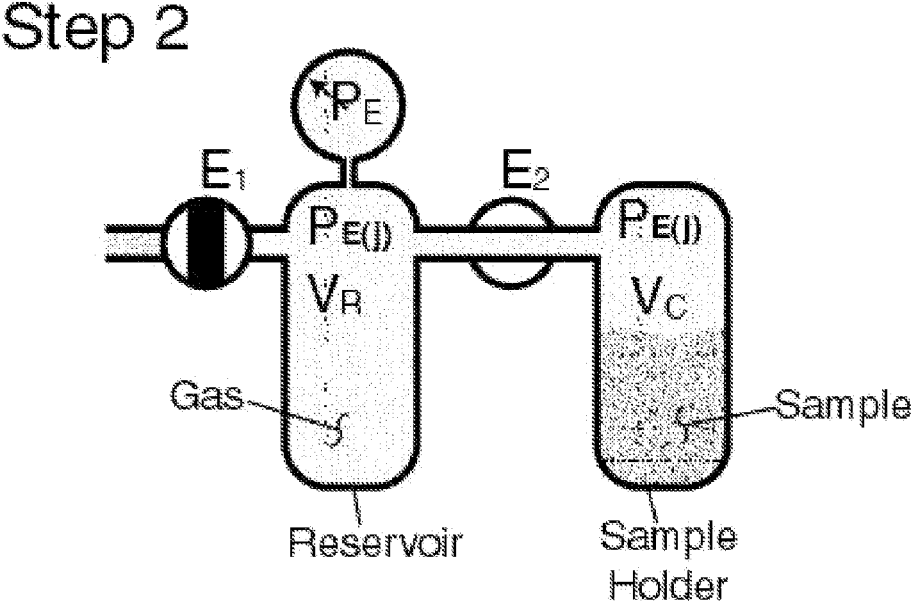
Figure 16:
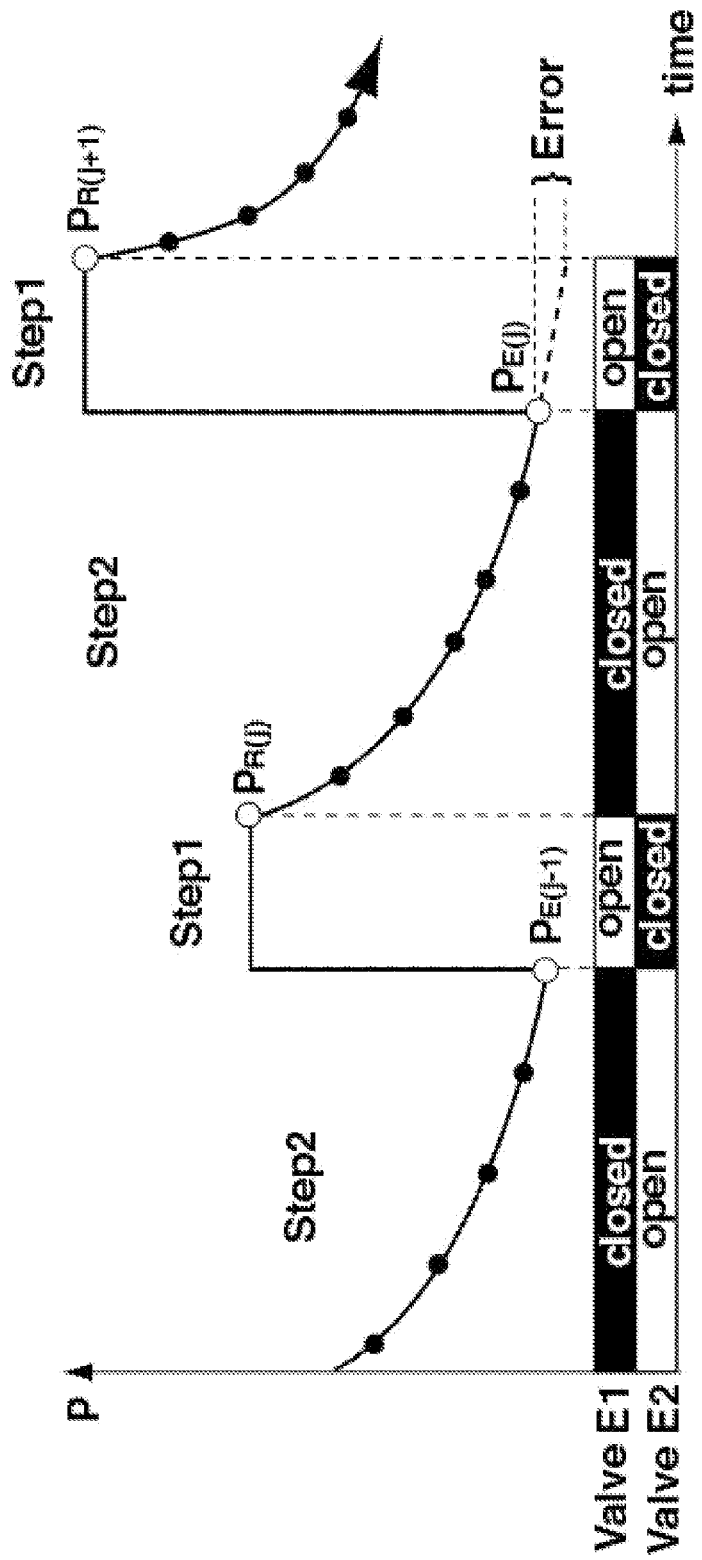
FIG. 16) is a schematic representation showing the opening or closing of valves and pressure changes with time during gas sorption measurements.

Sorption Concentration Measurement: The process of volumetrically measuring the concentration (or quantity, or capacity) of a gas adsorbed or absorbed by a sample is shown in the schematic diagrams of FIG. 15 and FIG. 16. As FIG. 15 illustrates, the measurement of one point (j FIG. 16) on a PCT plot proceeded in two steps. The valves E1 and E2 in FIG. 15 and FIG. 16 represent valve 4 and valve 5 respectively in the simple volumetric apparatus shown schematically in FIG. 4. In the schematic diagram of the preferred embodiment of the present invention FIG. 6, valves E1 (of FIG. 15 and FIG. 16) is representative of the automated valve 612h (or 612e if 612h and none, one, or both of 612g and 612i are open) and E2 is representative of the automated valve 612k. The method of sorption concentration proceeds as follows: First, valve E2 is closed. Following this, valve E1 is opened and the calibrated reservoir volume $V_R$ is filled with gas by opening valve 1 (valve 612c in FIG. 6). In the second step valve E1 is closed and the aliquot pressure $P_{Rj}$ in the calibrated reservoir volume $V_R$ is recorded using pressure transducer 633 or 637 if the pressure is below the maximum reading pressure of 637 and valve 612j is open. Following this, valve E2 is opened and the pressure in the sample container (and gas lines) $V_C$ and the reservoir volume $V_R$ due to sorption is recorded and continues to be recorded at specified time intervals. Again, the pressure is measured using pressure transducer 633 or 637 if the pressure is below the maximum reading pressure of 637 and valve 612j is open. This pressure change measurement provides a means to evaluate the amount of gas sorption from the aliquot of gas. The quantity of gas ad/absorbed at each step $N_j$ is given by:

$$N_j = \frac{1}{RT}\sum_j (P_{Rj}V_R + P_{j-1}V_C - P_j(V_R + V_C)) \quad \text{EQ. 1}$$

where $V_R$ is the reservoir volume ($V_0$, $V_1$, $V_2$, and/or $V_3$ in FIG. 6), $V_C$ is the sample container volume, $P_{Rj}$ is the pressure measured in the reservoir volume $V_R$ at step j, $P_j$ is the pressure measured in the combined volumes $V_R$ and $V_C$ at step j (at any time, and multiple times while valve E2 open), R is the universal gas constant, and T is the average gas temperature. When the change in pressure finally slows to a specified limit, this pressure reading $P_j$ is taken as the equilibrium pressure $P_{Ej}$ and the calculated quantity of gas ad/absorbed $N_j$ corresponding to the equilibrium pressure is taken as the equilibrium concentration $N_{Ej}$ ad/absorbed in that aliquot. For PCT measurements the process is repeated.

Two important considerations in making these measurements are: 1) that the length of time allowed between each aliquot should be sufficiently long so that the system has reached true equilibrium and, 2) that valve E2 is closed only for a short period of time to fill the reservoir, so that $P_{j-1}$ correctly represents the initial state of the sample at the beginning of each new aliquot of gas. This is demonstrated in FIG. 16.

Figure 17:
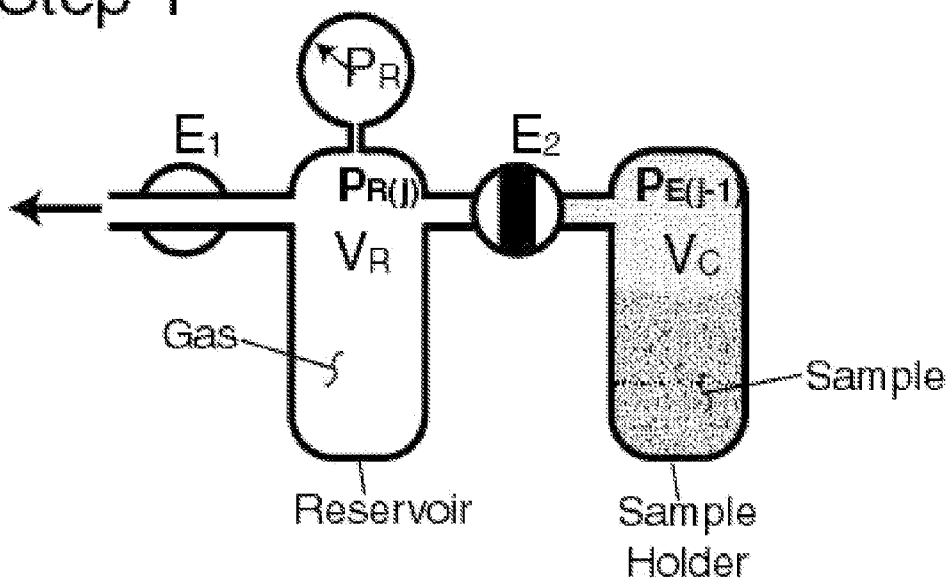
FIG. 17) is a diagram showing the open or closed states of valves involved in gas desorption measurements, a) Step 1 illustrates filling of a calibrated reservoir volume, b) Step 2 illustrates gas desorption to an equilibrium state.
Figure 17:
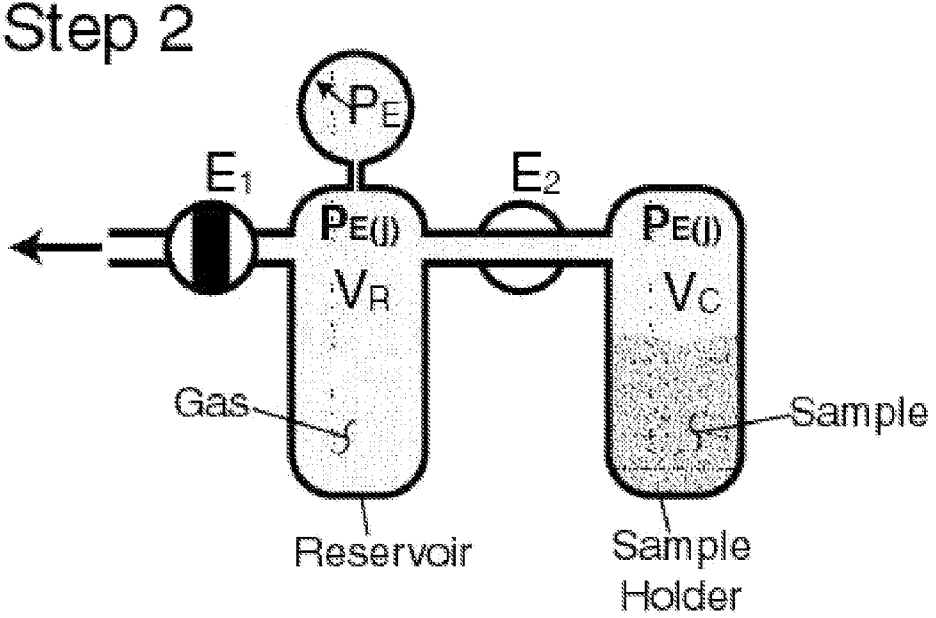
Figure 18:
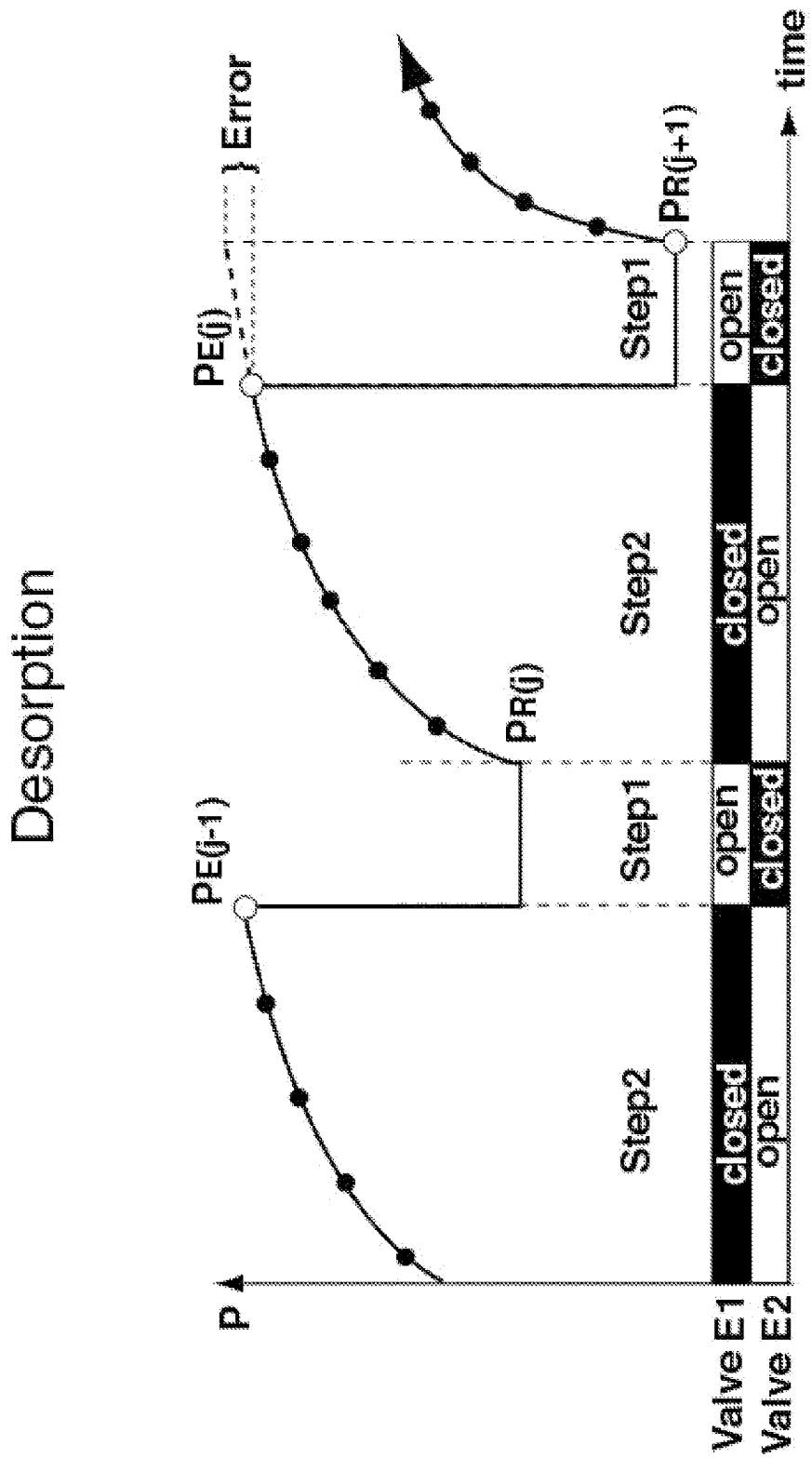
FIG. 18) is a schematic representation showing the opening or closing of valves and pressure changes with time during gas desorption measurements.

Desorption Concentration Measurement: The process of volumetrically measuring the concentration (or quantity, or capacity) of a gas desorbed by a sample is similar to the sorption process described above. This is shown in the schematic diagrams of FIG. 17 and FIG. 18. As FIG. 17 illustrates, the measurement of one point (j in FIG. 18) on a PCT plot proceeded in two steps. The valves E1 and E2 in FIG. 17 and FIG. 18 represent valve 4 and valve 5 respectively in the simple volumetric apparatus shown schematically in FIG. 4. In the schematic diagram of the preferred embodiment of the present invention FIG. 6, valves E1 (of FIG. 15 and FIG. 16) is representative of the automated valve 612h (or 612e if 612h and none, one, or both of 612g and 612i are open) and E2 is representative of the automated valve 612k. The method of sorption concentration proceeds as follows: First, valve E2 is closed. Then valve E1 is opened and the calibrated reservoir volume $V_R$ is discharged of gas. This is done, either by opening valve 2 (valve 612d in FIG. 6) and discharging to the vent and vacuum connections 624 and 626, or by discharging to a preset pressure through the gas pressure regulator 606. In the second step valve E1 is closed and the aliquot pressure $P_{Rj}$ in the calibrated reservoir volume $V_R$ is recorded using pressure transducer 633 or 637 if the pressure is below the maximum reading pressure of 637 and valve 612j is open. Then E2 is opened and the pressure in the sample container (and gas lines) $V_C$ and the reservoir volume $V_R$ due to desorption is recorded and continues to be recorded at specified time intervals. Again, the pressure is measured using pressure transducer 633 or 637 if the pressure is below the maximum reading pressure of 637 and valve 612j is open. This pressure change measurement provides a means to evaluate the amount of gas desorption from the sample. The quantity of gas desorbed at each step $N_j$ is again given by EQ. 1. When the change in pressure finally slows to a specified limit, this pressure reading $P_j$ is taken as the equilibrium pressure $P_{Ej}$ and the calculated quantity of gas desorbed $N_j$ corresponding to the equilibrium pressure is taken as the equilibrium concentration $N_{Ej}$ desorbed in that aliquot. For PCT measurements the process is repeated.

Figure 2:
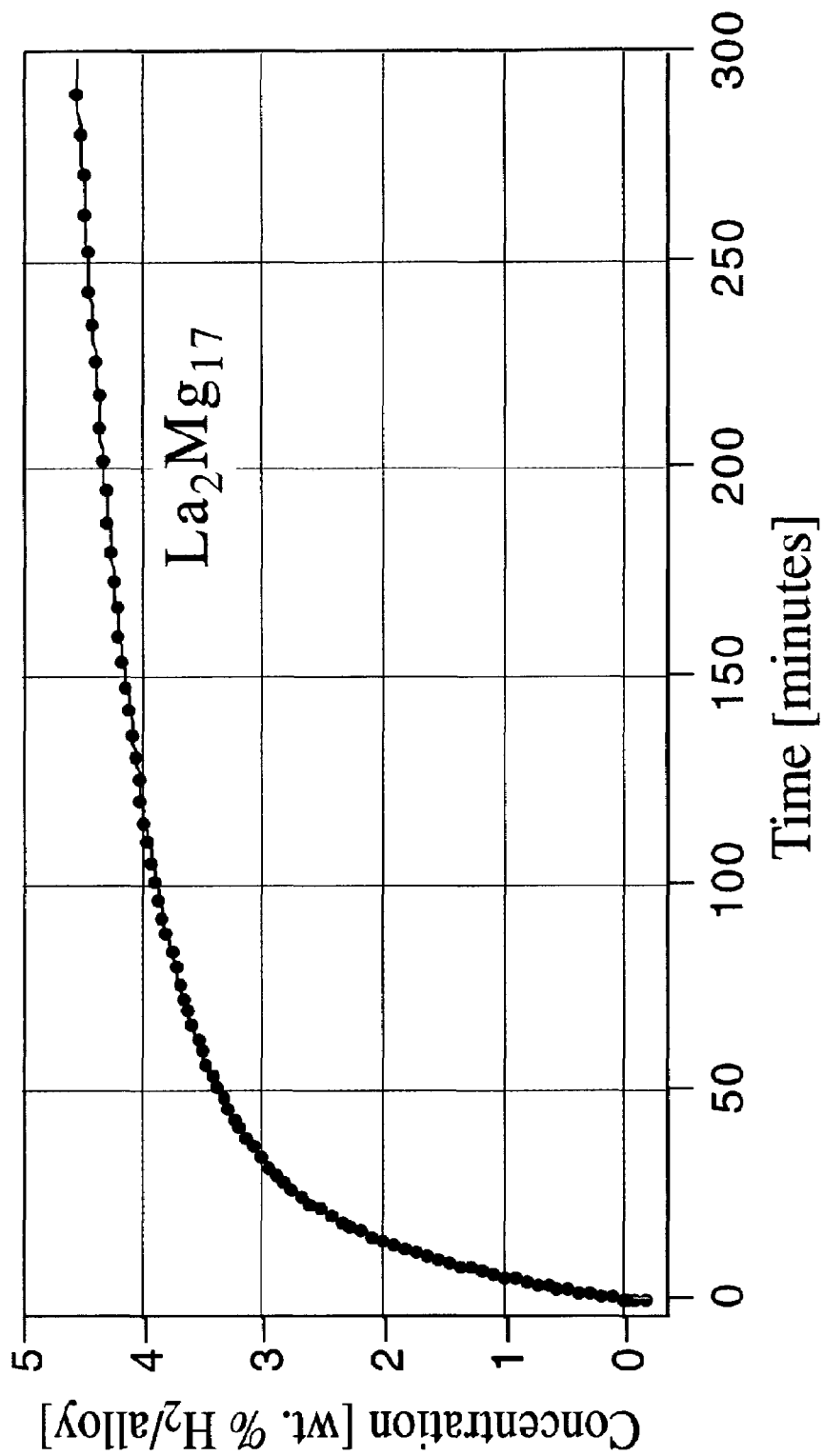
FIG. 2) is an example Kinetics measurement of hydrogen absorption by the alloy $La_2Mg_{17}$.
Figure 3:
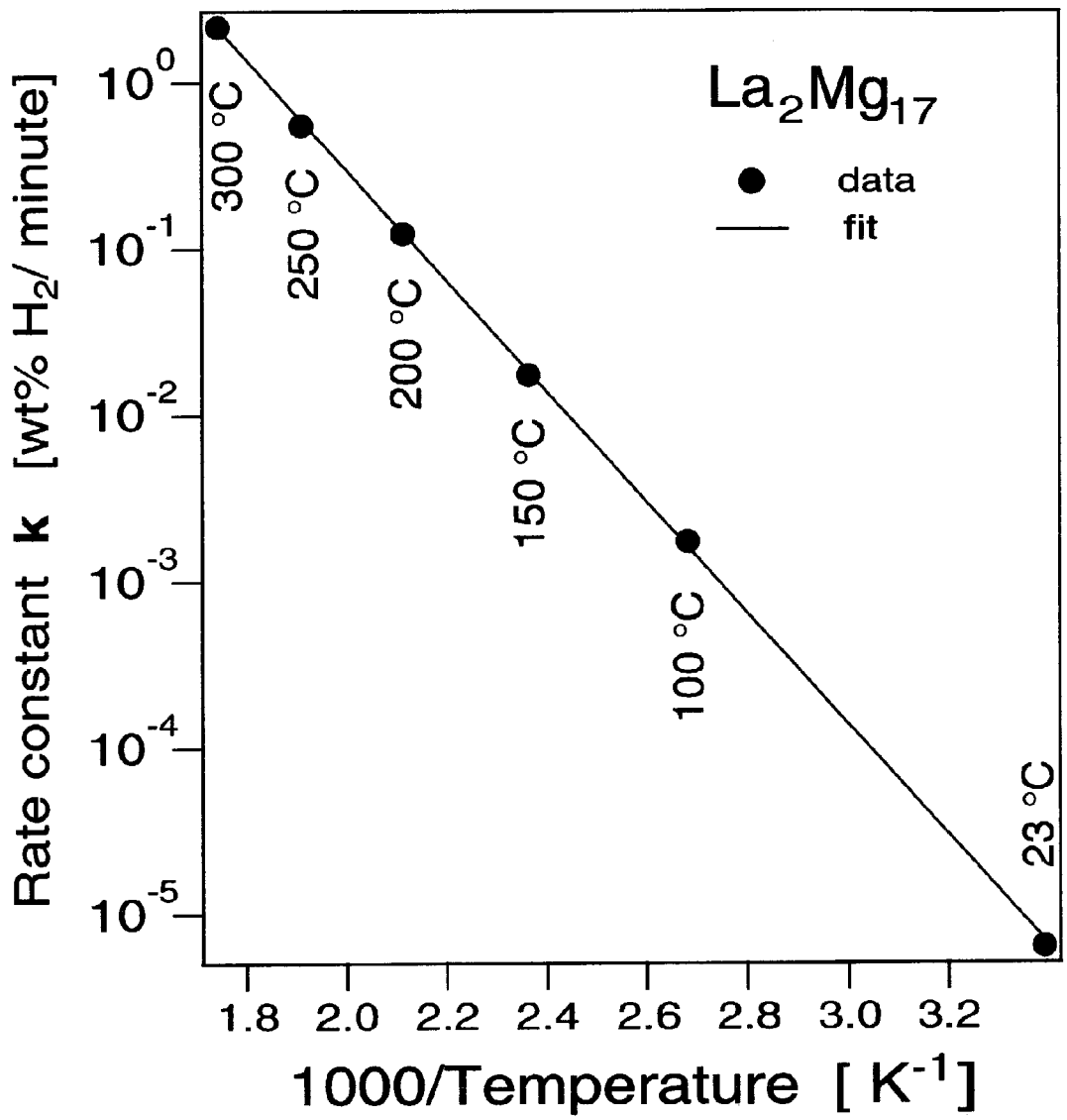
FIG. 3) is an example Arrhenius plot of the log 10 rate of hydrogen absorption versus inverse temperature measured for the alloy $La_2Mg_{17}$.
Figure 19:
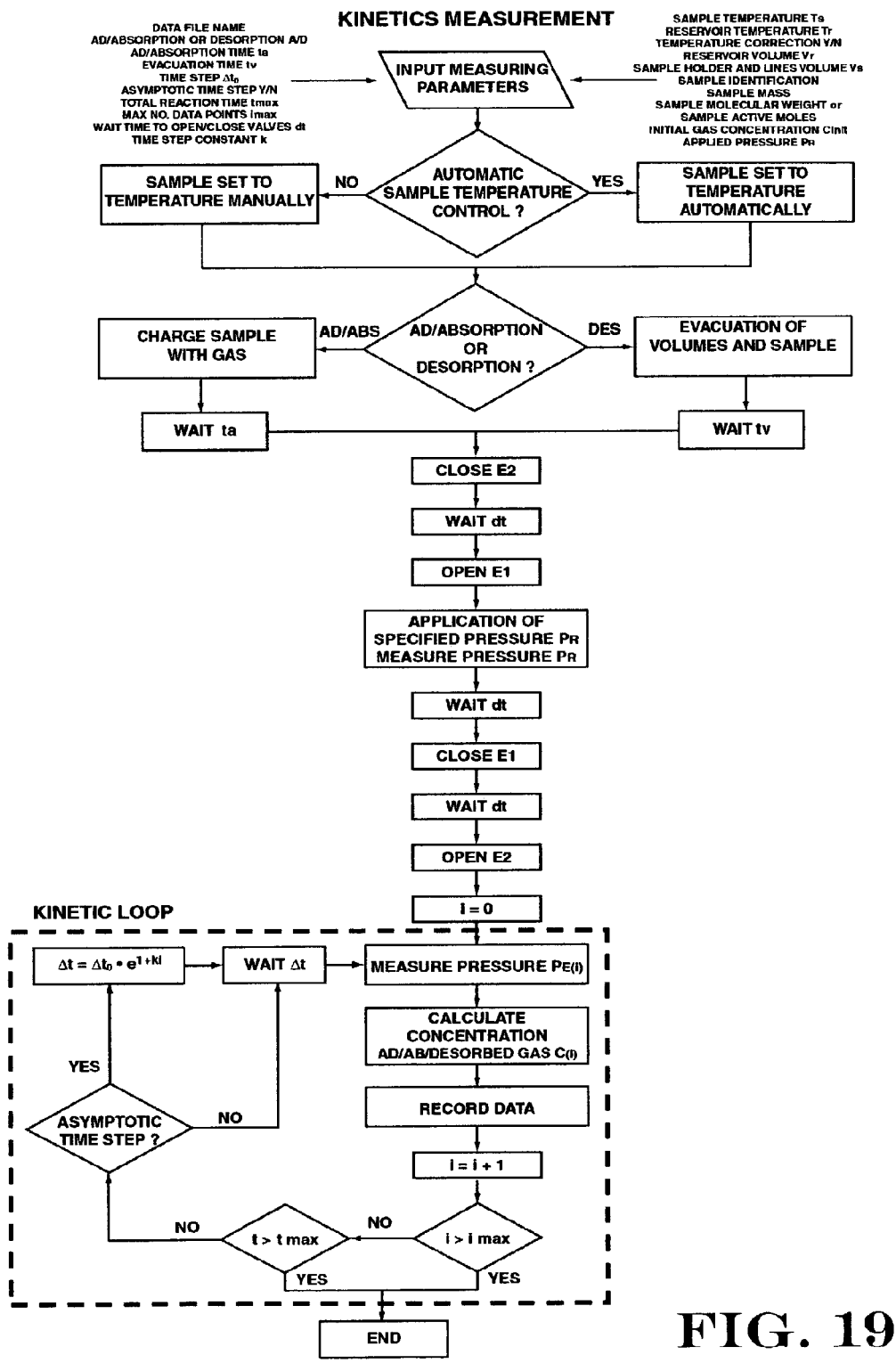
FIG. 19) is a flow chart for measuring gas sorption or desorption kinetic properties of a sample using the apparatus (gas sorption/desorption analyzer) of the invention.

Kinetics Measurement: The process making both sorption and desorption kinetics measurements is identical to the two processes respectively described above. For sorption, an aliquot represents exposing the sample to a quantity of gas at a pressure high enough for sorption by the sample to occur at the given sample temperature. For desorption, an aliquot represents exposing the sample to a large volume filled with gas at a pressure low enough for desorption by the sample to occur at the given sample temperature. In general, kinetics measurements are performed using only one cycle (i.e. j=1 consisting of Steps 1 and 2). The measurement is usually made with a large enough aliquot to completely ad/absorb or desorb the sample. However, smaller and multiple aliquots in a kinetics measurement may be performed. After proceeding as described in Step 1 above, E2 is opened and the pressure in the sample container (and gas lines) $V_C$ and the reservoir volume $V_R$ is recorded and continues to be recorded at specified time intervals. The quantity of gas ad/absorb or desorb $N_j$ at each time interval is given by EQ. 1. The results of the kinetics measurement are plotted as the quantity of gas ad/absorb or desorb $N_j$ at each time interval (left axis) versus the corresponding total amount of time passed for each measured value of $N_j$. An example of such a measurement is given in FIG. 2. FIG. 19 shows a flow chart of the preferred process for measuring gas sorption or desorption kinetic properties of a sample using the gas sorption/desorption analyzer of the invention.

Figure 20:
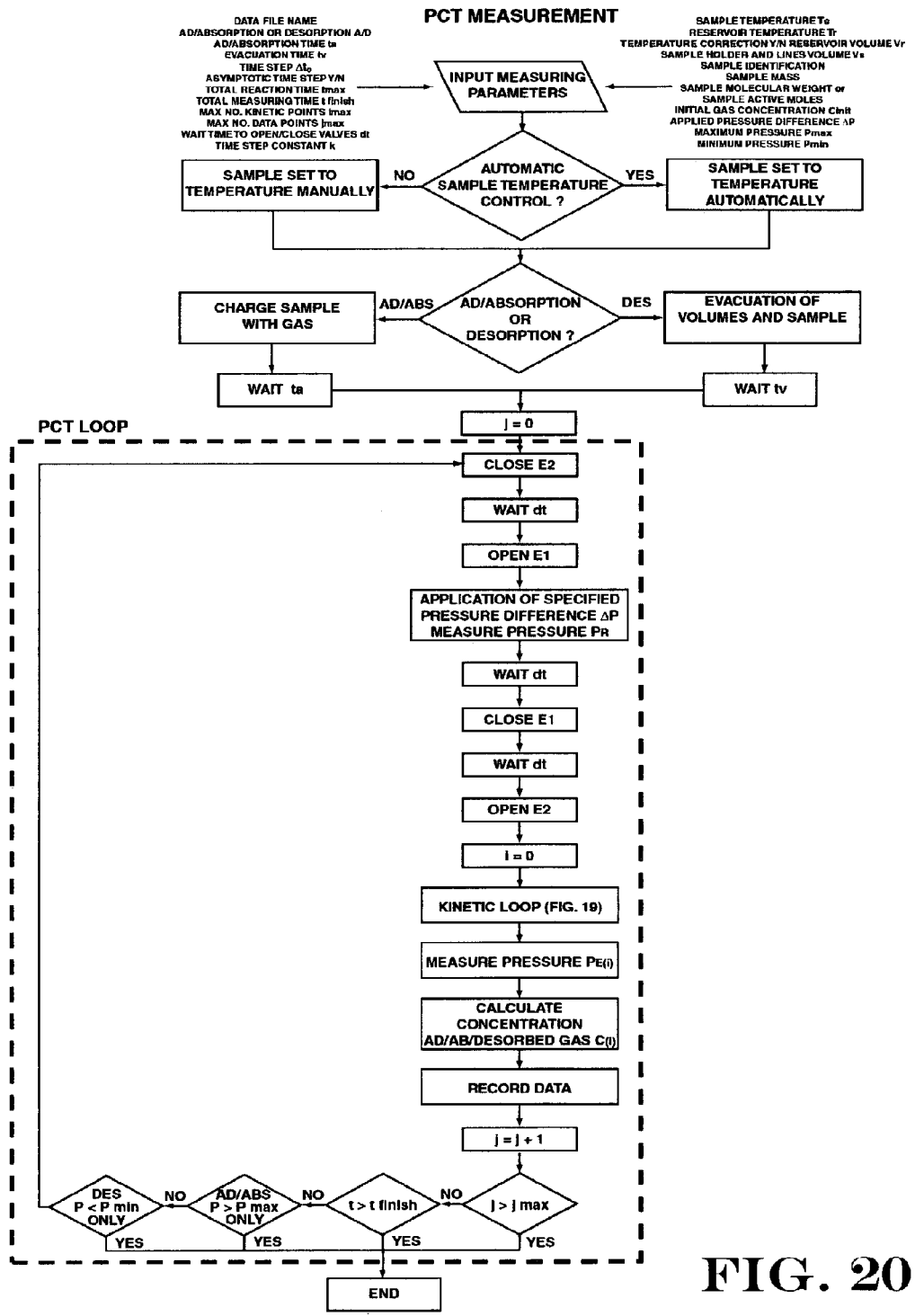
FIG. 20) is a flow chart for measuring gas sorption or desorption PCT properties of a sample using the apparatus (gas sorption/desorption analyzer) of the invention.

PCT Measurement: The process for making both sorption and desorption PCT measurements is identical to the kinetics measurements described above. In this case, however, small volumes and small pressure differentials are used to provide only small aliquots. Thus, the sample ad/absorbs or desorbs a small quantity of gas. The process as described for the kinetics measurements is repeated for many cycles (i.e. j>1, with each cycle consisting of Steps 1 and 2 as described above). The applied aliquot pressure is increased with each cycle for sorption PCI measurements and decreased with each cycle for desorption PCT measurements. At the end of each cycle the equilibrium pressure $P_j$ and total equilibrium concentration $N_{Ej}$ are recorded. A PCT curve is constructed by plotting $P_j$ versus the corresponding value of the total equilibrium concentration $N_{Ej}$. A typical PCT diagram constructed in this manner is shown in FIG. FIG. 20 shows a flow chart of the preferred process for measuring gas sorption or desorption PCT properties of a sample using the gas sorption/desorption analyzer of the invention.

In addition to the PCT data that is collected during such a measurement, the change in time of the gas pressure (and therefore concentration) with each aliquot is essentially a localized kinetics measurement. In the preferred embodiment of the present invention, this data can also be collected during PCT measurements to provide measurements of sorption and desorption kinetics at each measuring point along a PCT curve.

Figure 21:
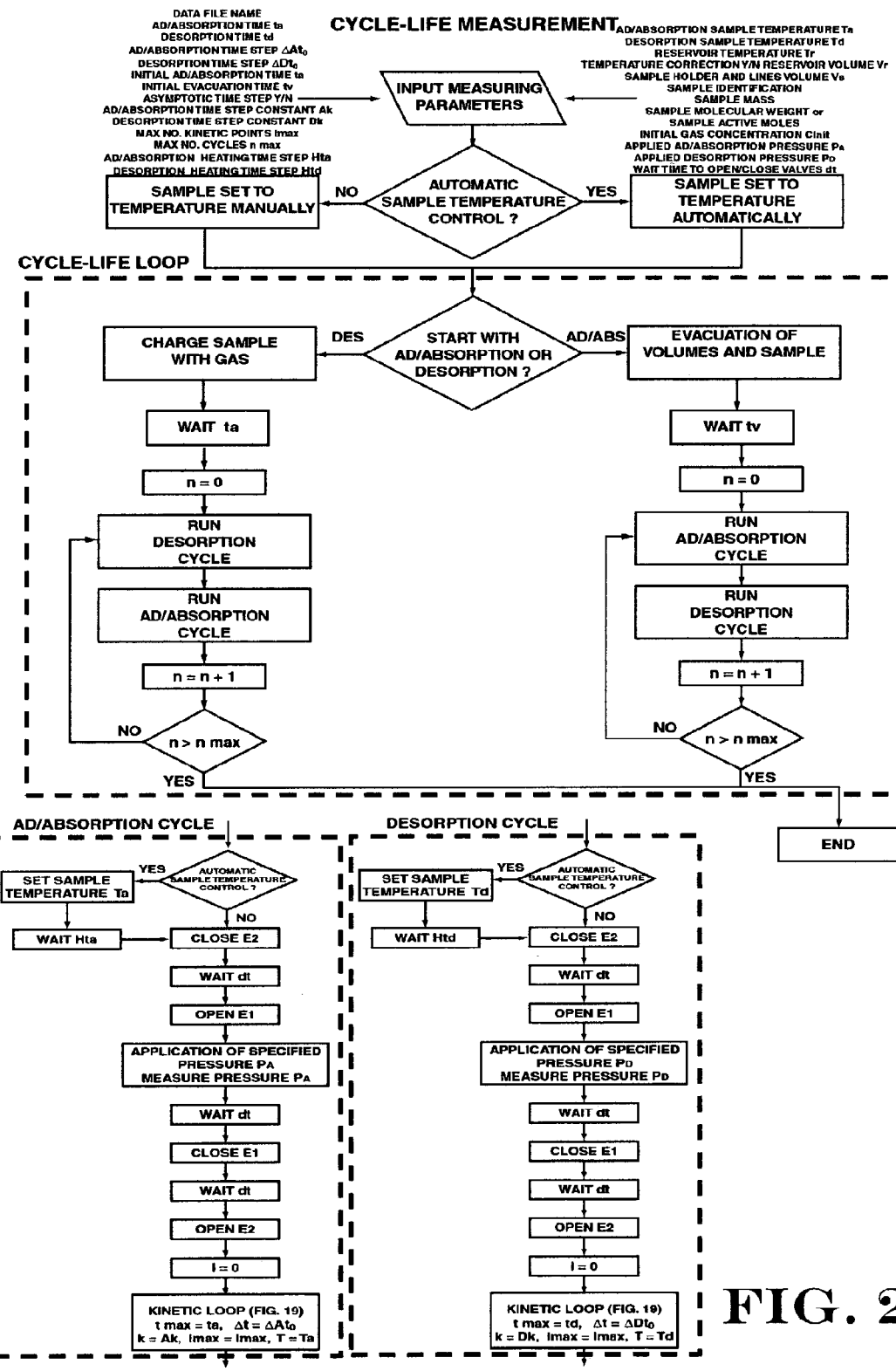
FIG. 21) is a flow chart for measuring gas sorption or desorption cycle-life properties of a sample using the apparatus (gas sorption/desorption analyzer) of the invention.

Cycle-Life Measurement: The process making cycle-life measurements is simply a series of cycles consisting of a sorption measurement followed by a desorption measurement (or vise versa). Each kinetic measurement is made in an identical manner to the kinetics measurement process described above. For sorption, an aliquot represents exposing the sample to a quantity of gas at a pressure high enough for sorption by the sample to occur at the given sample temperature. For desorption, an aliquot represents exposing the sample to a large volume filled with gas at a pressure low enough for desorption by the sample to occur at the given sample temperature. The measurement is usually made with a large enough aliquot to completely ad/absorb or desorb the sample. However, smaller and/or multiple aliquots in a kinetics measurement may be performed. The cycle-life measurement can be set up to cycle indefinitely, or for a fixed number of cycles, or until a certain criteria has been met. Examples of such criteria are: 1) the reversible sorption or desorption capacity has dropped below a specified value, or 2) the sorption or desorption rate has dropped below a specified value, or any other criteria that changes with continued cycling. The duration of the sorption and desorption steps of each cycle may be set for a fixed amount of time or be continuous until a certain criteria has been met. Examples of such criteria are: 1) the reversible sorption or desorption capacity has reached a specified value, or 2) the sorption or desorption rate has dropped below a specified value, or any other criteria that changes with time. In the preferred embodiment of the present invention the experiment parameters chosen for the sorption part of the cycle can be different than the experiment parameters chosen for the desorption part of the cycle. Such parameters include: the criteria controlling the duration of sorption and desorption, the applied pressures, the sample temperature, the data collection interval, whether or not weighted averages are used for the gas temperature, whether or not constant applied sample pressures are used, and the size of the calibrated reservoir volume used. These parameters can also be changed during the cycle-life measurement by the operator or as a function of the number of cycles completed. FIG. 21 shows a flow chart of the preferred process for measuring gas sorption or desorption cycle-life properties of a sample using the gas sorption/desorption analyzer of the invention.

Automation: Computer software algorithms are designed to simulate the manual operations that an experimenter would perform on an identical system with manual valves. Among other things the advantage of automation is that the experimenter need not be present during the duration or even at intervals during the experiment. Many gas sorption and desorption experiments are of a slow nature, requiring hours, even days or months to run to completion. It is not practical for the experimenter to be present to make manual manipulations in such cases. In the present invention automation is achieved using the pneumatic valves 612*a-j* which are operated using pressurized air switched on and off by the electric solenoid valves 604*a-j* that are controlled by the computer 506. Hardware PID controllers 603 and 728 are used to automatically achieve desired gas pressures. Software PID controllers are used to automatically achieve desired sample and reservoir temperatures. The operator inputs the desired pressure and/or temperature into the computer 506. The computer software algorithms send these values through the communication link 507 to the data acquisition, control, and safety system module 1110 via the communication control hub which sends a signal to the pressure controllers 603 or 728 to regulate the pressures of the regulators 606 or 720 respectively and/or to the digital output device 1113 that delivers power to either the enclosure heating element or the sample heater 701 (or 1001). Data collection is also automated using analog to digital conversion of readings from the pressure transducers 633, 637, 617, 619, 725, 726 and the thermocouples 705, 706, 707, 820, 1121, 1122. Data collection is also automated using analog to digital conversion of the pressure transducer and thermocouple readings. Data is collected at logical intervals determined by the type of measurement and the current dynamics of the process being measured. For example, during kinetics measurements, data is collected at time intervals of $dt = \Delta t(e^{(1+ki)})$, or alternatively $dt = \Delta t(1 + e^{(ki)})$, or alternatively $dt = 1 + (t \cdot k)^3$, where $\Delta t$ is the starting time interval, k is a constant which determines the rate at which dt changes with i, an i is the interval. This enables data to be collected rapidly at the beginning of a kinetics measurement and then at increasing larger intervals as time goes on and the rates drop off. This dramatically reduces the quantity of data collected while retaining all of the pertinent information. One significant advantage of using automated pneumatic valves is that the pneumatic force applied to the valves is generally constant and well regulated. It is known that this greatly improves the operating life time of such valves compared to manual operations. Thus, an automated apparatus of this type is expected to function for a significantly longer period of time before requiring maintenance than a manual system.

Figure 23:
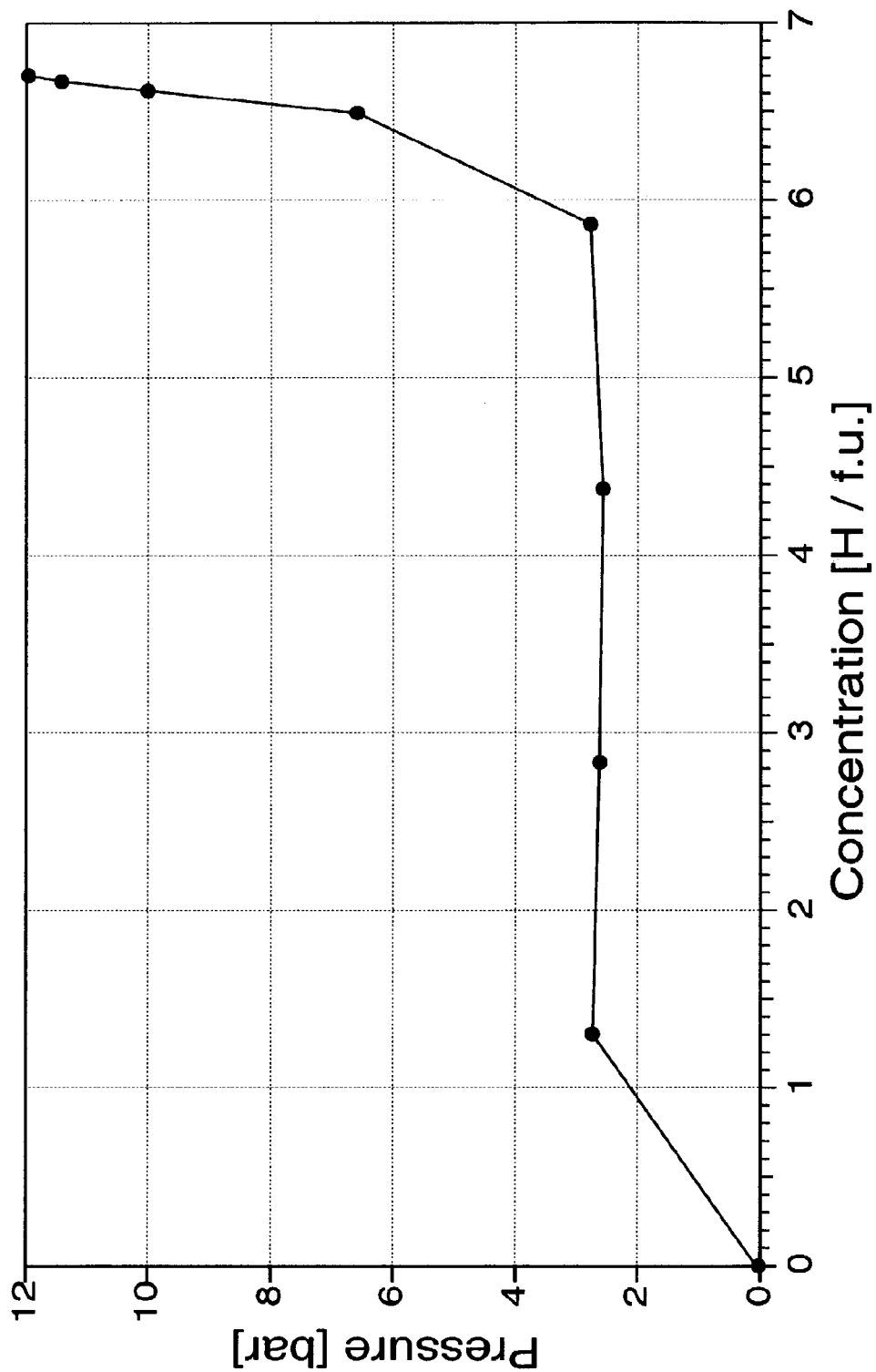
FIG. 23) is PCT plot of hydrogen absorption in $LaNi_5$ using a fixed calibrated reservoir pressure of about 12 atm.
Figure 24:
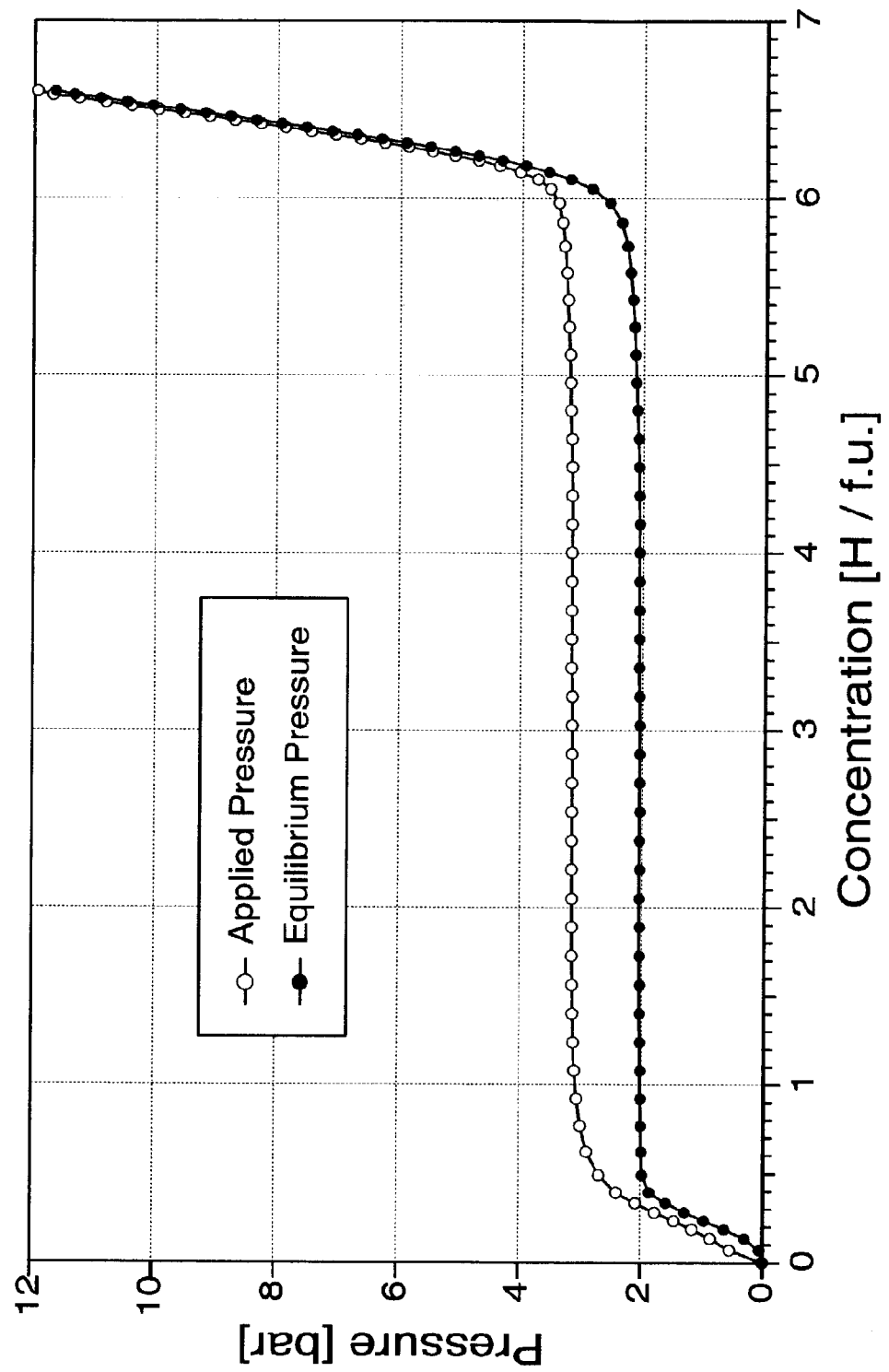
FIG. 24) is PCT plot of hydrogen absorption in $LaNi_5$ using a calibrated reservoir pressure that increases slowly with each aliquot up to a pressure of about 12 atm.

Pressure Regulation: In the present invention the problem of making finely spaced measurements of gas sorption and desorption along the PCT curve has been solved by utilizing a pneumatically controlled pressure regulator combined with a pneumatic PID feed-back controller. These components is shown in FIG. 6. They consists of a hardware PID air controller 603 and gas pressure regulator 606 that regulates the pressure of the gas supplied to the system from an internal gas vessel 616 which is filled with a gas from an external supply. The hardware PID controller receives a signal from a computer interface (in the form of an applied voltage from the pressure regulator analog output device 1114) which indicates the desired gas pressure. The controller then regulates the air pressure supplied to the pneumatic gas pressure regulator until the desired gas pressure is achieved. PID feedback comes from a supply gas output pressure transducer 619 positioned downstream of the gas pressure regulator that is connected directly to the hardware PID air controller 603 as well as the analog input device 1112. In the case of PCT measurements, the pressure of each aliquot is regulated to a desired value slightly above the plateau pressure for sorption and slightly below the plateau for desorption. In the preferred embodiment of the present invention, the actual value of the desired pressure can be selected using any number of criteria. For example, the applied pressure can simply be increased (or decreased) linearly over the duration of the measurement. The most common method, however, is to adjust the applied pressure to a fixed value above (or below for desorption) the last measured equilibrium pressure. In this manner the quantity of gas absorbed or desorbed from each aliquot is nearly the same. Thus, the data points will be distributed fairly evenly along the PCT curve. The advantages of this method can be seen by comparing FIG. 23 with FIG. 24. The PCT measurement shown in FIG. 23 was made on the absorption of hydrogen by the intermetallic compound LaNi.sub.5. The applied aliquots were fixed at a pressure of 12.5 atm. This caused the broad distribution of data points for the lower pressure portion of the measurement. FIG. 24, on the other hand, was made for hydrogen absorption by the same sample on the same device, however, the applied pressure was increased slowly from vacuum to 12.5 atm over the duration of the measurement. This gave smaller aliquots of gas, and therefore, a more even distribution of data points on the PCT curve. This is important to be able to discern details in the PCT measurement such as phase transitions that might other-wise be overlooked. The same process can be applied to desorption measurements as sorption measurements. In the desorption case the gas pressure regulator 606 is used to decrease the aliquot pressures with each new aliquot by discharging gas through the discharge line 621 until the desired supply pressure is achieved.

Constant Pressure Measurements: In many cases, it is important to be able to test gas sorption and desorption in a material under conditions that most closely resemble those found in the application for which the materials are being developed. For instance, hydrogen storage materials used to supply hydrogen to a fuel cell would need to do so at pressures at or above 1 atm. Likewise, the procedure for charging such materials with gaseous hydrogen would generally be performed at a constant overpressure, for example, by loading directly from a pressure regulator on a gas cylinder. In the laboratory, volumetric sorption measurements are often performed by measuring the pressure drop as gas is absorbed from a small known volume. Similarly, desorption experiments are performed by measuring the increasing gas pressure while desorbing into a small known volume that had been evacuated. Both measurements involve changes in pressure of the gas surrounding the sample. These pressure changes may effect the sorption or desorption behavior of the material to some degree. To best simulate real conditions, sorption and desorption measurements on test samples should be performed using constant pressures. The preferred embodiment of the present invention implements constant pressure sorption and desorption measurements by placing gas pressure regulator (606 and 720 respectively) between the sample 814 and the calibrated reservoir volume. The sorption or desorption properties of the material are still determined by measuring the change in pressure in a calibrated volume. However, the pressure of the gas surrounding the sample is held constant using a pressure regulator. Constant pressure sorption experiments utilize the same internal PID controlled gas pressure regulator 606 used for regulating the supply pressure of aliquots in PCT measurements described above. This pressure regulator maintains a constant pressure greater than the equilibrium plateau pressure over the sample. The difference is that these experiments use a calibrated reservoir volume (vessel 616, gas supply line 615, and fittings) that is upstream of the pressure regulator. The pressure drop in this volume is then used to calculate the quantity of gas taken up by the sample. Constant pressure desorption measurements utilize an external back-pressure regulator 720, shown in FIG. 7, to maintain a constant pressure of the desorbed gas surrounding the sample 814. This pressure regulator maintains a constant pressure which is below the equilibrium plateau pressure of the sample. It is attached between the sample container 801 and the external gas handling portion 901. The gas released from the sample flows through the back-flow regulator 720 into a large evacuated calibrated reservoir volume (either vessels 629 or 631 or both, and gas lines 632, 627 and fittings). The desired back-pressure is controlled using a hardware back-pressure regulator pneumatic PID controller 728 that regulates the pressure of the gas supplied from the desorbing sample to the evacuated reservoir volume. The hardware back-pressure regulator pneumatic PID controller 728 receives a signal from a computer interface (in the form of an applied voltage from the pressure regulator analog output device 1114) which indicates the desired gas pressure. The controller then regulates the air pressure supplied to the pneumatic gas back-pressure regulator 720 until the desired gas back-pressure is achieved. PID feedback comes from a back-pressure regulator input pressure transducer 725 positioned on the sample side of the gas back-pressure regulator 720. The pressure increase in the calibrated reservoir volume is measured to calculate the quantity of gas released by the sample. For complete sorption and desorption measurements the calibrated volumes must be large enough, and the pressures high (or low) enough, and/or the samples small enough that the pressure in the calibrated volume does not reach the plateau pressure of the sample. If this occurs sorption or desorption may stop without being complete. In the preferred embodiment of this invention, PID controlled pressure regulators are used for both constant pressure sorption and desorption measurements.

Regulated Gas Temperature: Changes in temperature of the gas due to changes in the ambient air temperature will cause errors in the measurements that are difficult to compensate for simply by making corrections to the data. A distinguishing feature of this invention over the prior art is that the main portion of the gas is maintained at a constant temperature at using an insulated enclosure 502, an enclosure heating element 639 and a air re-circulating fan 640. In a volumetric measurement, it is critical that the temperature of the gas is know for an accurate determination of the quantity of gas sorption or desorption by a sample. It is possible to measure the gas temperature at a point, however, that might not be representative of the average gas temperature throughout the gas sorption/desorption analyzer. The best method is to maintain the gas at a fixed temperature within most of the gas sorption/desorption analyzer and to minimize the gas volume that may be at another temperature. In the present invention, the gas is maintained at a constant temperature slightly above room temperature by placing the main portion of the gas sorption/desorption analyzer within an insulated enclosure 502 which is heated. In the preferred embodiment of the present invention, the heating is provided by an electric resistive enclosure heating element 639, however, other types of heating may also be used. The temperature is regulated using a software PID controller that supplies power to the enclosure heating element 639 through the enclosure heating element 110 V AC analog output device 1116. Feedback for the software PID controller comes from an enclosure thermocouple 1123 place inside of the enclosure. The internal temperature distribution is made uniform by using an internal circulating air fan 640.

Software PID Controls: In the preferred embodiment, this invention utilizes software PID controllers running on the computer 506 and interfacing with the gas sorption/desorption analyzer 501 through the communication link 507, data acquisition, control and safety system 1110, and communications control hub 1111, combined with an analog input device 1112 and a digital output device 1113 and analog output devices 1114, 1115, and 1116 to control the pressure regulators 606 and 720, enclosure heater 639, and the sample heaters 701 or 1001. This reduces the complexity of the system hardware. The first software PID control is used to regulate the temperature of the air inside the enclosure using an electric resistive heater and internal fan to circulate the air as described above. The second PID control regulates the temperature of the sample 814 by controlling the sample heater control relay 1109 through the digital output device 1113. PID feedback comes from one of several thermocouple (705, 706, 707 or 820) place inside of or in close proximity to the sample container.

Figure 22:
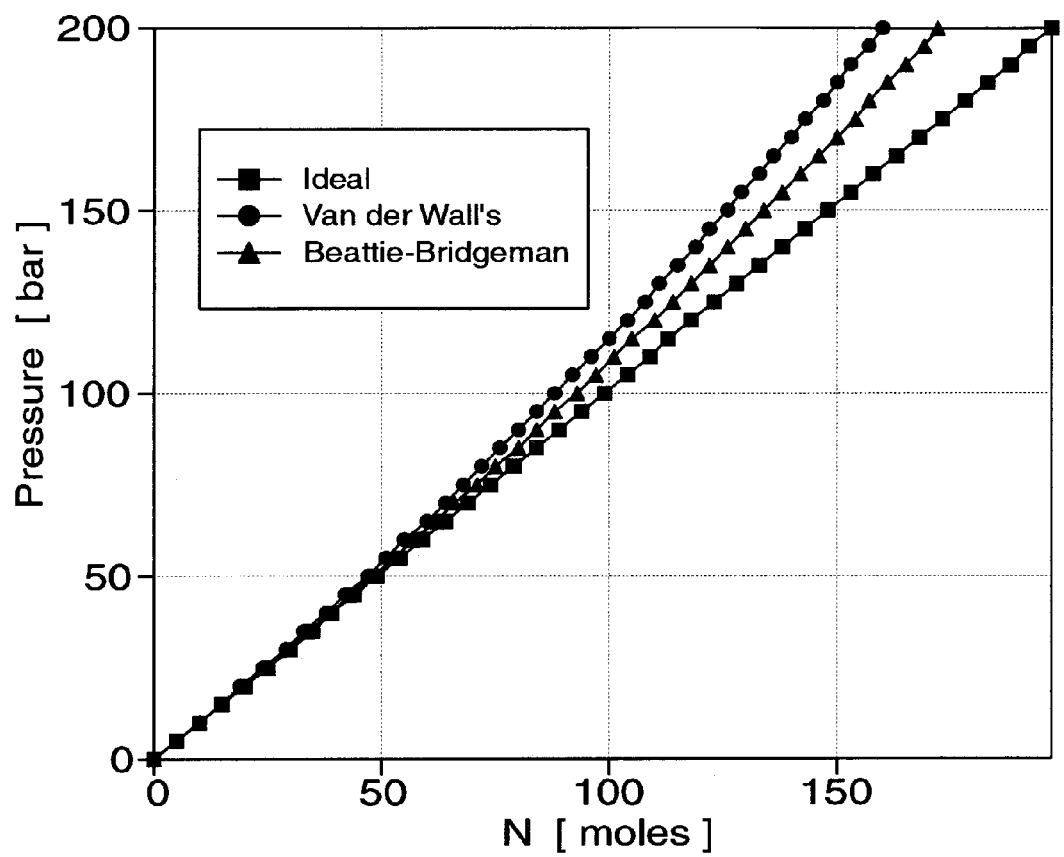
FIG. 22) is a plot of the number of moles in a gas versus pressure calculated for hydrogen gas using the ideal gas law, the Beattie-Bridgeman equation of state, and the Van der Wall's equation of state.

Non-Ideal Gas Compensation: The preferred embodiment of the present invention includes data analysis software employing automatically calculation of non-ideal gas behavior to correctly determine the quantity of gas from changes in pressure. The preferred embodiment uses a zero-point solving routine to solve the "Beattie-Bridgeman" equation of state to determine the quantity of gas sorption or desorption based on changes of pressure in a known volume. Similarly, other equations of state (for example Van der Waals equation of state) for non-ideal gas behavior can also be used. FIG. 22 shows a plot of these two methods for calculating the quantity of gas from pressure, volume and temperature compared with the ideal gas law. The plot shows the number of moles in of hydrogen gas in a one liter volume at 20.degrees. C. versus pressure calculated using the ideal gas law, the Beattie-Bridgeman equation of state, and the Van der Wall's equation of state.

Semi-Automated Volume Calibrations: To be able to accurately calculate the quantity of gas taken-up by or released from a sample, it is generally necessary that the entire gas volume be known. The various control volumes of the gas sorption/desorption analyzer can be calibrated once for every measurement. However, the gas volume of in sample container will change if different sample containers are used and will also be dependent on the volume of the sample itself. For this reason, the volume of the sample container 801 including the sample 814 should be measured every time it is changed. The volume of the sample container (and sample) can be determined after it is attached to the gas sorption/desorption analyzer 501 by evacuating or supplying a given pressure to the sample container 801, closing the sample container valve 805, measuring the pressure of a gas (this should be equivalent to the pressure in the sample container). Then a calibrated volume on the gas sorption/desorption analyzer is either evacuated or filled to a pressure which is different from that in the sample container and this pressure is measured. The sample container valve 805 is then opened and when the pressure has come to equilibrium between the sample container and the calibrated volume, the volume of the sample container can be determined from the resulting change in pressure. Usually this procedure is repeated several times to get an accurate measurement of the sample container plus sample volume. The calibration gas that is used for these measurements should be inert and the measurement done at temperatures for which there will be no significant sorption or desorption of the calibration or other gasses by or from the sample. In the preferred embodiment of this invention the calibration gas is helium. To aid in this calibration process, the present invention includes a semi-automated routine for performing such a sample volume calibration measurement. The routine opens the appropriate valves or instructs the operator to do so, supplies and measures the helium pressures, and calculates the volume of the combined sample container and sample. Helium gas is supplied to the gas sorption/desorption analyzer through the calibration gas connector 607 and calibration gas supply line 608. The helium is introduced into the gas handling system by opening the automated valve 612a.

Sample Density Measurements: The same type of volume calibration measurements as described above can be used to determine the density of the sample. To do this, the sample container 801 is first attached to the gas sorption/desorption analyzer without a sample. Its empty volume is calibrated as described above. Next the same sample container 801 is filled with a sample 814 of a known mass and then attached to the gas sorption/desorption analyzer. The volume calibration is performed once again as described above. The difference in the volume of the sample container 801 with and without the sample 814 is the solid volume of the sample. The mass of the sample divided by this volume gives the density of the sample. The semi-automated volume calibration procedure of this invention (described above) provides an aid to simplify this process.

In Situ Sample Density Measurements: In addition, there is a unique advantage to performing the type of density measurement procedure described above. By performing such measurements directly on the gas sorption/desorption analyzer 501 that is used for making gas sorption and desorption property measurements the density of the sample (or volume expansion/contraction) can be measured in different states of gas loading. This is done by placing the sample under conditions with respect to temperature and hydrogen partial pressures that it will not desorb the active gas. In the preferred embodiment of this invention, the sample container 801 and solid sample 814 volume are measured before any gas sorption or desorption measurements (as described above). Then active gas loading or unloading is performed. When the desired active gas content of the sample is achieved, the sample container valve 805 is closed and the temperature of the sample is lowered to the point at which active gas will desorb only very slowly when exposed to an atmosphere containing only an inert gas. The sample container 805 and solid sample 814 volume are measured again using an inert gas as described above. Thus, any changes the solid volume (and therefore changes in density) of the sample associated with active gas loading can be measured. In the case where there is no change in the crystal structure, the active gas induced change in density may be a good indirect measurement of lattice expansion or contraction associated with a change in active gas concentration in the sample.

Extended Dynamic Pressure Range: The preferred embodiment of the present invention includes high- and low-range pressure transducers, sensors, or gauges to be able to cover a large dynamic range of pressures. Strain gauge pressure transducers are available that are very accurate (generally 0.2% of full scale). However, because the accuracy has a constant value over the entire range of pressures the error at low pressures is quite substantial. Capacitance manometers, on the other hand, have proportional errors which decrease as the pressure decreases. Unfortunately, these devices are often less accurate (generally 1% of reading) than the strain gauge type at higher pressures. The present invention overcomes this problem by using two or more pressure transducers to cover a broad range of pressures accurately. In the preferred embodiment, this invention includes two pressure transducers (shown in FIG. 6), one covering the range 0 to 200 at, (high-pressure transducer 633) and a second covering the range 0 to 7 atm(low-pressure transducer 637). The correct transducer is automatically chosen depending on the range pressure of the pressure being measured. This is accomplished by first reading the pressure with the high-pressure transducer 633 to determine the range that the pressure falls into and then selecting the appropriate transducer to make the final pressure measurement.

Multiple Calibrated Reservoir Volumes: The present invention is an gas sorption/desorption analyzer that includes several calibrated volumes. These volumes allow the control reservoir volume to be changed from small to large volumes depending on: a) the type of measurement to be made, b) the quantity of sample to be measured, and c) the quantity of gas that will be ad/absorbed by the sample. For example, a kinetics measurement in which a sample is completely ad/absorbs or desorbs a gas in one step, requires a larger reservoir volume than a PCT measurement in which sorption or desorption takes place in a series of small aliquots from or to a much smaller reservoir volume. Another example, is that sorption of a gas at high pressure (ca. 100 atm) requires a small volume (to accurately measure pressure changes). Whereas, desorption at low pressures (ca. 1 atm) requires a large volume to be able to maintain a pressure below the equilibrium plateau pressure. In the preferred embodiment, the reservoir volumes can be switched as required between approximately 0.01 to 1 liter. An additional advantage in the preferred embodiment of the invention, is automated valves on each of several pre-calibrated volumes allows the reservoir volume to be changed at any time even during an experiment, either manually or through automated computer algorithms for making a given experiment. In the preferred embodiment of the invention, these calibrated reservoir volumes (shown in FIG. 6) includes either vessels 629 or 631 or both, and gas lines 632, 627, valves 612$h,j,k,i,g,e$, fittings, and pressure transducers 633 and or 637. Other calibrated volumes include the gas vessel 616 and many of the other gas lines, fittings, valves, and pressure transducers.

Reduced Operating Volumes: Small working volumes is an important feature of the present invention. The quantity of gas in an aliquot depends on the pressure, temperature and volume of the gas. Small quantities of a sample, low gas concentrations in a sample, or high working pressures require measurements to be made with small aliquots of gas. Therefore, small reservoir volumes must be used to measure such small quantities of gas or even large quantities at high pressure (ca. 100 atm). The present invention employs small internal diameter tubing, short distance, and spacers to fill empty spaces in the sample container to reduce the actual working volumes in the gas sorption/desorption analyzer. The entire working volume of the system can be reduce to on the order of 15 milliliters. This includes the total added volumes of the external gas handling system 901, the sample container 801 using spacers 811, the gas lines 632, 634, 638, the pressure transducers 633 and 637, and the automated valves 612 $h,j,k$. In addition, the implementation of small gas volumes in the sample container 801 also reduces the problem of uncertainty in the gas temperature when the sample 814 is at a temperature significantly different than the bulk of the gas in the gas sorption/desorption analyzer. By reducing the free gas space in and close to the sample container, the average temperature of the gas in the system is approximately equal to that of the temperature of the reservoir. In this manner the gas temperature being chosen as the enclosure temperature is a good approximation for calculating the quantity of gas in the system, even at elevated sample temperatures.

Mobility: The external gas handling portion 901 and feet 505 are designed to be removed for easy transport of the gas sorption/desorption analyzer 501.

System Power Failsafe Mechanism: In the preferred embodiment, this invention employs a failsafe mechanism to shut off power to the gas sorption/desorption analyzer if enclosure is opened. This is accomplished using low voltage power safety relay 1127 and electrical pressure switches 1103 (such as push-button enclosure power safety switches) in contact with the enclosure's panels 503. These switches form a series safety circuit as shown in FIG. 11. The main power supply is controlled by the power safety relay 1127. If the safety circuit is broken by removing a panel from the gas sorption/desorption analyzer, the relay will open, shutting off power to the system.

Enclosure Heating Failsafe Mechanism 1: In the preferred embodiment, this invention employs a failsafe mechanism that shuts off power if enclosure temperature goes above a preset temperature limit (for example 50.degree. C.). The control software checks the enclosure temperature on a regular basis and will shut off power to the system by opening the safety relay on the main power supply to the gas sorption/desorption analyzer if the enclosure temperature rises above the maximum set point. This is not shown in FIG. 11, but it is comprised of adding a relay device to the data acquisition, control, and safety system 1110. This relay would be wired in series with the power safety relay 1127 and controlled by the computer 506. When a signal is sent from the computer to this relay the circuit would be broken and the power safety relay 1127 would open shutting off power to the gas sorption/desorption analyzer 501.

Enclosure Heating Failsafe Mechanism 2: In the preferred embodiment, this invention employs a failsafe mechanism to prevent over-heating of the enclosure. This is done by selecting an electrical resistive heater enclosure heating element 639, that will only deliver enough heat to raise the enclosure temperature to a reasonable temperature (for example 50.degree. C.).

Gas Leak Failsafe Mechanism 1: In the preferred embodiment, this invention employs a failsafe mechanism to prevent buildup of hydrogen or other flammable gasses and the possibility of an explosion if there is a gas leak within the enclosure 502. The enclosure 502 is designed not to be air-tight. There are vents 511 with dust filters at the bottom and top of the enclosure. In the event that there is a gas leak within the enclosure, the vents prevent the gas concentrations from building up to dangerous levels by allowing the gas to escape through the top or bottom vent by natural buoyancy and thermal convection. In another embodiment of the invention, outside air is slowly forced through the enclosure by a ventilation fan mounted on either the bottom inlet vent or the top outlet vent.

Gas Leak Failsafe Mechanism 2: In the preferred embodiment, this invention employs a failsafe mechanism to prevent serious damage from an explosion in the case in which there is a significant flammable gas leak within the enclosure 502. If the leak is so large as to achieve explosive concentrations and an ignition does occur, the damage will be minimized by allowing the force to be released through opening of the failsafe top panel 1301 of the enclosure 502. This is accomplished by using a failsafe top panel 1302 which is not rigidly affixed to the enclosure, but rather is on top panel hinges 1303 or some other means of attachment as shown in FIG. 13B. In the case of ignition the top will pop open and move safely out of the way as shown in FIG. 13A.

Gas Leak Failsafe Mechanism 3: In the preferred embodiment, this invention employs a failsafe mechanism that limits the amount of gas used by the gas sorption/desorption analyzer during an experiment. This is achieved by taking the gas from external source (bottle) and filling small internal gas vessel 616 shown in FIG. 6 that is used to supply gas to the gas sorption/desorption analyzer during experimental measurements. An automated valve 612b between the external gas supply and the small internal gas vessel 616 limits the amount of gas used by the gas sorption/desorption analyzer. The automated valve 612b (preferably pneumatic) is a normally closed valve. This valve is opened only at the beginning of an experiment or when the pressure in the internal gas vessel 616 has dropped to a point such that it needs to be refilled. The automated valve 612b is controlled through a computer interface by the software which is used to control the gas sorption/desorption analyzer. A signal generated by the software is sent to an electrical air control solenoid (one of 604a-j) valve that supplies air pressure to open or close the automated valve 612b, filling the internal gas vessel 616 with more gas.

Gas Leak Failsafe Mechanism 4: In the preferred embodiment, this invention employs a failsafe mechanism whereby all automated valves 612a-j except 612k are normally closed valves. Thus, in the event that the electrical power or air supply is cut off, all of these normally closed valves will shut. This limits the amount of gas that could potentially leak from the gas sorption/desorption analyzer to the gas in the small volume between the closed valves where the leak occurred.

Sample Container Pressure Failsafe Mechanism: In the preferred embodiment, this invention employs a failsafe mechanism for gas over-pressurization of the sample container 801 (FIG. 8). This is provided by using a pressure relief valve or a sample container valve 805 which releases gas at a pressure above the normal operating limit of the gas sorption/desorption analyzer (typically 200 atm) but at a pressure (less than 300 atm) that is below the burst pressure of the sample container 801. For example, a failure could occur if the sample container valve 805 was closed and a fully gas loaded sample 814 was heated to a very high temperature. The equilibrium pressure of the gas released could be at elevated pressures high enough to rupture the sample container 801. However, the failsafe mechanism described herein would employ a sample container valve 805 or pressure relief device that would release the gas at pressures lower than the pressure that would rupture the sample container. The preferred sample container valve 805 is typically a diaphragm valve. To provide a pressure failsafe mechanism, this valve should be positioned with the valve seat towards the sample 814 and the valve stem and diaphragm upstream of the sample. At elevated pressures the force of the gas pushing against the stem will cause the valve to unseat releasing the gas from the sample container 801. If the pressure continues to build on both sides of the valve, the diaphragm will rupture and leak. In this case, it is much safer for the diaphragm to rupture than for the sample container to rupture. As an additional measure of safety, a pressure relief device (valve or burst disk) can also be connected on the sample side of the sample container. This device would have its release pressure set above the normal maximum operating pressure of the gas sorption/desorption analyzer but below the rupture pressure of the sample container 801 or other components of the gas sorption/desorption analyzer.

Gas Pressure Failsafe Mechanism: In the preferred embodiment, this invention employs a failsafe mechanism that shuts off the power supply to the gas handling and heating circuits of the electrical system 1101 if the pressure measured by the high pressure transducer 633 indicates that the system pressure is higher than a specified safety limit. The pressure within the calibrated reservoir volume is monitored on a regular basis during most experiments using the high pressure transducer 633. This failsafe mode provides a signal from the controlling software to shut off the power supply to the gas handling and heating circuits if the measured pressure in the reservoir is higher than an upper safety limit set in the software (generally 200 atm).

Power Supply Failsafe Mechanism: In the preferred embodiment, this invention employs a failsafe mechanism that shuts off gas supply if power or air supply is cut off. The pneumatic automated valve 612b that is employed for filling the small internal supply gas vessel 616 from an external gas source (described above) is a normally closed valve. In the event that either electrical power or the air supply to the gas sorption/desorption analyzer 501 is cut off, this pneumatic valve will close. If there is a leak in the gas sorption/desorption analyzer, it will be limited to the amount of gas in the gas sorption/desorption analyzer when the power or air is cut off.

Low Pressure Transducer Failsafe Mechanism: In the preferred embodiment, this invention employs a failsafe mechanism to protect the low pressure transducer 637 from exposure to gas at pressures above the maximum rated pressure of the transducer. In general, the lower range pressure transducers can not be exposed to pressures significantly higher than the upper measuring limit of the transducer without sustaining damage (generally 1.5 times the maximum reading). To protect the low pressure transducer(s), a automated valve 612j is placed between the low pressure transducer 637 and the rest of the system. The automated valve 612j may be controlled (either by software and/or electrical or pneumatic hardware) such that it remains closed if the pressure on the other side of the valve is above the maximum readable pressure of the transducer. In addition, a low pressure transducer failsafe pressure relief valve 638 or burst disc may be placed on the transducer side of the automated valve 612j. This relief valve or burst disc protects the low pressure transducer 637 (which tend to be expensive) by venting or rupturing if the transducer is inadvertently exposed to a pressure greater than the limit of the transducer. In the preferred embodiment of this invention all pressure relief valves or burst discs located inside of the enclosure 502 are connected to a vent line 625 that directs any released gas via the vent connector 626 to an external ventilation system.

One-way Flow Failsafe Mechanism: In the preferred embodiment, this invention employs a set of failsafe one-way check valve mechanisms (e.g. calibration gas check valve 609) to protect certain parts of the gas sorption/desorption analyzer from over-pressurization. These check valves are set to close if the applied pressure exceeds a specified value. This helps to protect any components downstream of the check valve. For example, one such check valve is located on the calibration gas supply line 608 to protect the line from inadvertent over-pressurization or contaminated by high-pressure gas in the system. Another check valve could also be located on the low-pressure transducer gas line 636 between the automated valve 612j and the low pressure transducer failsafe pressure relief valve 638. This provides additional protection to prevent exposing the low pressure transducer 637 to gas at pressures above the maximum rated pressure for the transducer.

Safety Shield In the preferred embodiment, this invention employs a safety mechanism that consists of a sample container safety shield 1201 surrounding the sample container 801 as shown in FIG. 12. The purpose of this shield is to protect the operator or other persons in the event that the sample container 801, gas lines or other fixtures fail in a catastrophic manner. The see-through safety shield 1202 would be composed preferably of a material that is transparent and strong such as Lexan. The shield is designed to stop objects flying in most directions away from the area of the sample container 801. The shield is mounted on safety shield hinges 1204 so that it may be opened to change the sample or perform other operations within its space. During experiments, the shield is latched in the closed position using a safety shield latch hook 1205 and pin 1206 such as shown in FIG. 12.

Safety Shield Failsafe Mechanism: In the preferred embodiment, this invention employs a failsafe mechanism to shut off power to the sample heater furnace 701 or heating jacket 1001 if the sample container safety shield 1201 described above is opened. This is achieved using a low voltage sample container safety shield switch 1121 (such as a push-button switch) that is pushed into the closed position by the see-through safety shield 1202 when the shield is closed properly. This switch forms a safety circuit as shown in FIG. 11 connected to the sample heater control relay 1109 which controls the furnace 701 or heating jacket 1001. If the safety circuit is broken by opening the see-through safety shield 1202, the sample heater control relay 1109 will open, shutting off power to the furnace 701 or heating jacket 1001.

Sample Heater Failsafe Mechanism: In the preferred embodiment, this invention employs a failsafe mechanism to shut off power to the sample heater furnace 701 or heating jacket 1001, if the temperature of the sample container 801 goes above 450.degree. C. This is achieved by monitoring an thermocouple (705, 706, or 707) other than the thermocouple that is being used to control the temperature of furnace 701 or heating jacket 1001. If this other thermocouple (705, 706, or 707) registers (when monitored by the computer 506) a temperature greater than 450.degree. C. it shuts off the power to the furnace 701 or heating jacket 1001 by opening the sample heater control relay 1109. In an alternative embodiment the entire system power can be shut off using the power safety relay 1127 if after some time the computer still registers a temperature greater than 450.degree. C. in the furnace 701 or heating jacket 1001.

I claim:

1. A gas handling apparatus to provide gas from a substance for measuring gas sorption and desorption properties of the substance, said apparatus comprising:
   a sample container for containing said substance;
   a gas storage reservoir for storing a gas;
   a gas supply source for supplying said gas to said gas storage reservoir;
   a first gas transmission line connecting said gas supply source to said gas storage reservoir, said first gas transmission line provided with a first gas valve;
   a gas discharge line connected to said gas storage reservoir, said gas discharge line provided with a second gas valve;
   a second gas transmission line connecting said gas storage reservoir and said sample container, said second gas transmission line provided with a third gas valve; and
   a valve control means for controlling opening and closing said first, second and third valves to intermittently supply and discharge said gas from said gas storage reservoir to said sample container.

2. The apparatus of claim 1, wherein said valve control means comprises a computer means operatively controlling a valve actuator means separately connected to each of said first, second and third valves.

3. The apparatus of claim 1, wherein each of said first and second gas transmission lines, said gas discharge line, said gas storage reservoir, said sample container, and said first, second, and third valves are operable at gas pressures up to at least 200 atm.

4. The apparatus of claim 1, wherein said apparatus further comprises an inlet gas pressure regulator, said inlet gas pressure regulator operably connected to said gas supply, said inlet gas pressure regulator supplying said gas to said gas storage reservoir at a predetermined pressure.

5. The apparatus of claim 4, wherein said inlet gas pressure regulator is computer controlled.

6. The apparatus of claim 4, wherein said inlet gas pressure regulator is PID regulated.

7. The apparatus of claim 4, wherein said predetermined pressure is a constant differential gas pressure above a measured gas pressure within said sample container.

8. The apparatus of claim 1, wherein each of said valves is actuated electrically, or pneumatically, or electrically and pneumatically.

9. The apparatus of claim 1, wherein each of said gas valves comprises a normally closed type except said third gas valve comprises a normally open type.

10. The apparatus of claim 1, wherein said sample container further comprises pressure relief means to discharge a pressurized gas above a certain pressure.

11. The apparatus of claim 1, wherein some of said valves close in the event of loss of electrical power or of pneumatic control gas pressure.

12. The apparatus of claim 1, further comprising a sample container heating means.

13. The apparatus of claim 12, wherein said sample container heating means further comprises PID regulation of the temperature of said substance.

14. The apparatus of claim 1, further comprising a gas storage reservoir heating means.

15. The apparatus of claim 14, wherein said gas storage reservoir heating means further comprises PID regulation of the temperature of said gas in said gas storage reservoir.

16. The apparatus of claim 1, further comprising means for volume calibration, wherein said means for volume calibration includes using a non-absorbing gas.

17. The apparatus of claim 1, further comprising means for volume and density measurements of said substance.

18. The apparatus of claim 1, wherein said substance is an hydrogen absorbing substance and said gas is hydrogen.

19. The apparatus of claim 1, wherein said substance is an oxygen absorbing substance and said gas is or contains oxygen.

20. The apparatus of claim 1, further comprising an automatic means to first discharge gas from said gas storage reservoir to an atmospheric vent line, then to discharge gas from said gas storage reservoir to an evacuation system.

21. A gas handling apparatus to direct gas from a substance for measuring gas sorption and desorption of the substance, said apparatus comprising:
- a sample container for containing said substance;
- a gas storage reservoir for storing a gas;
- an inlet gas supply source for supplying said gas to said gas storage reservoir;
- a computer controlled inlet gas pressure regulator, said inlet gas pressure regulator providing said gas from said inlet gas supply source to said gas storage reservoir at a predetermined pressure;
- a first gas transmission line connecting said inlet gas pressure regulator to said gas storage reservoir, said first gas transmission line provided with a first gas valve;
- a second gas transmission line connecting said gas storage reservoir and said sample container, said second gas transmission line provided with a second gas valve; and
- a valve control means for controlling opening and closing said first and second gas valves to intermittently supply and discharge said gas from said gas storage reservoir to said sample container.

22. The apparatus of claim 21, further comprising means for regulating temperature within said sample container.

23. The apparatus of claim 22, wherein said means for regulating temperature within said sample container further comprising PID regulation of the temperature of said substance.

24. The apparatus of claim 21, further comprising means for regulating temperature of said gas in said gas storage reservoir.

25. The apparatus of claim 24, wherein said means for regulating temperature of said gas in said gas storage reservoir further comprising PID regulation of the temperature of said gas in said gas storage reservoir.

26. The apparatus of claim 21, wherein each of said valves is actuated electrically, or pneumatically, or electrically and pneumatically.

27. The apparatus of claim 21, wherein said first gas valve comprises a normally closed type, and said second gas valve comprises a normally open type.

28. The apparatus of claim 21, wherein said sample container further comprises pressure relief means to discharge a pressurized gas above a certain pressure.

29. The apparatus of claim 21, wherein some of said valves close in the event of loss of electrical power or of pneumatic control gas pressure.

30. The apparatus of claim 21, further comprising automatic computation means to compensate for non-ideal behavior of said gas or mixture of gases.

31. The apparatus of claim 21, further comprising minimized volumes of said first and second gas transmission lines, said gas storage reservoir, said first and second gas valves, and said sample container.

32. The apparatus of claim 21, further comprising a plurality of pressure sensors.

33. The apparatus of claim 21, further comprising means for increasing or decreasing an amount of said gas provided to or discharged from said sample container.

34. The apparatus of claim 33, wherein said means for increasing or decreasing an amount of said gas provided to, or discharged from, said sample container further comprises one or more additional gas volumes.

35. The apparatus of claim 21, further comprising an enclosure surrounding said gas storage reservoir.

36. The apparatus of claim 35, further comprising means for relieving pressure within said enclosure, said means for relieving pressure including ventilation means.

37. The apparatus of claim 21, further comprising a gas limiting safety means comprising a third gas valve and gas supply container connected between said gas supply source and said inlet gas pressure regulator.

38. The apparatus of claim 21, further comprising a power interlock means to shut off power to said apparatus in the event that said enclosure is opened.

39. The apparatus of claim 21, further comprising gas back-flow restriction means to prevent said gas from flowing back to said inlet gas supply source or other gas supply sources.

40. The apparatus of claim 21, further comprising a safety shield partially surrounding said sample container.

41. The apparatus of claim 40, further comprising safety shut off means to automatically shut off power to sample heating means when said safety shield is in an open position or when said sample heating means exceeds a predetermined temperature.

42. The apparatus of claim 21, further comprising an enclosure temperature safety shut off for shutting off power to said apparatus when temperature within said enclosure exceeds a predetermined temperature.

43. The apparatus of claim 21, further comprising a gas discharge line connected to said gas storage reservoir, said gas discharge line provided with a gas valve for discharging said gas from said gas storage reservoir to said gas discharge line.

44. The apparatus of claim 21, wherein said inlet gas pressure regulator further comprises PID regulation of the pressure of said gas.

45. The apparatus of claim 21, wherein said predetermined pressure is a constant differential gas pressure above a measured gas pressure within said sample container.

46. The apparatus of claim 21, further comprising means for sorption and desorption measurements, wherein said substance is maintained under a constant pressure.

47. The apparatus of claim 21, wherein said substance is an hydrogen absorbing substance, and said gas is hydrogen.

48. The apparatus of claim 21, wherein said substance is an oxygen absorbing substance, and said gas is oxygen.

* * * * *